United States Patent
Fujita et al.

(10) Patent No.: US 7,435,455 B2
(45) Date of Patent: Oct. 14, 2008

(54) DIHYDROCOUMARIN DERIVATIVE, LIQUID CRYSTAL COMPOSITION CONTAINING THE SAME, AND LIQUID CRYSTAL DISPLAY DEVICE

(75) Inventors: Atsuko Fujita, Chiba (JP); Kouki Sago, Chiba (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 473 days.

(21) Appl. No.: 11/304,683

(22) Filed: Dec. 16, 2005

(65) Prior Publication Data

US 2006/0131541 A1 Jun. 22, 2006

(30) Foreign Application Priority Data

Dec. 16, 2004 (JP) ............... 2004-364423

(51) Int. Cl.
| | |
|---|---|
| C09K 19/34 | (2006.01) |
| C09K 19/32 | (2006.01) |
| C09K 19/30 | (2006.01) |
| C09K 19/12 | (2006.01) |
| C09K 19/20 | (2006.01) |
| C07D 311/06 | (2006.01) |
| C07D 311/58 | (2006.01) |
| C07D 311/74 | (2006.01) |

(52) U.S. Cl. ............. 428/1.1; 252/299.01; 252/299.61; 252/299.62; 252/299.66; 252/299.67; 549/23; 549/283; 549/289; 549/290

(58) Field of Classification Search .................. 428/1.1; 252/299.01, 299.61, 299.62, 299.63, 299.66, 252/299.67; 549/23, 283, 289, 290
See application file for complete search history.

(56) References Cited

OTHER PUBLICATIONS

CA: 147: 529080, 2007.*

M.A. Sayed et al., "Action of Nitrogen and Carbon Nucleophiles on 6-Phenyl-3, 4-Dihydrocoumarin", Oriental Journal of Chemistry, vol. 3, No. 2, 1987, pp. 174-178.

Stephen G. Davies et al., "Synthesis of 6-substituted-3,4-dihydro-2H-1-benzopyran-2-ones(dihydrocoumarins) via palladium catalysed coupling reactions", Journal of Organometallic Chemistry, 387(3), 1990, pp. 381-390.

* cited by examiner

*Primary Examiner*—Shean C Wu
(74) *Attorney, Agent, or Firm*—Wenderoth, Lind & Ponack, L.L.P.

(57) ABSTRACT

A dihydrocoumarin ring-containing compound of the invention is represented by the following formula (1):

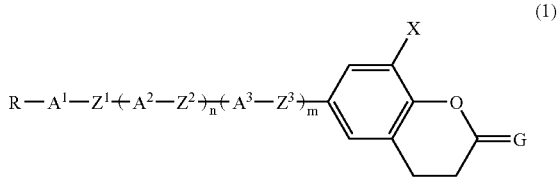

wherein R represents hydrogen or an alkyl; $A^1$ to $A^3$ each represents 1,4-cyclohexylene or 1,4-phenylene; $Z^1$ to $Z^3$ each represents a single bond, $-(CH_2)_2-$, $-CH_2O-$, $-OCH_2-$, $-CF_2O-$, $-OCF_2-$, $-CH=CH-$, $-CF=CF-$, $-C\equiv C-$, $-(CH_2)_4-$, $-O(CH_2)_2O-$, $-(CH_2)_2CF_2O-$, $-(CH_2)_2OCF_2-$, $-CF_2O(CH_2)_2-$, $-OCF_2(CH_2)_2-$, $-CH=CH-CH_2O-$, or $-OCH_2-CH=CH-$; X represents hydrogen, fluorine, chlorine, $-CN$, $-CF_3$, $-CHF_2$, $-CH_2F$, $-OCF_3$, $-OCHF_2$, or $-OCH_2F$; G represents oxygen or sulfur; and n and m each represents 0, 1, or 2.

36 Claims, No Drawings

DIHYDROCOUMARIN DERIVATIVE, LIQUID CRYSTAL COMPOSITION CONTAINING THE SAME, AND LIQUID CRYSTAL DISPLAY DEVICE

FIELD OF THE INVENTION

The present invention relates to a liquid crystalline compound, a liquid crystal composition, and a liquid crystal display device. In more detail, the invention relates to a dihydrocoumarin compound, a liquid crystal composition containing the same and having a nematic phase, and a liquid crystal display device containing this composition.

BACKGROUND OF THE INVENTION

A liquid crystal display device is classified, on the basis of an operation mode of liquid crystal, into PC (phase change), TN (twisted nematic), STN (super twisted nematic), BTN (bistable twisted nematic), ECB (electrically controlled birefringence), OCB (optically compensated bend), IPS (in-plane switching) and VA (vertical alignment) devices, and the like. Then, the liquid crystal display device is classified, on the basis of a drive system of device, into PM (passive matrix) and AM (active matrix) devices. The PM (passive matrix) device is classified into static and multiplex devices, and the like; and the AM device is classified into TFT (thin film transistor) and MIM (metal insulator metal) devices, and the like.

These devices contain a liquid crystal composition. In order to improve characteristics of the device, it is preferable that this composition has adequate physical properties. General physical properties which a compound as a component of the composition is required to have are as follows.
(1) Chemical stability and physical stability.
(2) High clearing point. The clearing point is a transition temperature between a liquid crystal phase and an isotropic phase.
(3) Low lower limit temperature of a liquid crystal phase. The liquid crystal phase as referred to herein means a nematic phase, a smectic phase, or the like.
(4) Low viscosity.
(5) Adequate optical anisotropy.
(6) Adequate dielectric anisotropy. In many cases, a compound having large dielectric anisotropy has a high viscosity.
(7) High resistivity.

A liquid crystal composition is prepared by mixing a lot of liquid crystalline compounds. Accordingly, it is preferable that such a liquid crystalline compound is well miscible with other compounds. Since a device may possibly be used at a below-freezing temperature, compounds having well compatibility at low temperatures are preferable. A compound having a high clearing point or a low lower limit temperature of a liquid crystal phase contributes to the wide temperature range of a nematic phase in the composition. A preferred composition has a low viscosity and optical anisotropy suitable for the mode of a device. Large dielectric anisotropy of a compound contributes to a low threshold voltage of a composition. By using such a composition, it is possible to obtain a device having characteristics such that the useful temperature range is broad; the response time is short; the contrast ratio is large; the drive voltage is small; the electric power consumption is low; and the voltage retention is high.

Hitherto, there have been scarcely known examples in which a dihydrocoumarin derivative is applied as a liquid crystal display device. The following group of compounds having a structure analogous to a liquid crystal has been known up to date. However, in all of these compounds, their applications are not relevant to a liquid crystal display device, and characteristics, physical properties, and the like of these compounds as a liquid crystal are not clarified at all.

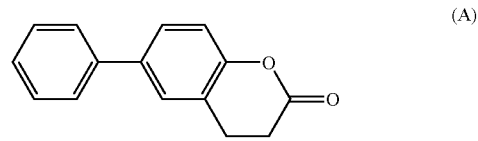

(A)

Oriental Journal of Chemistry (1987), 3(2), 174-8

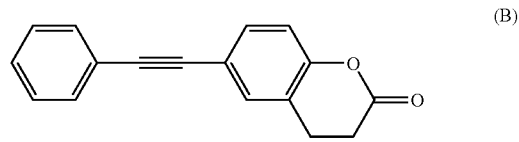

(B)

Journal of Organometallic Chemistry (1990), 387(3), 381-90

SUMMARY OF THE INVENTION

A first object of the invention is to provide a liquid crystalline compound having general physical properties necessary for a compound, a low viscosity, adequate optical anisotropy, adequate dielectric anisotropy and excellent compatibility with other liquid crystalline compounds. A second object of the invention is to provide a liquid crystal composition containing this compound and having a wide temperature range of a nematic phase, a low viscosity, adequate optical anisotropy and a low threshold voltage. A third object of the invention is to provide a liquid crystal display device containing this composition and having a short response time, a low electric power consumption, a large contrast and a high voltage retention.

The first item of the present invention is the following item [1].

[1] A compound represented by the following formula (1):

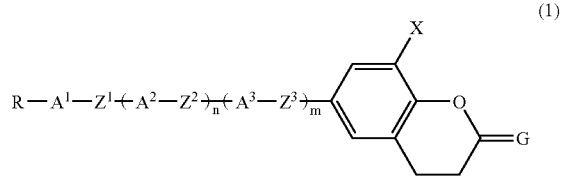

(1)

wherein

R represents an alkyl having from 1 to 20 carbon atoms; and in this alkyl, any —$CH_2$— may be replaced by —O—, —S—, —CO—, —CH=CH—, or —C≡C—;

$A^1$, $A^2$, and $A^3$ each independently represents 1,4-cyclohexylene or 1,4-phenylene; in the 1,4-cyclohexylene, any —$CH_2$— may be replaced by —O—, —S—, or —CO—, and any —$(CH_2)_2$— may be replaced by —CH=CH—; in the 1,4-phenylene, any —CH= may be replaced by —N=; and in these rings, any hydrogen may be replaced by fluorine, chlorine, —CN, —$CF_3$, —$CHF_2$, —$CH_2F$, —$OCF_3$, —$OCHF_2$, or —$OCH_2F$;

$Z^1$, $Z^2$, and $Z^3$ each independently represents a single bond, —$(CH_2)_2$—, —$CH_2O$—, —$OCH_2$—, —$CF_2O$—, —$OCF_2$—, —$CH=CH$—, —$CF=CF$—, —$C\equiv C$—, —$(CH_2)_4$—, —$O(CH_2)_2O$—, —$(CH_2)_2CF_2O$—, —$(CH_2)_2OCF_2$—, —$CF_2O(CH_2)_2$—, —$OCF_2(CH_2)_2$—, —$CH=CH-CH_2O$—, or —$OCH_2-CH=CH$—;

X represents hydrogen, fluorine, chlorine, —CN, —$CF_3$, —$CHF_2$, —$CH_2F$, —$OCF_3$, —$OCHF_2$—, or —$OCH_2F$;

G represents oxygen or sulfur;

n and m each independently represents 0, 1, or 2; and in any one of the following (i) to (iii), R may represent hydrogen:

(i) the total sum of n and m is 1 or 2;

(ii) X represents fluorine, chlorine, —CN, —$CF_3$, —$CHF_2$, —$CH_2F$, —$OCF_3$, —$OCHF_2$, or —$OCH_2F$; and (iii) at least one of $A^1$, $A^2$, and $A^3$ represents 1,4-phenylene in which any hydrogen is replaced by fluorine, chlorine, —CN, —$CF_3$, —$CHF_2$, —$CH_2F$, —$OCF_3$, —$OCHF_2$, or —$OCH_2F$.

DETAILED DESCRIPTION OF THE INVENTION

The terms as used in this specification have the following meanings. The liquid crystalline compound is a general term of compounds which have a liquid crystal phase such as a nematic phase and a smectic phase and compounds which do not have a liquid crystal phase but are useful as a component of a liquid crystal composition. The liquid crystalline compound, the liquid crystal composition, and the liquid crystal display device may be abbreviated as "compound", "composition", and "device", respectively. The liquid crystal display device is a general term of liquid crystal display panels and liquid crystal display modules. An upper limit temperature of the nematic phase is a phase transition temperature between the nematic phase and an isotropic phase, and may be abbreviated simply as "upper limit temperature". A lower limit temperature of the nematic phase may be abbreviated simply as "lower limit temperature". The compound represented by the formula (1) may be abbreviated as "compound (1)". This abbreviation may be applied to the compound represented by the formula (2) or the like. In the formulae (2) to (14), symbols such as B, D and E surrounded by a hexagon are corresponding to ring B, ring D, and ring E, respectively. The amount of a compound expressed by the percentage is a weight percentage (% by weight) based on the total weight of the composition.

It is meant by the term "any" that not only the position but also the number is any, with proviso that the case where the number is 0 is excluded. It is meant by the expression "any A may be replaced by B, C or D" that the case where multiple As are replaced by at least two of B to D is included in addition to the case where any A is replaced by B, the case where any A is replaced by C, and the case where any A is replaced by D. For example, the alkyl in which any —$CH_2$— may be replaced by —O— or —CH=CH— includes an alkyl, an alkenyl, an alkoxy, an alkoxyalkyl, an alkoxyalkenyl, and an alkenyloxyalkyl. Incidentally, in the invention, it is not preferable that the continuing two of —$CH_2$— is replaced by —O— or —S— to form —O—O—, —O—S—, or —S—S—. Also, it is not preferable that in the alkyl, the terminal —$CH_2$— is replaced by —O— or —S—.

The present invention is constructed of the above item [1] and the following items from [2] to [33].

[2] A compound represented by the following formula (1):

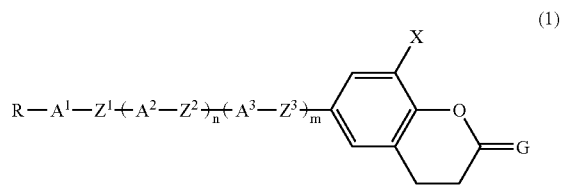

wherein

R represents an alkyl having from 1 to 15 carbon atoms, an alkoxy having from 1 to 15 carbon atoms, an alkoxyalkyl having from 2 to 15 carbon atoms, or an alkenyl having from 2 to 15 carbon atoms;

$A^1$, $A^2$, and $A^3$ each independently represents 1,4-cyclohexylene, 1,4-phenylene, fluorinated 1,4-phenylene, or 1,3-dioxane-2,5-diyl;

G represents oxygen or sulfur;

$Z^1$, $Z^2$, and $Z^3$ each independently represents a single bond, —$(CH_2)_2$—, —$CH_2O$—, or —$OCH_2$—, X represents fluorine or hydrogen;

n and m each independently represents 0 or 1; and in any one of the following (iv) to (vi), R may represents hydrogen:

(iv) the total sum of n and m is 1 or 2;

(v) X represents fluorine; and (vi) at least one of $A^1$, $A^2$, and $A^3$ represents 1,4-phenylene in which any hydrogen is replaced by fluorine.

[3] The compound as set forth in the item [2], wherein G represents oxygen; and $Z^1$, $Z^2$, and $Z^3$ each represents a single bond.

[4] The compound as set forth in the item [2], wherein G represents oxygen; $Z^1$, $Z^2$, and $Z^3$ each represents a single bond; and $A^1$, $A^2$, and $A^3$ each independently represents 1,4-cyclohexylene, 1,4-phenylene, or fluorinated 1,4-phenylene.

[5] The compound as set forth in the item [2], wherein G represents oxygen; $Z^1$, $Z^2$, and $Z^3$ each represents a single bond; $A^1$, $A^2$, and $A^3$ each independently represents 1,4-cyclohexylene, 1,4-phenylene, or fluorinated 1,4-phenylene; and R represents an alkyl having from 1 to 15 carbon atoms.

[6] The compound as set forth in the item [5], wherein any one of $A^1$, $A^2$, and $A^3$ represents fluorinated 1,4-phenylene.

[7] The compound as set forth in the item [2], wherein G represents oxygen; $Z^1$, $Z^2$, and $Z^3$ each represents a single bond; $A^1$, $A^2$, and $A^3$ each independently represents 1,4-cyclohexylene, 1,4-phenylene, or fluorinated 1,4-phenylene; and R represents an alkenyl having from 2 to 15 carbon atoms.

[8] The compound as set forth in the item [7], wherein any one of $A^1$, $A^2$, and $A^3$ represents fluorinated 1,4-phenylene.

[9] The compound as set forth in the item [2], wherein G represents oxygen; $Z^1$, $Z^2$, and $Z^3$ each represents a single bond; and any one of $A^1$, $A^2$, and $A^3$ represents 1,4-cyclohexylene.

[10] The compound as set forth in the item [2], wherein G represents oxygen; and any one of $Z^1$, $Z^2$, and $Z^3$ represents —$CH_2O$— or —$OCH_2$—.

[11] The compound as set forth in the item [2], wherein G represents oxygen; any one of $Z^1$, $Z^2$, and $Z^3$ represents —$CH_2O$— or —$OCH_2$—; and $A^1$, $A^2$, and $A^3$ each independently represents 1,4-cyclohexylene, 1,4-phenylene, or fluorinated 1,4-phenylene.

[12] The compound as set forth in the item [2], wherein G represents oxygen; and any one of $Z^1$, $Z^2$, and $Z^3$ represents —$(CH_2)_2$—.

[13] The compound as set forth in the item [2], wherein G represents oxygen; any one of $Z^1$, $Z^2$, and $Z^3$ represents —$(CH_2)_2$—; and $A^1$, $A^2$, and $A^3$ each independently represents 1,4-cyclohexylene, 1,4-phenylene, or fluorinated 1,4-phenylene.

[14] The compound as set forth in the item [2], wherein G represents oxygen; any one of $Z^1$, $Z^2$, and $Z^3$ represents —$(CH_2)_2$—; $A^1$, $A^2$, and $A^3$ each independently represents 1,4-cyclohexylene, 1,4-phenylene, or fluorinated 1,4-phenylene; and R represents an alkyl having from 1 to 15 carbon atoms.

[15] The compound as set forth in the item [14], wherein any one of $A^1$, $A^2$, and $A^3$ represents fluorinated 1,4-phenylene.

[16] The compound as set forth in the item [2], wherein G represents oxygen; any one of $Z^1$, $Z^2$, and $Z^3$ represents —$(CH_2)_2$—; $A^1$, $A^2$, and $A^3$ each independently represents 1,4-cyclohexylene, 1,4-phenylene, or fluorinated 1,4-phenylene; and R represents an alkenyl having from 2 to 15 carbon atoms.

[17] The compound as set forth in the item [16], wherein any one of $A^1$, $A^2$, and $A^3$ represents fluorinated 1,4-phenylene.

[18] The compound as set forth in the item [2], wherein G represents sulfur.

[19] A compound represented by any one of the following formulae (1a) to (1m):

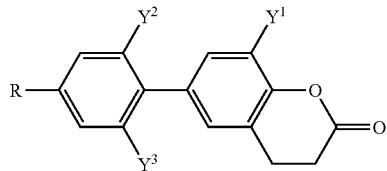

1a

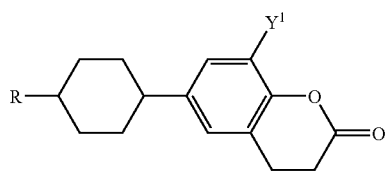

1b

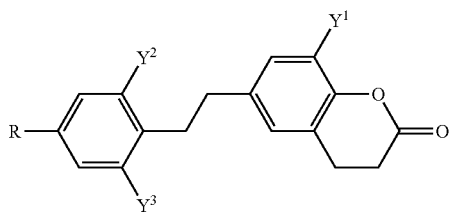

1c

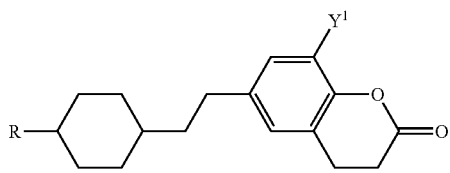

1d

-continued

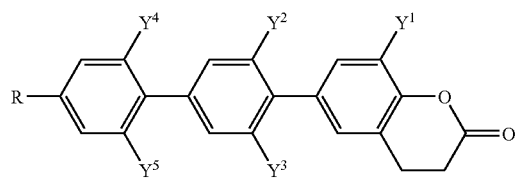

1e

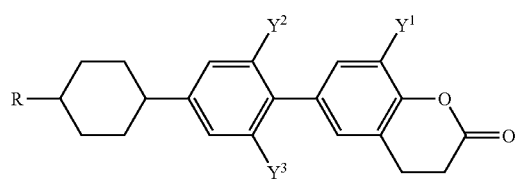

1f

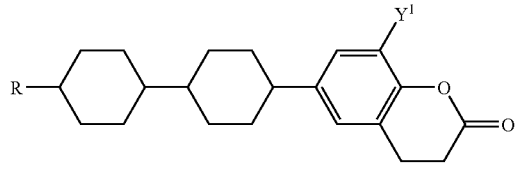

1g

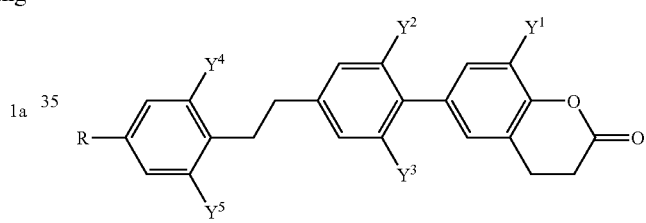

1h

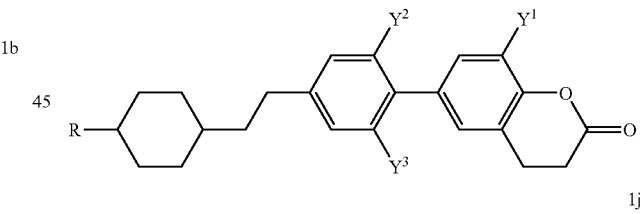

1i

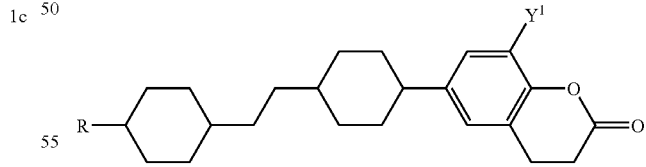

1j

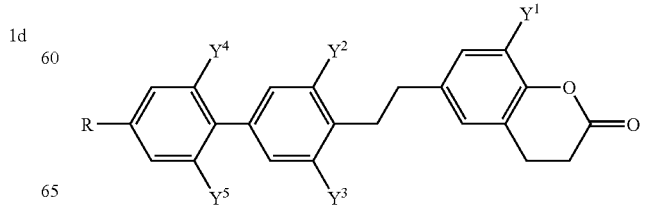

1k

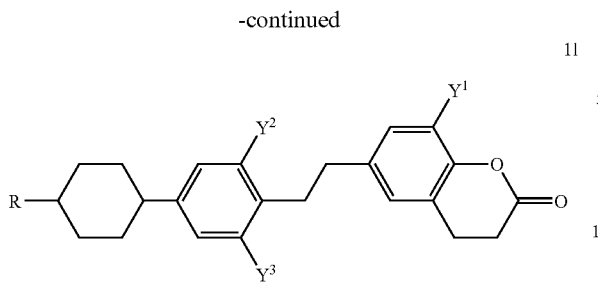

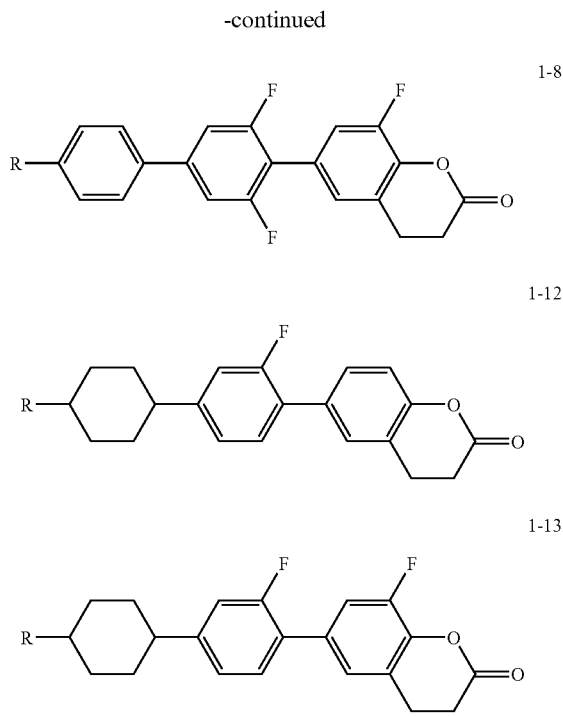

wherein R represents an alkyl having from 1 to 15 carbon atoms, an alkoxy having from 1 to 15 carbon atoms, or an alkenyl having from 2 to 15 carbon atoms; and $Y^1$ to $Y^5$ each independently represents hydrogen or fluorine.

[20] The compound as set forth in the item [19], wherein R represents an alkyl having from 1 to 7 carbon atoms, an alkoxy having from 1 to 4 carbon atoms, or an alkenyl having from 2 to 7 carbon atoms.

[21] The compound as set forth in the item [19], wherein R represents an alkyl having from 1 to 7 carbon atoms, an alkoxy having from 1 to 4 carbon atoms, or an alkenyl having from 2 to 7 carbon atoms; and any one of $Y^1$ to $Y^5$ represents fluorine.

[22] A compound represented by any one of the following formulae:

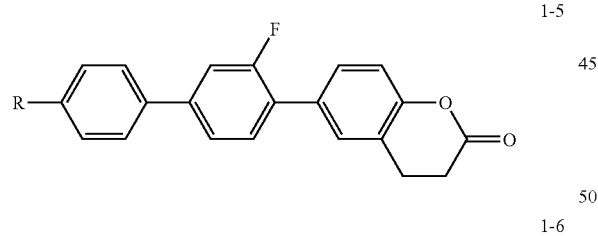

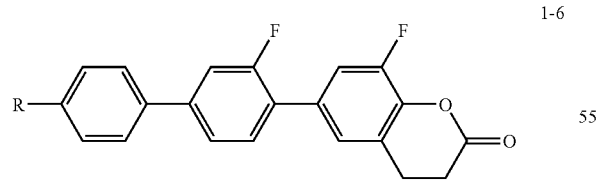

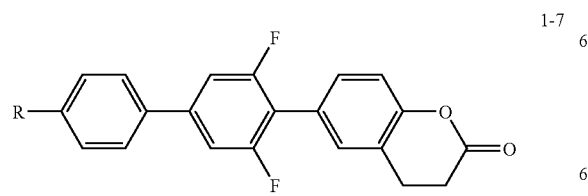

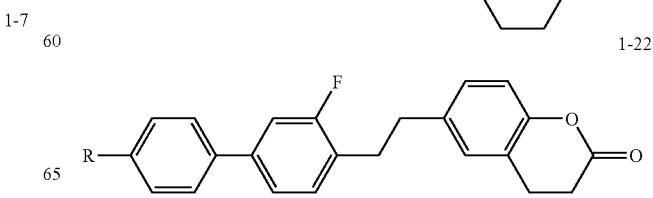

-continued 1-23
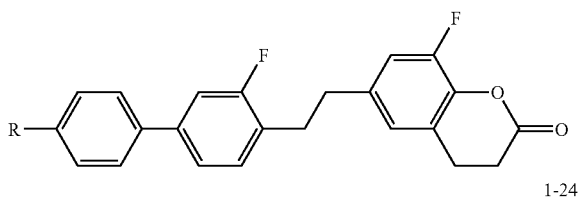

1-24
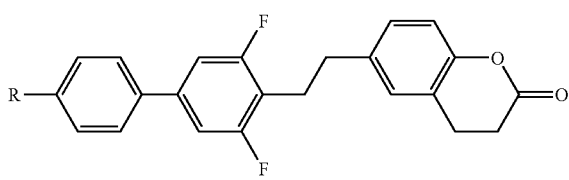

1-25
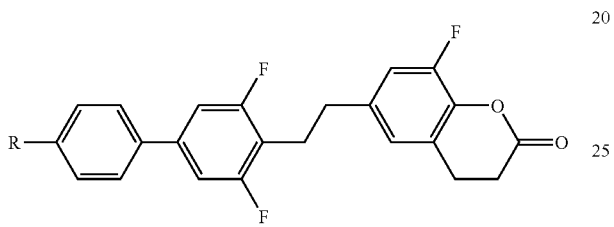

1-29
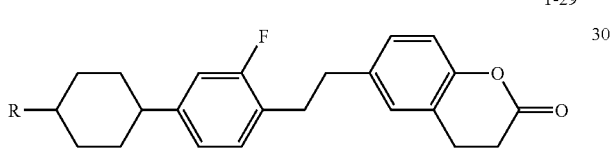

1-30
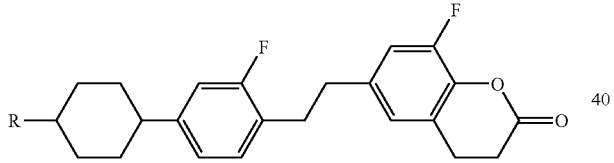

1-31
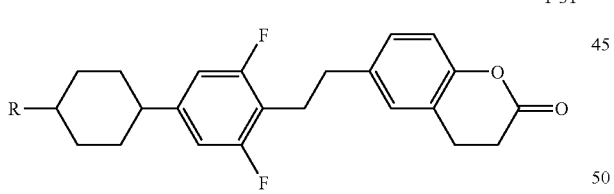

1-32
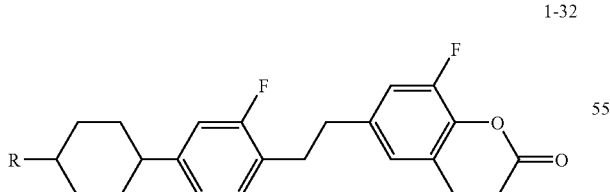

1-33
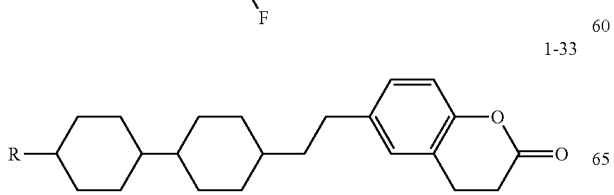

-continued 1-34
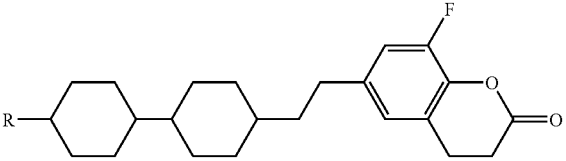

wherein R represents an alkyl having from 1 to 7 carbon atoms, an alkoxy having from 1 to 4 carbon atoms, or an alkenyl having from 2 to 7 carbon atoms.

[23] A liquid crystal composition containing at least one compound as set forth in any one of the items [1] to [22] and comprising at least two compounds.

[24] The liquid crystal composition as set forth in the item [23], containing at least one compound selected from the group consisting of compounds represented by the following formulae (2), (3) and (4):

(2)
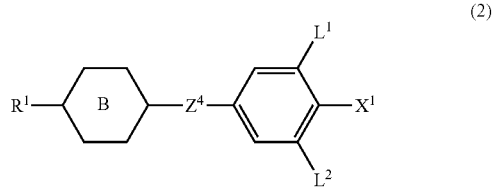

(3)
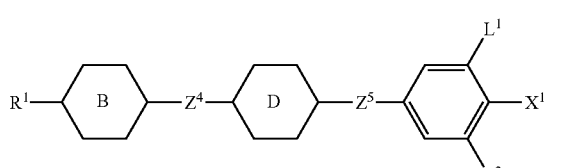

(4)
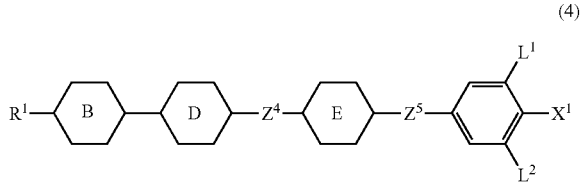

wherein $R^1$ represents an alkyl having from 1 to 10 carbon atoms; and in this alkyl, any —$CH_2$— may be replaced by —O— or —CH=CH—, and any hydrogen may be replaced by fluorine;

$X^1$ represents fluorine, chlorine, —$OCF_3$, —$OCHF_2$, —$CF_3$, —$CHF_2$, —$CH_2F$, —$OCF_2CHF_2$, or —$OCF_2CHFCF_3$;

ring B and ring D each independently represents 1,4-cyclohexylene, 1,4-phenylene, 1,3-dioxane-2,5-diyl, or fluorinated 1,4-phenylene;

ring E represents 1,4-cyclohexylene, 1,4-phenylene, or fluorinated 1,4-phenylene;

$Z^4$ and $Z^5$ each independently represents —$(CH_2)_2$—, —$(CH_2)_4$—, —COO—, —$CF_2O$—, —$OCF_2$—, —CH=CH—, or a single bond; and $L^1$ and $L^2$ each independently represents hydrogen or fluorine.

[25] The liquid crystal composition as set forth in the item [23], containing at least one compound selected from the group consisting of compounds represented by the following formulae (5) and (6):

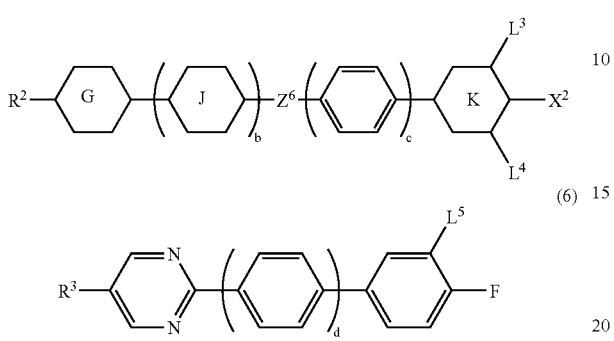

(5)

(6)

wherein $R^2$ and $R^3$ each independently represents an alkyl having from 1 to 10 carbon atoms; and in this alkyl, any —$CH_2$— may be replaced by —O— or —CH=CH—, and any hydrogen may be replaced by fluorine;

$X^2$ represents —CN or —C≡C—CN;

ring G represents 1,4-cyclohexylene, 1,4-phenylene, 1,3-dioxane-2,5-diyl, or pyrimidine-2,5-diyl;

ring J represents 1,4-cyclohexylene, 1,4-phenylene, pyrimidine-2,5-diyl, or fluorinated 1,4-phenylene;

ring K represents 1,4-cyclohexylene or 1,4-phenylene;

$Z^6$ represents —$(CH_2)_2$—, —COO—, —$CF_2O$—, —$OCF_2$—, or a single bond;

$L^3$, $L^4$, and $L^5$ each independently represents hydrogen or fluorine; and b, c, and d each independently represents 0 or 1.

[26] The liquid crystal composition as set forth in the item [23], containing at least one compound selected from the group consisting of compounds represented by the following formulae (7), (8), (9), (10) and (11):

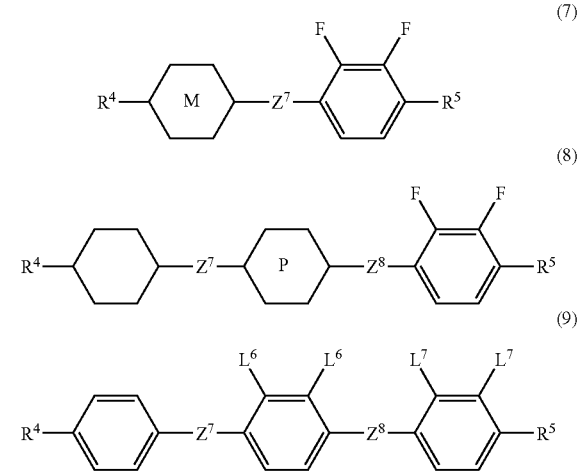

(7)

(8)

(9)

(10)

(11)

wherein $R^4$ represents an alkyl having from 1 to 10 carbon atoms; and in this alkyl, any —$CH_2$— may be replaced by —O— or —CH=CH—, and any hydrogen may be replaced by fluorine;

$R^5$ represents fluorine or an alkyl having from 1 to 10 carbon atoms; and in this alkyl, any —$CH_2$— may be replaced by —O— or —CH=CH—, and any hydrogen may be replaced by fluorine;

ring M and ring P each independently represents 1,4-cyclohexylene, 1,4-phenylene, or decahydro-2,6-naphthylene;

$Z^7$ and $Z^8$ each independently represents —$(CH_2)_2$—, —COO—, or a single bond; and $L^6$ and $L^7$ each independently represents hydrogen or fluorine, and at least one of $L^6$ and $L^7$ represents fluorine.

[27] The liquid crystal composition as set forth in the item [23], containing at least one compound selected from the group consisting of compounds represented by the following formulae (12), (13) and (14):

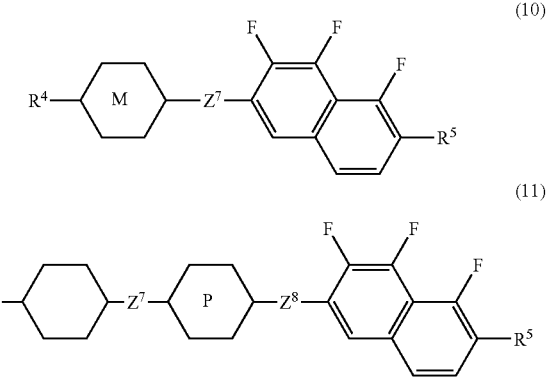

(12)

(13)

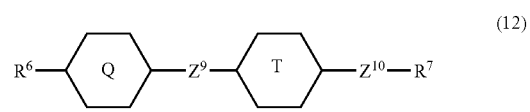

(14)

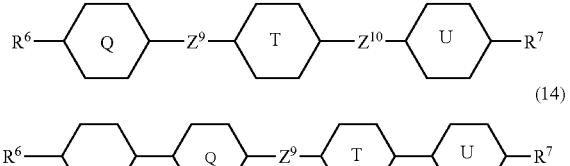

wherein $R^6$ and $R^7$ each independently represents an alkyl having from 1 to 10 carbon atoms; and in this alkyl, any —$CH_2$— may be replaced by —O— or —CH=CH—, and any hydrogen may be replaced by fluorine;

ring Q, ring T, and ring U each independently represents 1,4-cyclohexylene, 1,4-phenylene, pyrimidine-2,5-diyl, or fluorinated 1,4-phenylene; and $Z^9$ and $Z^{10}$ each independently represents —C≡C—, —COO—, —$(CH_2)_2$—, —CH=CH—, or a single bond.

[28] The liquid crystal composition as set forth in the item [24], containing at least one compound selected from the group consisting of compounds represented by the formulae (5) and (6) as set forth in the item [25].

[29] The liquid crystal composition as set forth in the item [24], containing at least one compound selected from the group consisting of compounds represented by the formulae (12), (13) and (14) as set forth in the item [27].

[30] The liquid crystal composition as set forth in the item [25], containing at least one compound selected from the group consisting of compounds represented by the formulae (12), (13) and (14) as set forth in the item [27].

[31] The liquid crystal composition as set forth in the item [26], containing at least one compound selected from the group consisting of compounds represented by the formulae (12), (13) and (14) as set forth in the item [27].

[32] The liquid crystal composition as set forth in any one of the items [23] to [31], further containing at least one optically active compound.

[33] A liquid crystal display device containing the liquid crystal composition as set forth in any one of the items [23] to [32].

The compound of the invention is a compound represented by the following formula (1).

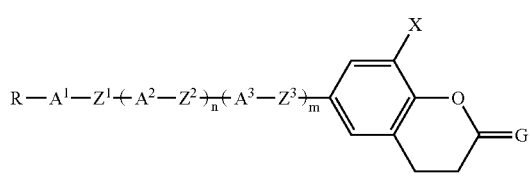

In the formula (1), R represents an alkyl having from 1 to 20 carbon atoms. In this alkyl, any —$CH_2$— may be replaced by —O—, —S—, —CO—, —CH=CH—, or —C≡C—. For example, examples of a group of $CH_3(CH_2)_3$— in which any —$CH_2$— is replaced by —O—, —S—, —CH=CH—, or —C≡C— include $CH_3(CH_2)_2O$—, $CH_3$—O—$(CH_2)_2$—, $CH_3$—O—$CH_2$—O—, $CH_3(CH_2)_2S$—, $CH_3$—S—$(CH_2)_2$—, $CH_3$—S—$CH_2$—S—, $CH_2$=CH—$(CH_2)_3$—, $CH_3$—CH=CH—$(CH_2)_2$—, $CH_3$—CH=CH—$CH_2$O—, and $CH_3$—C≡C—$(CH_2)_2$—.

Examples of such R include an alkyl, an alkoxy, an alkoxyalkyl, an alkoxyalkoxy, an alkylthio, an alkylthioalkyl, an acyl, an acylalkyl, an acyloxy, an acyloxyalkyl, an alkoxycarbonyl, an alkoxycarbonylalkyl, an alkenyl, an alkenyloxy, an alkenyloxyalkyl, an alkoxyalkenyl, an alkynyl, and an alkynyloxy. In these groups, a linear group is more preferable than a branched group. Even if R is a branched group, when it is optically active is preferable. In the alkenyl, a preferred stereospecific configuration of —CH=CH— replies upon the position of a double bond. In the alkenyl having a double bond at an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$, a trans-configuration is preferable. In the alkenyl having a double bond at an even-numbered position, such as —CH$_2$CH=CHCH$_3$, —CH$_2$CH=CHC$_2$H$_5$, and —CH$_2$CH=CHC$_3$H$_7$, a cis-configuration is preferable.

Specific examples of the alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$, and —$C_{10}H_{21}$. Specific examples of the alkoxy include —$OCH_3$, —$OC_2H_5$, —$OC_3H_7$, —$OC_4H_9$, —$OC_5H_{11}$, —$OC_6H_{13}$, and —$OC_7H_{15}$. Specific examples of the alkoxyalkyl include —$CH_2OCH_3$, —$CH_2OC_2H_5$, —$CH_2OC_3H_7$, —$(CH_2)_2OCH_3$, —$(CH_2)_2OC_2H_5$, —$(CH_2)_2OC_3H_7$, —$(CH_2)_3OCH_3$, —$(CH_2)_4OCH_3$, and —$(CH_2)_5OCH_3$. Specific examples of the alkenyl include —CH=$CH_2$, —CH=CHCH$_3$, —$CH_2$CH=$CH_2$, —CH=CHC$_2$H$_5$, —$CH_2$CH=CHCH$_3$, —$(CH_2)_2$CH=$CH_2$, —CH=CHC$_3$H$_7$, —$CH_2$CH=CHC$_2$H$_5$, —$(CH_2)_2$CH=CHCH$_3$, and —$(CH_2)_3$CH=$CH_2$. Specific examples the alkenyloxy include —$OCH_2$CH=$CH_2$, —$OCH_2$CH=CHCH$_3$, and —$OCH_2$CH=CHC$_2$H$_5$. Specific examples of the alkynyl include —C≡CCH$_3$ and —C≡CC$_3$H$_7$.

Then, preferred examples of R include an alkyl having from 1 to 15 carbon atoms, an alkoxy having from 1 to 15 carbon atoms, an alkoxyalkyl having from 2 to 15 carbon atoms, and an alkenyl having from 2 to 15 carbon atoms. More preferred examples of R include an alkyl having from 1 to 7 carbon atoms, an alkoxy having from 1 to 4 carbon atoms, and an alkenyl having from 2 to 7 carbon atoms.

Specific examples of preferred R include —$CH_3$, —$C_2H_5$, —$C_3H_7$, —$C_4H_9$, —$C_5H_{11}$, —$C_6H_{13}$, —$OCH_3$, —$OC_2H_5$, —$OC_3H_7$, —$CH_2OCH_3$, —CH=$CH_2$, —CH=CHCH$_3$, —$(CH_2)_2$CH=$CH_2$, and —$(CH_2)_2$CH=CHCH$_3$.

In the formula (1), $A^1$, $A^2$, and $A^3$ each independently represents 1,4-cyclohexylene or 1,4-phenylene. In this 1,4-cyclohexylene, any —$CH_2$— may be replaced by —O—, —S—, or —CO—; and any —$(CH_2)_2$— may be replaced by —CH=CH—. In this 1,4-phenylene, any —CH= may be replaced by —N=. Preferred examples of the ring which falls within the range according to the foregoing definition include the following formulae (15-1) to (15-22). More preferred examples include the formulae (15-1) to (15-5), the formulae (15-14) to (15-18), and the formulae (15-21) and (15-22).

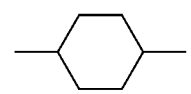

(15-1)

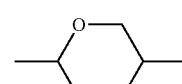

(15-2)

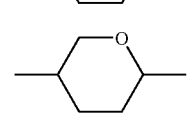

(15-3)

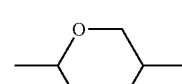

(15-4)

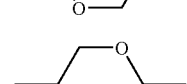

(15-5)

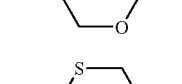

(15-6)

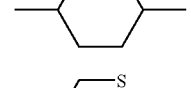

(15-7)

(15-8) 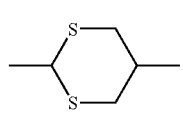

(15-9) 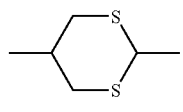

(15-10) 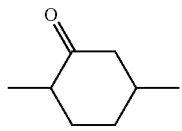

(15-11) 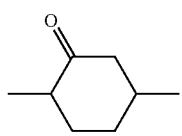

(15-12) 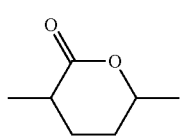

(15-13) 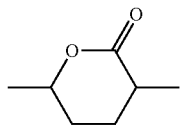

(15-14) 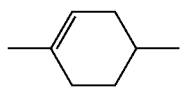

(15-15) 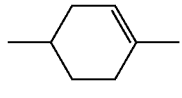

(15-16) 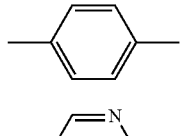

(15-17) 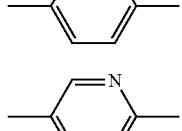

(15-18) 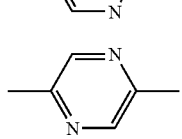

(15-19) 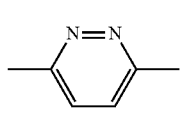

(15-20) 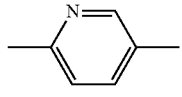

(15-21)

(15-22) 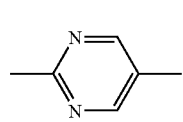

In the ring which falls within the range according to the foregoing definition, any hydrogen may be replaced by fluorine, chlorine, —CN, —CF$_3$, —CHF$_2$, —CH$_2$F, —OCF$_3$, —OCHF$_2$, or —OCH$_2$F. Preferred examples of the ring in which any hydrogen may be replaced by fluorine, chlorine, —CN, —CF$_3$, —CHF$_2$, —CH$_2$F, —OCF$_3$, —OCHF$_2$, or —OCH$_2$F include the following formulae (16-1) to (16-37). More preferred examples include the formulae (16-1) to (16-4), the formula (16-6), the formulae (16-10) to (16-14), and the formula (16-35).

(16-1) 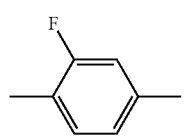

(16-2) 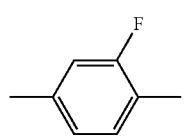

(16-3) 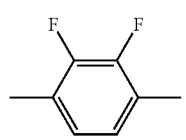

(16-4) 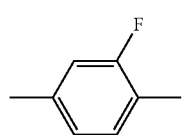

(16-5) 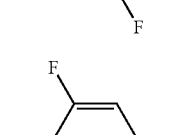

(16-6) 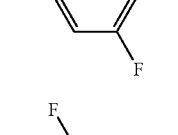

(16-7) 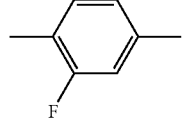

-continued
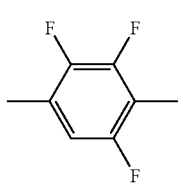 (16-8)
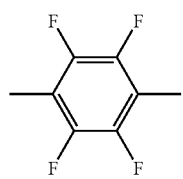 (16-9)
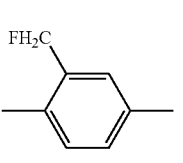 (16-10)
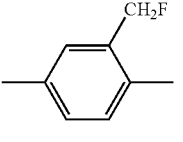 (16-11)
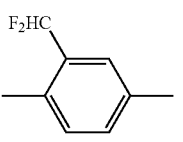 (16-12)
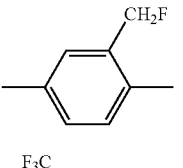 (16-13)
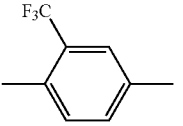 (16-14)
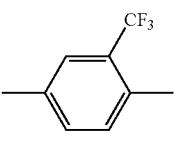 (16-15)
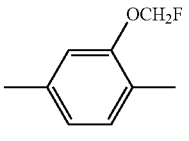 (16-16)
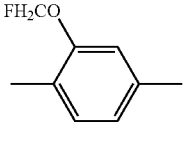 (16-17)
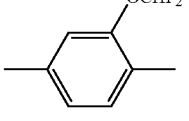 (16-18)
-continued
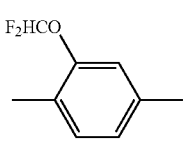 (16-19)
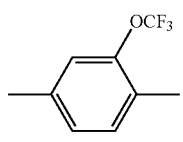 (16-20)
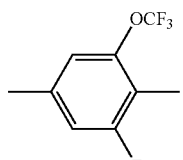 (16-21)
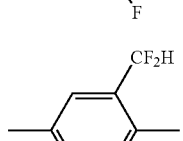 (16-22)
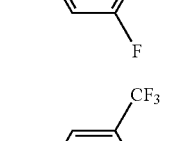 (16-23)
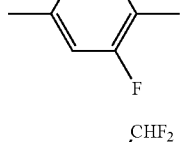 (16-24)
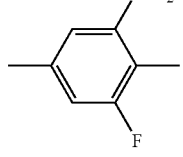 (16-25)
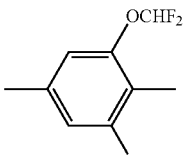 (16-26)
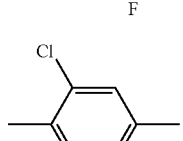 (16-27)
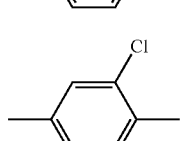 (16-28)
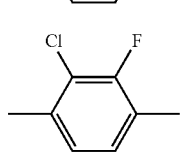

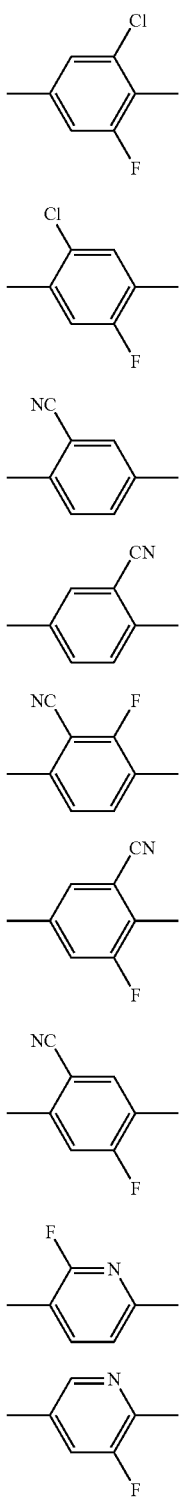

Preferred examples of $A^1$, $A^2$, and $A^3$ include 1,4-cyclohexylene, 1,4-cyclohexenylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoropyridine-2,5-diyl, pyrimidine-2,5-diyl, and pyridazine-2,5-diyl. With respect to the stereospecific configuration of 1,4-cyclohexylene and 1,3-dioxane-2,5-diyl, the trans-configuration is more preferable than the cis-configuration.

The most preferred examples of $A^1$, $A^2$, and $A^3$ include 1,4-cyclohexylene, 1,3-dioxane-2,5-diyl, 1,4-phenylene, 2-fluoro-1,4-phenylene, 2,5-difluoro-1,4-phenylene, 2,6-difluoro-1,4-phenylene, pyridine-2,5-diyl, and pyrimidine-2,5-diyl.

Incidentally, in the invention, a bilaterally asymmetrical divalent ring may be bound in the reverse direction in the formula (1).

In the formula (1), $Z^1$, $Z^2$, and $Z^3$ each represents a bonding group. These bonding groups each independently represents a single bond, —(CH$_2$)$_2$—, —CH$_2$O—, —OCH$_2$—, —CF$_2$O—, —OCF$_2$—, —CH=CH—, —CF=CF—, —C≡C—, —(CH$_2$)$_4$—, —O(CH$_2$)$_2$O—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—CH$_2$O—, or —OCH$_2$—CH=CH—. Of these, with respect to the stereospecific configuration regarding the double bond of the bonding group such as —CH=CH—, —CF=CF—, —CH=CH—CH$_2$O—, and —OCH$_2$—CH=CH—, the trans-configuration is more preferable than the cis-configuration.

Preferred examples of $Z^1$, $Z^2$, and $Z^3$ include a single bond, —(CH$_2$)$_2$—, —CH$_2$O—, —OCH$_2$—, —CF$_2$O—, —OCF$_2$—, and —CH=CH—.

In the formula (1), X represents hydrogen, fluorine, chlorine, —CN, —CF$_3$, —CHF$_2$, —CH$_2$F, —OCF$_3$, —OCHF$_2$, or —OCH$_2$F; G represents oxygen or sulfur; and n and m each independently represents 0, 1, or 2. It is preferable that the total sum of n and m is 0, 1, or 2.

In any one of the following (i) to (iii), R in the formula (1) may represent hydrogen:

(i) the total sum of n and m is 1 or 2;
(ii) X represents fluorine, chlorine, —CN, —CF$_3$, —CHF$_2$, —CH$_2$F, —OCF$_3$, —OCHF$_2$, or —OCH$_2$F; and
(iii) at least one of $A^1$, $A^2$, and $A^3$ represents 1,4-phenylene in which any hydrogen is replaced by fluorine, chlorine, —CN, —CF$_3$, —CHF$_2$, —CH$_2$F, —OCF$_3$, —OCHF$_2$, or —OCH$_2$F.

The compound (1) of the invention is further described below. When a fused ring is counted as one ring, the compound (1) is a compound having 2 to 6 rings. And the number of rings is preferably 2 to 4. This compound is extremely chemically and physically stable under a condition which a device is usually used, and is well compatible with other liquid crystalline compounds. A composition containing this compound is stable under a condition which a device is usually used. Even when this composition is stored at low temperatures, this compound is not deposited as a crystal (or a smectic phase). This compound has general physical properties necessary for a compound, adequate optical anisotropy and adequate dielectric anisotropy.

By adequately selecting a terminal group, a ring and a bonding group of the compound (1), it is possible to arbitrarily adjust physical properties such as optical anisotropy and dielectric anisotropy. Effects which kinds of the terminal group, the ring and the bonding group give to the physical properties of the compound (1) are described below.

In the compound (1), the dielectric anisotropy is positive and large. A compound having large dielectric anisotropy is useful as a component for lowering a threshold voltage of the composition.

When R is linear, the compound has a wide temperature range of the liquid crystal phase and a low viscosity. When R is branched, the compound is well compatible with other liquid crystalline compounds. A compound wherein R is an optically active group is useful as a chiral dopant. By adding this compound in the composition, it is possible to prevent a reverse twisted domain generated in the device. A compound wherein R is not an optically active group is useful as component of the composition. When R is an alkenyl, the preferred stereospecific configuration relies upon the position of the double bond. An alkenyl compound having the preferred stereospecific configuration has a high upper limit temperature or a wide temperature range of the liquid crystal phase. Details of such information are described in *Mol. Cryst. Liq. Cryst.*, 1985, 131, 109 and *Mol. Cryst. Liq. Cryst.*, 1985, 131, 327.

When the majority of rings are 1,4-phenylene, pyridine-2,5-diyl, or 1,3-dioxane-2,5-diyl in which any hydrogen is replaced by a halogen, there is a tendency that the dielectric anisotropy is large. When the majority of rings are 1,4-phenylene, pyridine-2,5-diyl, pyrimidine-2,5-diyl, or pyridazine-3,6-diyl in which any hydrogen may be replaced by a halogen, there is a tendency that the optical anisotropy is large. When the majority of rings are 1,4-cyclohexylene, 1,4-cylohexenylene, or 1,3-dioxane-2,5-diyl, there is a tendency that the optical anisotropy is small.

When at least two rings are 1,4-cyclohexylene, there is a tendency that the upper limit temperature is high, the optical anisotropy is small and that the viscosity is low. When at least one ring is 1,4-phenylene, there is a tendency that the optical anisotropy is relatively large and that the orientational order parameter is large. When at least two rings are 1,4-phenylene, there is a tendency that the optical anisotropy is large; that the temperature range of the liquid crystal phase is wide; and that the upper limit temperature is high.

When the majority of bonding groups is a single bond, —(CH$_2$)$_2$—, —CH$_2$O—, —CF$_2$O—, —OCF$_2$—, —CH═CH—, —CF═CF—, or —(CH$_2$)$_4$—, there is a tendency that the viscosity is low. When the majority of bonding groups is a single bond, —(CH$_2$)$_2$—, —OCF$_2$—, —CF$_2$O—, or —CH═CH—, there is a tendency that the viscosity becomes lower. When the bonding group contains —CH═CH—, there is a tendency that the temperature range of the liquid crystal phase is wide and that an elastic constant ratio K$_{33}$/K$_{11}$ (K$_{33}$: bend elastic constant, K$_{11}$: spray elastic constant) is large. When the bonding group contains —C≡C—, there is a tendency that the optical anisotropy is large.

When the compound (1) has two rings or three rings, there is a tendency that the viscosity is low. When the compound (1) has three rings or four rings, there is a tendency that the upper limit temperature is high. In the light of the above, by adequately selecting the kinds of the terminal group, the ring and the bonding group and the number of rings, it is possible to obtain a compound having the desired physical properties. Accordingly, the compound (1) is used as component of the composition which is used in devices such as PC, TN, STN, ECB, OCB, IPS, and VA devices.

Preferred examples of the compound (1) are the compounds (1-a) to (1-m) as set forth in the item [19] of the invention. More specific examples include the following compounds (1-1) to (1-45). In these compounds, R has the same meaning as the symbol as set forth in the item [2].

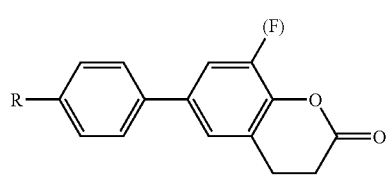

1-1

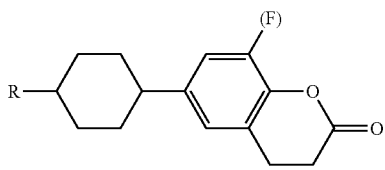

1-2

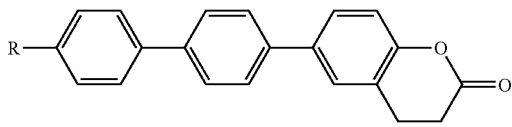

1-3

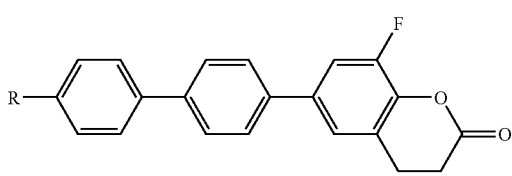

1-4

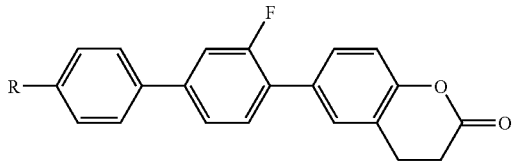

1-5

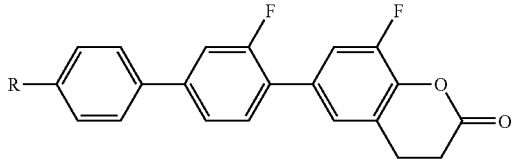

1-6

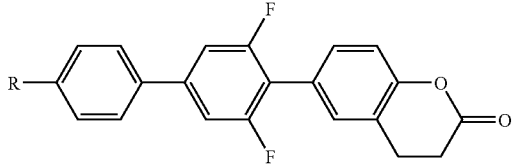

1-7

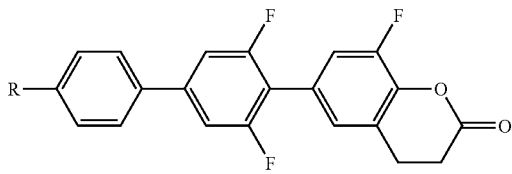

1-8

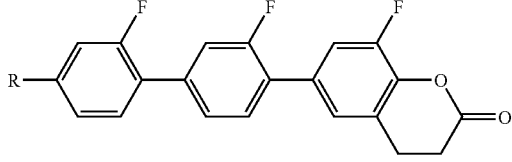

1-9

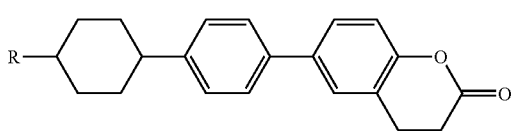

1-10

-continued
1-11
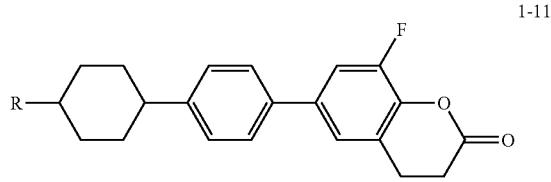
1-12
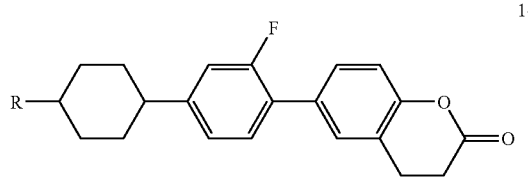
1-13
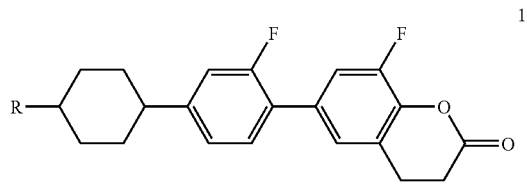
1-14
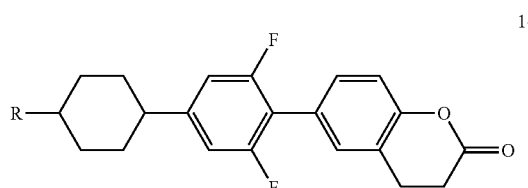
1-15
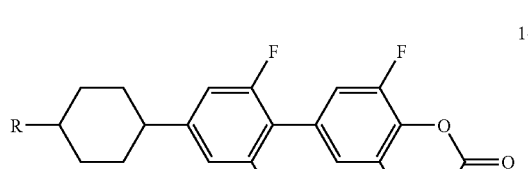
1-16
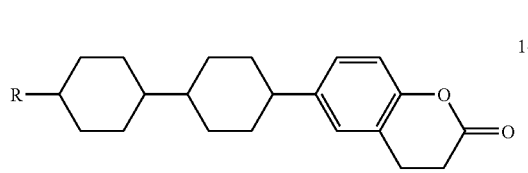
1-17
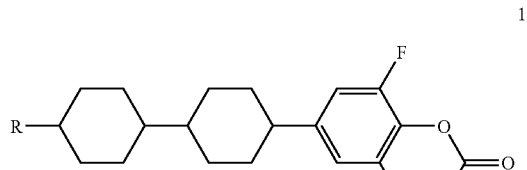
1-18
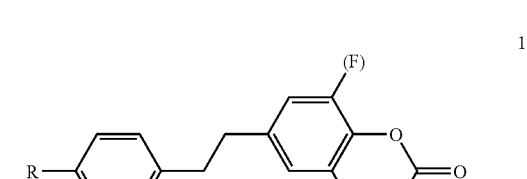
-continued
1-19
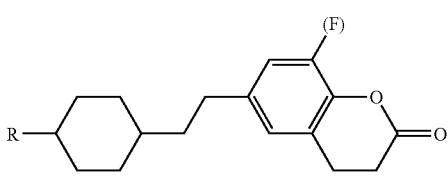
1-20
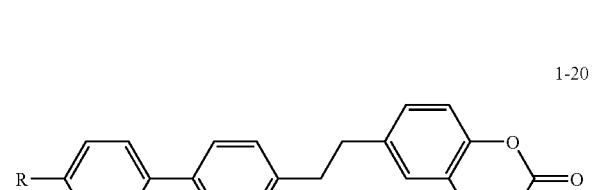
1-21
1-22
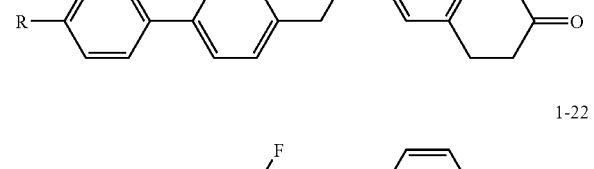
1-23
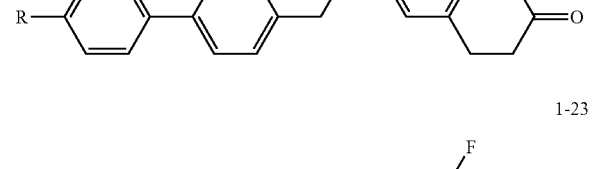
1-24
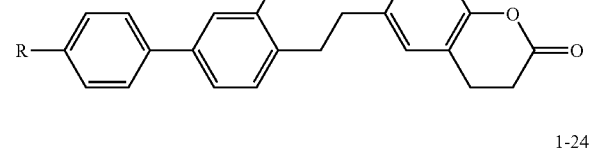
1-25
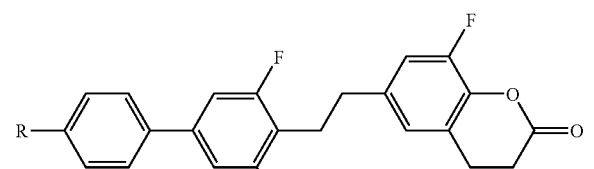

1-26
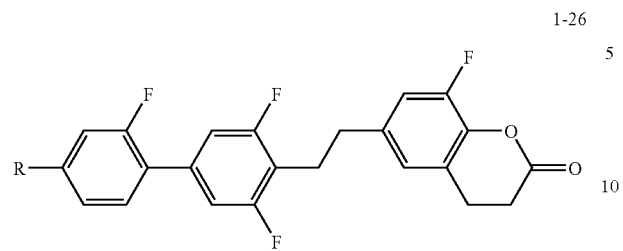
1-27
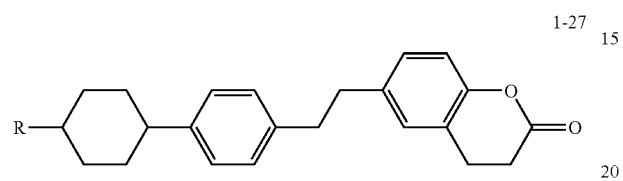
1-28
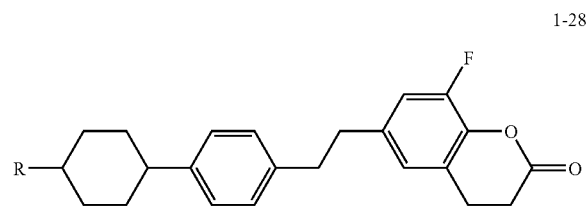
1-29
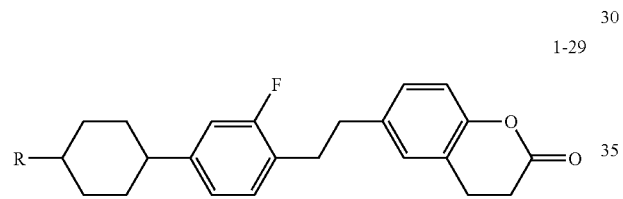
1-30
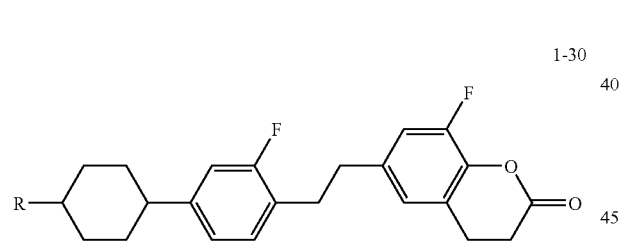
1-31
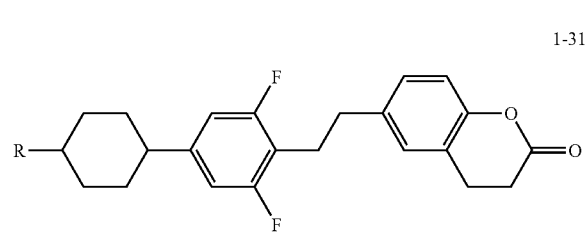
1-32
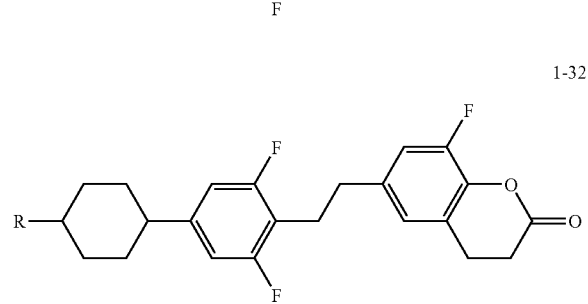
1-33
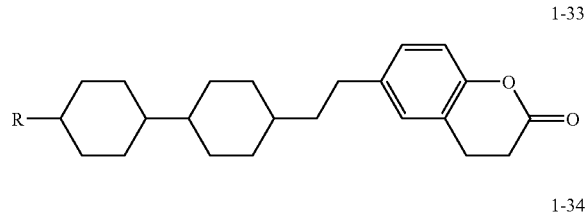
1-34
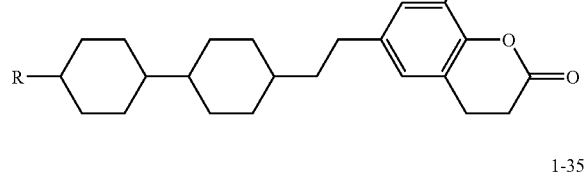
1-35
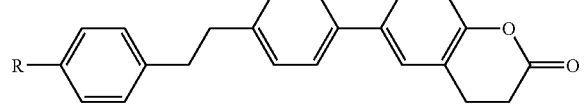
1-36
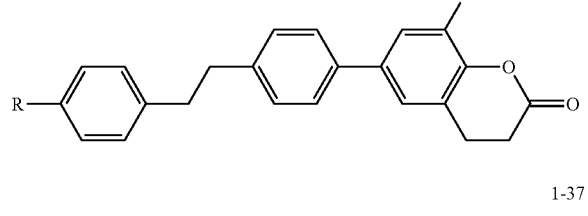
1-37
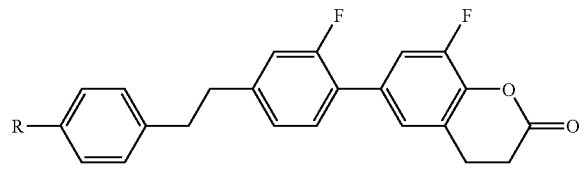
1-38
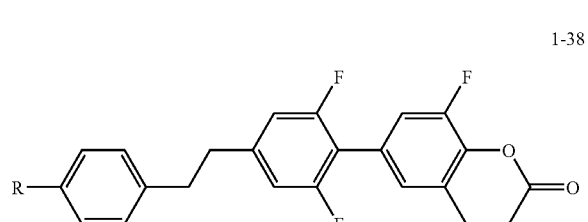
1-39
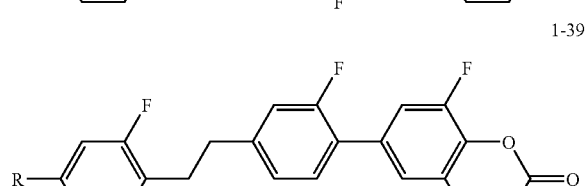
1-40
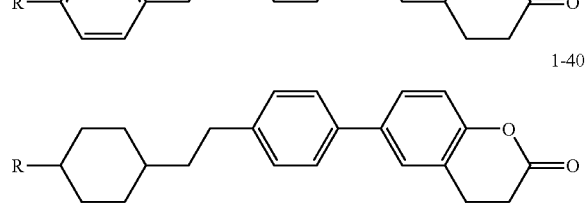

1-41
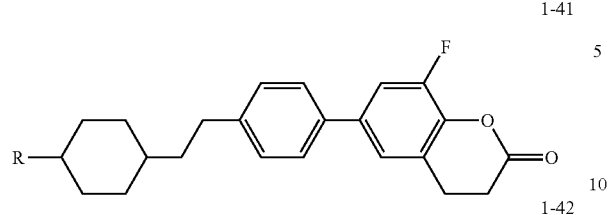
1-42
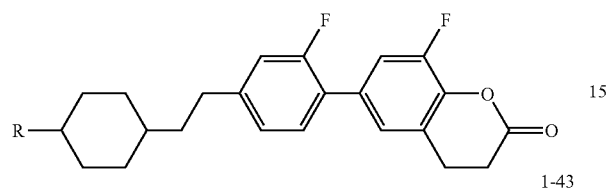
1-43
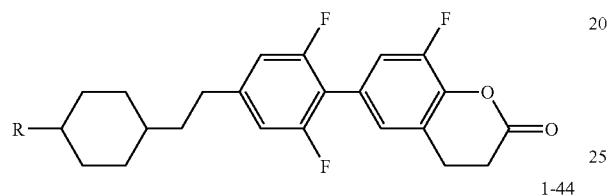
1-44
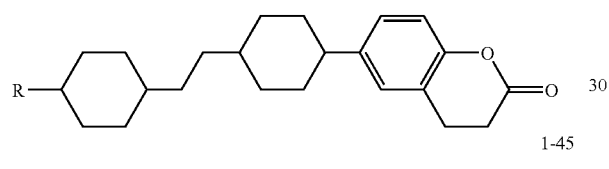
1-45
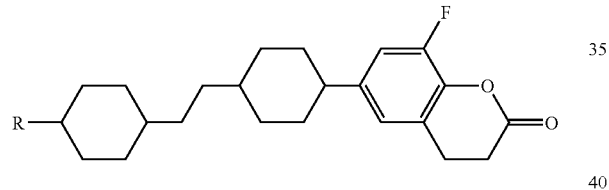
More preferred specific examples of the compound (1) include the following compounds.
1-5
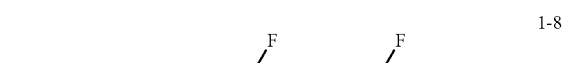
1-6
1-7
1-8
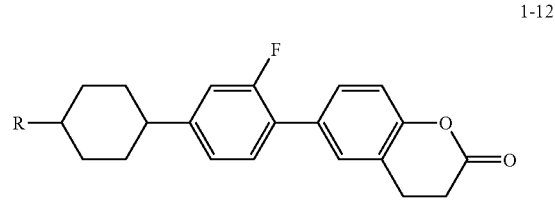
1-12
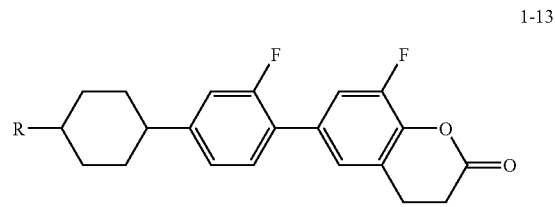
1-13
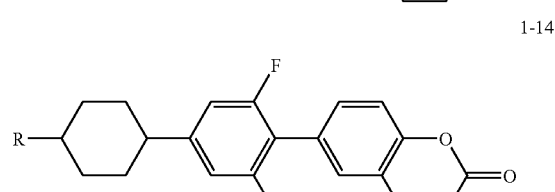
1-14
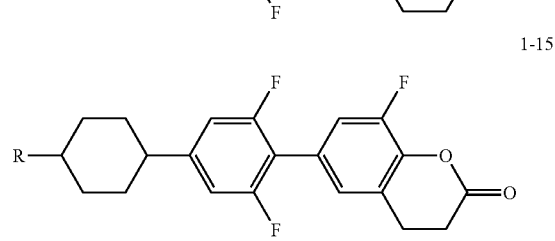
1-15
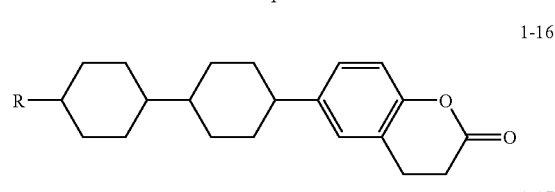
1-16
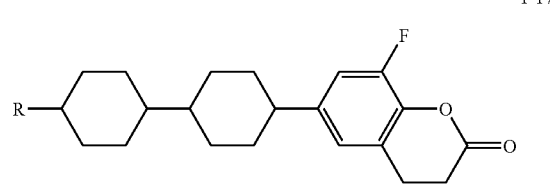
1-17
1-22
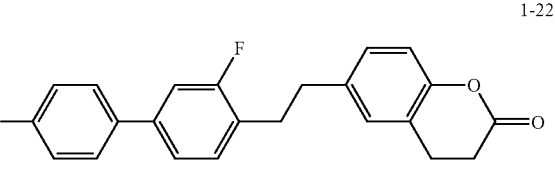

1-23

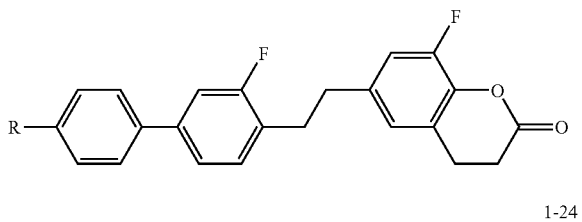

1-24

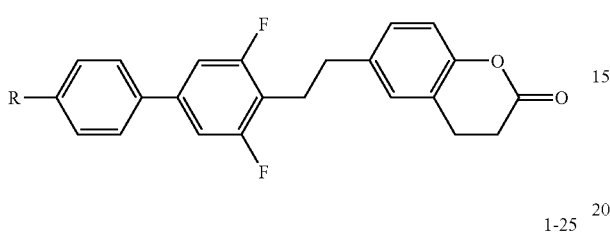

1-25

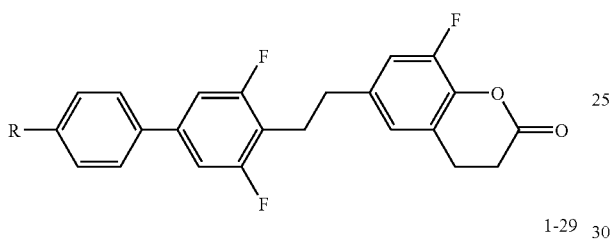

1-29

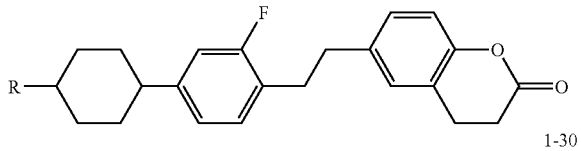

1-30

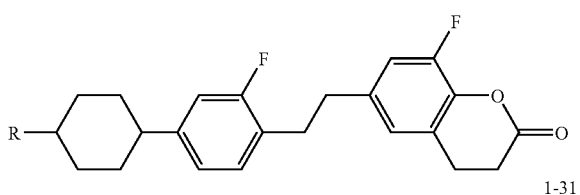

1-31

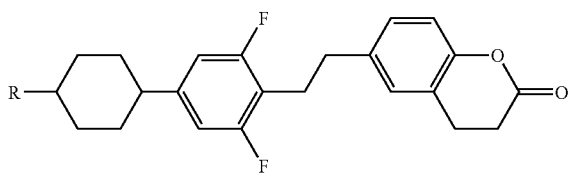

1-32

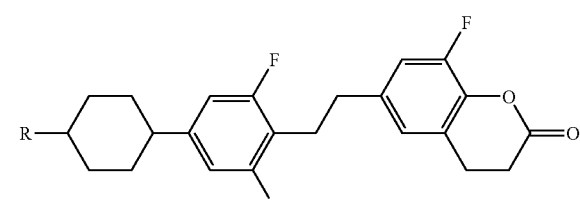

1-33

1-34

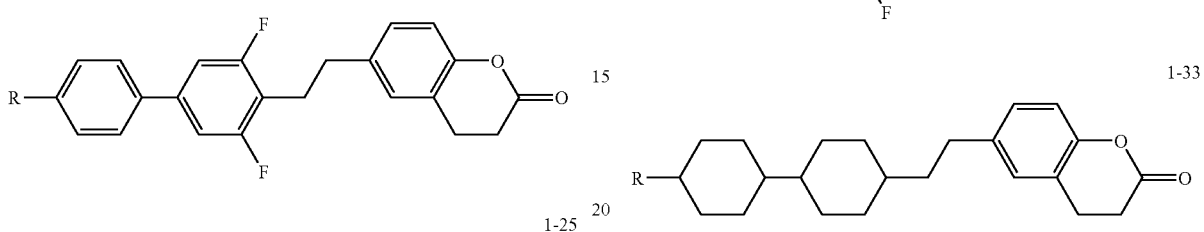

In these formulae, R represents an alkyl having from 1 to 7 carbon atoms, an alkoxy having from 1 to 4 carbon atoms, or an alkenyl having from 2 to 7 carbon atoms.

The compound (1) is synthesized by appropriately combining methods in the organic synthetic chemistry. A method for introducing the desired terminal group, ring and bonding group into the starting material is described in *Organic Syntheses*, John Wiley & Sons, Inc., *Organic Reactions*, John Wiley & Sons, Inc., *Comprehensive Organic Synthesis*, Pergamon Press, *Shin-Jikken Kagaku Koza* (New Experimental Chemistry Course), Maruzen, and the like.

With respect to examples of a method for forming the bonding group, a scheme is first shown, and the scheme is then described according to the following items (I) to (XI). In this scheme, $MSG^1$ or $MSG^2$ represents a monovalent organic group having at least one ring. Multiple $MSG^1$s (or $MSG^2$s) as used in the scheme may be the same or different. Compounds (1A) to (1K) are corresponding to the compound (1).

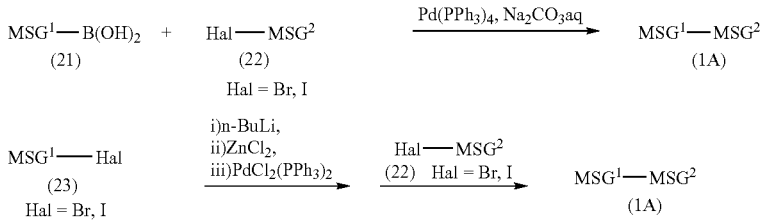

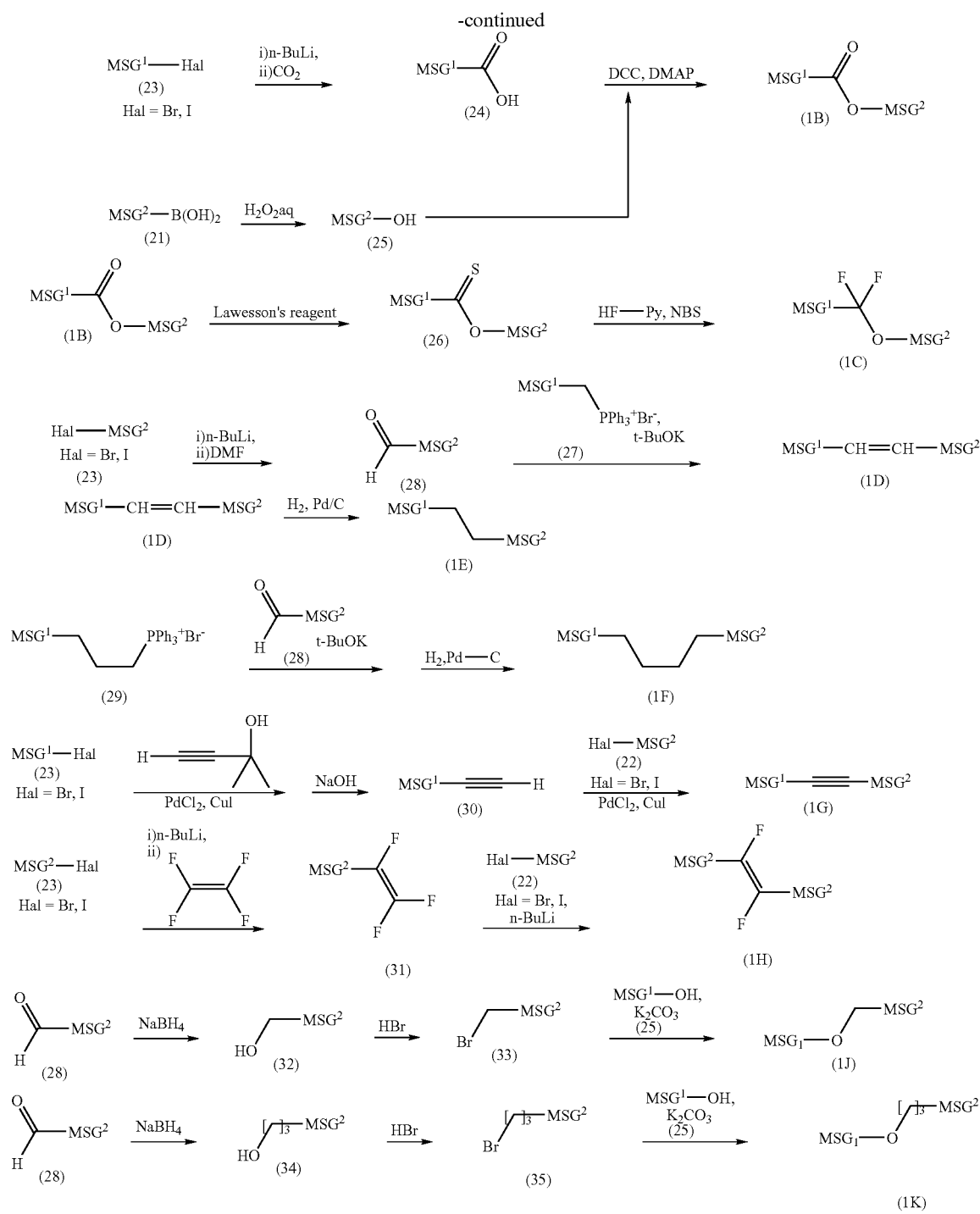

(I) Formation of Single Bond:

An aryl boric acid (21) is allowed to react with a compound (22) which is synthesized by a known method in the presence of a carbonate aqueous solution and a catalyst such as tetrakis(triphenylphosphine)palladium, thereby synthesizing a compound (1A). This compound (1A) is also synthesized by allowing a compound (23) which is synthesized by a known method to react with n-butyllithium, subsequently with zinc chloride, and further with the compound (22) in the presence of a catalyst such as dichlorobis(triphenylphosphine)palladium.

(II) Formation of —COO— and —OCO—:

The compound (23) is allowed to react with n-butyllithium and subsequently with carbon dioxide, thereby obtaining a carboxylic acid (24). The compound (24) and a phenol (25) which is synthesized by a known method are dehydrated in the presence of DCC (1,3-dicyclohexylcarbodimide) and DMAP (4-dimethylaminopyridine), thereby synthesizing a compound (1B) containing —COO—. A compound containing —OCO— is also synthesized by this method.

(III) Formation of —CF$_2$O— and —OCF$_2$—:

The compound (1B) is treated with a sulfurizing agent such as a Lawesson's reagent to obtain a compound (26). The compound (26) is fluorinated with a hydrogen fluoride pyridine complex and NBS (N-bromosuccimide) to synthesize a compound (1C) containing —CF$_2$O—. See M. Kuroboshi, et al., *Chem. Lett.*, 1992, 827. The compound (1C) is also synthesized by fluorinating the compound (26) with (diethylamino)sulfur trifluoride (DAST). See W. H. Bunnelle, et al., *J. Org. Chem.*, 1990, 55, 768. A compound containing —OCF$_2$— is also synthesized by this method. These bonding groups can also be formed by a method as described in Peer. Kirsch et al., *Anbew. Chem. Int. Ed.*, 2001, 40, 1480.

(IV) Formation of —CH=CH—:

The compound (23) is treated with n-butyllithium and then allowed to react with a formamide such as N,N-dimethylformamide (DMF), thereby obtaining an aldehyde (28). The aldehyde (28) is allowed to react with a phosphorus ylide generated by treating a phosphonium salt (27) which is synthesized by a known method with a base such as potassium tert-butoxide, thereby obtaining a compound (1D). Since a cis-isomer is formed depending upon the reaction condition, the cis-isomer is isomerized into a trans-isomer according to a known method, if desired.

(V) Formation of —(CH$_2$)$_2$—:

The compound (1D) is hydrogenated in the presence of a catalyst such as palladium-on-carbon to synthesize a compound (1E).

(VI) Formation of —(CH$_2$)$_4$—:

Using a phosphonium salt (29) in place of the phosphonium salt (27), a compound containing —(CH$_2$)$_2$—CH=CH— is obtained according to the method of the item (IV). This compound is catalytically hydrogenated to synthesize a compound (1F).

(VII) Formation of —C≡C—:

The compound (23) is allowed to react with 2-methyl-3-butyn-2-ol in the presence of a catalyst composed of dichloropalladium and a copper halide, followed by deprotection under a basic condition to obtain a compound (30). The compound (30) is allowed to react with the compound (22) in the presence of a catalyst composed of dichloropalladium and a copper halide, thereby synthesizing a compound (1G).

(VIII) Formation of —CF=CF—:

The compound (23) is treated with n-butyllithium and then allowed to react with tetrafluoroethylene, thereby obtaining a compound (31). The compound (22) is treated with n-butyllithium and then allowed to react with the compound (31), thereby synthesizing a compound (1H). (IX) Formation of —CH$_2$O— or —OCH$_2$—:

The compound (28) is reduced with a reducing agent such as sodium borohydride to obtain a compound (32). This compound (32) is halogenated with hydrobromic acid, etc. to obtain a compound (33). The compound (33) is allowed to react with the compound (25) in the presence of potassium carbonate, etc., thereby synthesizing a compound (1J).

(X) Formation of —(CH$_2$)$_3$O— or —O(CH$_2$)$_3$—:

Using a compound (34) in place of the compound (32), a compound (1K) is synthesized according to the method of the item (IX).

(XI) Formation of —(CF$_2$)$_2$—:

A diketone (—COCO—) is fluorinated with sulfur tetrafluoride in the presence of a hydrogen fluoride catalyst according to a method as described in *J. Am. Chem. Soc.*, 2001, 123, 5414, thereby obtaining a compound containing —(CF$_2$)$_2$—.

Next, specific examples of a method for synthesizing the dihydrocoumarin compound represented by the formula (1) are shown in the following schemes. First of all, one example of a method for synthesizing the dihydrocoumarin compound (1) using, as a starting substance, a synthetic intermediate (36) having a fluorophenol moiety is mentioned.

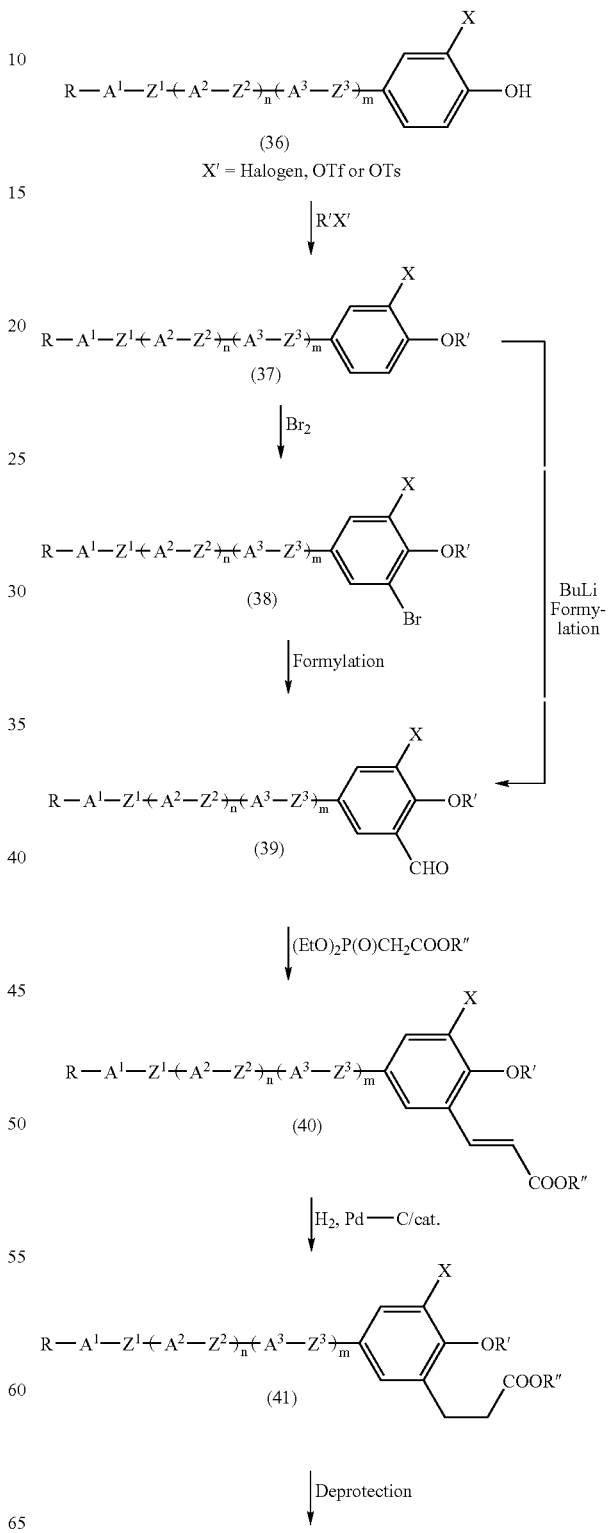

-continued

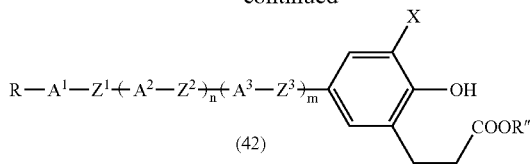
(42)

↓ pTosOH

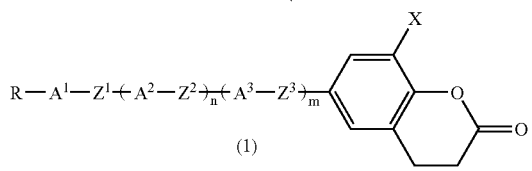
(1)

R'=Me, i-Pro, t-Bu, Benzyl, Benzoyl, Alloc, Troc, TMS, TBDMS Tips etc.,

R''=alkyl

In the above-described respective schemes, the meanings of symbols R, $A^1$, $A^2$, $A^3$, $Z^1$, $Z^2$, and $Z^3$ in these compounds are the same as in the symbols as set forth in the item [1]. The meanings of R' and R'' are shown in the schemes. The fluorophenol as the starting substance is synthesized by a method as described in DE4137401A1, etc. A compound (37) is obtained by allowing a compound (36) to react with a halide (R'X) and a base. Since R' is used as a protective group, ones which can be properly removed in later operations are selected and used. With respect to specific kinds of the protective group, the reaction condition, and the like, ones from methods as described in *Protective Groups in Organic Synthesis* 3rd ed., T. W. Green and P. G. M. Wuts, John Wiley & Sons, New York, N.Y. (1999) or other literatures are properly selected and used. A bromide (38) is synthesized by reaction of the compound (37) with bromine. Such a reaction is preferably carried out in the absence of a solvent or in a halide solvent such as methylene chloride, chloroform, and carbon tetrachloride at a temperature of from −80° C. to the boiling point of the solvent. The resulting compound (38) is treated with a base such as butyllithium and potassium hydride in an aprotic polar solvent such as THF and then allowed to react with a formylating agent such as dimethylformamide and N-formylpiperidine, thereby obtaining a benzaldehyde derivative (39). Alternatively, the compound (39) can also be synthesized directly without forming the compound (38) by treating the compound (37) with a base such as butyllithium in a solvent such as THF and dimethyl ether in a temperature region of from −100° C. to room temperature and then allowed to react with a formylating agent such as dimethylformamide and N-formylpiperidine in a temperature region of from −100° C. to room temperature. The resulting compound (39) can be converted into a cinnamic acid ester derivative (40) by allowing it to react with triethyl phosphonoacetate and a reagent such as sodium hydride, potassium tert-butoxide, and potassium hydroxide in a solvent such as THF and diethyl ether according to a method as described in B. E. Maryanoff, et al., *Chem. Rev.*, 89, 863 (1989) or other literatures. The compound (40) is converted into a phenylpropionic acid ester (41) by hydrogenation with a hydrogen gas in the presence of a heterogeneous catalyst for catalytic hydrogenation reaction such as palladium-on-carbon, platinum-on-carbon, and rhodium-on-carbon. On this occasion, a solvent to be used is preferably water, ethanol, toluene, acetic acid, etc., and hydrogen is provided for the reaction under a pressurizing condition, if desired. The resulting compound (41) is converted into a compound (42) by the removal of the protective group R' having been introduced at the initial stage of the scheme. In this case, the removal condition follows those described in *Protective Groups in Organic Synthesis* 3rd ed., T. W. Green and P. G. M. Wuts, John Wiley & Sons, New York, N.Y. (1999) or other literatures. The compound (42) is converted into the desired compound (1) by cyclization under reflux in a non-polar solvent such as toluene in the presence of an acid catalyst such as p-toluenesulfonic acid and sulfuric acid.

The compound (1) can also be synthesized by the following method.

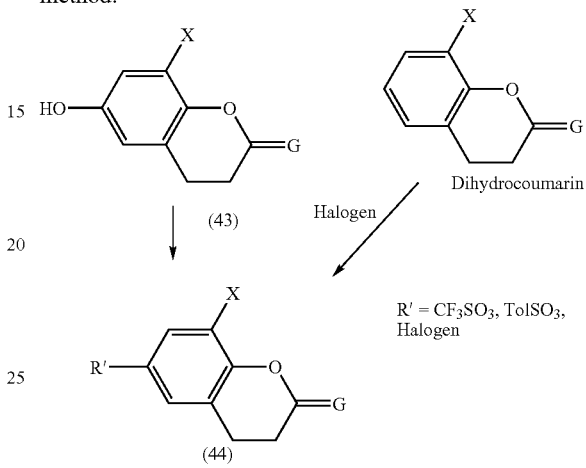
(43)            Dihydrocoumarin
            Halogen

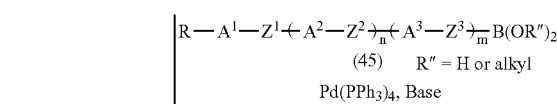
(44)

R' = CF$_3$SO$_3$, TolSO$_3$, Halogen $$R-A^1-Z^1(A^2-Z^2)_n(A^3-Z^3)_m B(OR'')_2$$
(45)    R'' = H or alkyl Pd(PPh$_3$)$_4$, Base

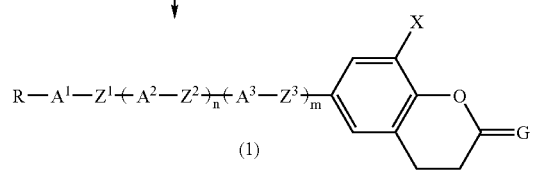
(1)

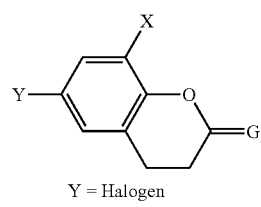
Y = Halogen
(44)

1. BuLi
2. ZnY$_2$

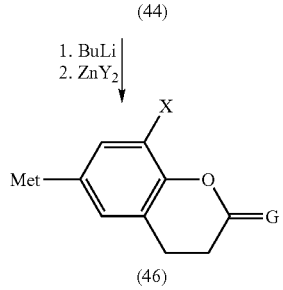
(46)
Met = MgY, ZnY, Li

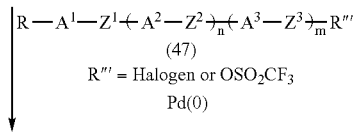
(47)
R''' = Halogen or OSO$_2$CF$_3$
Pd(0)

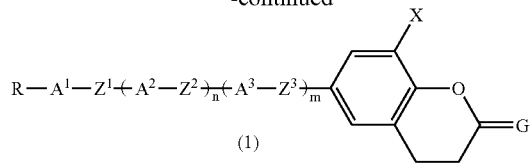

(1)

(I) A compound wherein n is 0, m is 0, $Z^1$ is a single bond, and $A^1$ is 1,4-phenylene; a compound wherein n is 1, m is 0, $Z^2$ is a single bond, and $A^2$ is 1,4-phenylene; or a compound wherein n is 1, m is 1, $Z^3$ is a single bond, and $A^2$ is 1,4-phenylene:

A compound (44) wherein R' is a halogen is synthesized by allowing a dihydrocoumarin to react directly with bromine or with iodine in the presence of an oxidizing agent. Such a reaction is preferably carried out in the absence of a solvent or in a solvent such as methylene chloride and chloroform at a temperature in the range of from −75° C. to the boiling point of the solvent. A compound (44) wherein R' is trifluoromethanesulfonyl or toluenesulfonyl is synthesized by allowing a compound (43) as described later to react with a sulfonylating agent such as trifluoromethanesulfonyl chloride, trifluoromethanesulfonic anhydride, and toluenesulfonyl chloride. Such a reaction is preferably carried out in the absence of a solvent or in a solvent such as methylene chloride and chloroform at a temperature in the range of from −75° C. to the boiling point of the solvent. A compound (I) is synthesized by allowing the compound (43) to react with a boric acid ester compound (45). Such a reaction is preferably carried out in a solvent such as an aromatic hydrocarbon (for example, toluene), an alcoholic hydrocarbon (for example, ethanol), an ether based hydrocarbon (for example, ethylene glycol dimethyl ether), and a mixed solution of such a solvent and water in the presence of a base such as potassium carbonate and sodium carbonate using a metal catalyst at a temperature of from room temperature to the boiling point of the solvent. Examples of the metal catalyst which is used include tetrakis (triphenylphosphine)palladium, dichloro-bis(triphenylphosphine)palladium, and palladium-on-carbon.

Alternatively, the compound (1) can also be synthesized by the following method. That is, the compound (44) is allowed to react with magnesium flake, metallic lithium, zinc powder, etc. or treated with butyllithium in a solvent such as THF, following by adding a zinc halide solution to prepare a solution of a compound (46). This solution of the compound (46) is allowed to react with a compound (47) in a solvent such as THF, diethyl ether, and dioxane in the presence of a metal catalyst such as tetrakistriphenylphosphine-palladium and dichlorodiphenylphosphinoferrocene-palladium. Thus, the compound (1) can be synthesized.

(II) A compound wherein n is 0, m is 0, and $Z^1$ is —$(CH_2)_2$—; a compound wherein n is 1, m is 0, and $Z^2$ is —$(CH_2)_2$—; or a compound wherein n is 1, m is 1, and $Z^3$ is —$(CH_2)_2$—:

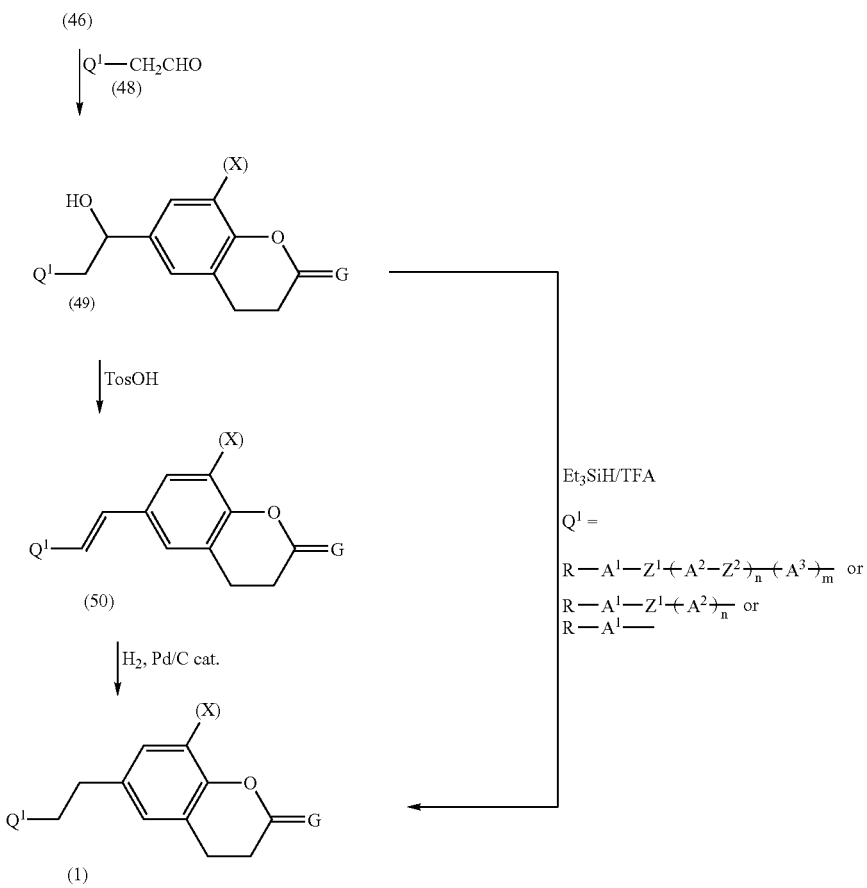

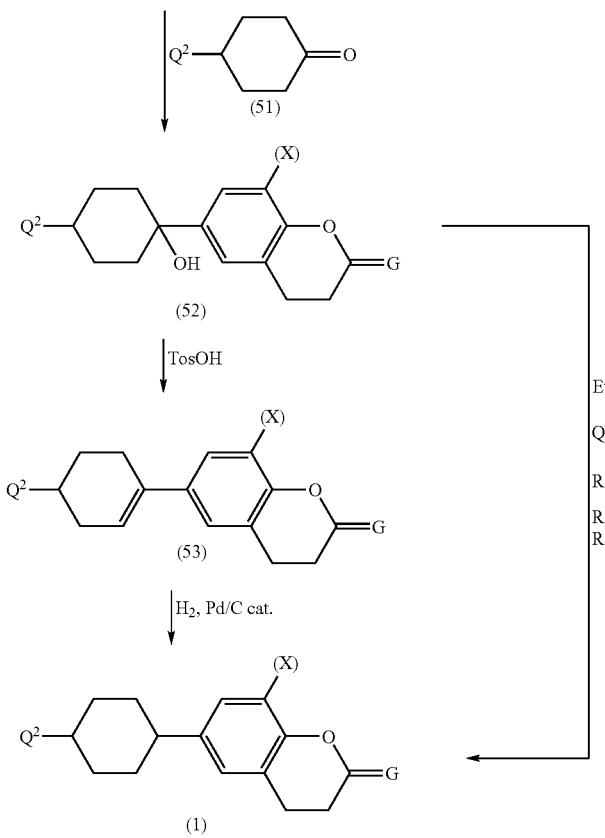

A compound (49) is synthesized by allowing the compound (46) to react with an aldehyde (48). Such a reaction is preferably carried out in a solvent such as tetrahydrofuran at a temperature of from −100° C. to the boiling point of the solvent. A compound (50) is synthesized by dehydrating the compound (49) using an acid such as p-toluenesulfonic acid and sulfuric acid. Such a reaction is preferably carried out in a solvent such as toluene at a temperature of from room temperature to the boiling point of the solvent. The compound (1) is synthesized by hydrogenating the compound (48) using a catalyst such as Raney nickel and palladium-on-carbon. Such a reaction is preferably carried out in a solvent such as an alcoholic hydrocarbon (for example, methanol and ethanol), an aromatic hydrocarbon (for example, toluene), an aliphatic hydrocarbon (for example, heptane), and a mixed solution thereof at a temperature of from room temperature to the boiling point of the solvent. The hydrogen pressure is preferably from the atmospheric pressure to 10 atms.

The compound (1) can also be synthesized by allowing the compound (47) to react with a hydrosilane such as triethylsilane in a trifluoroacetic acid solvent or in methylene chloride in the presence of titanium tetrachloride. In this reaction, the reaction temperature is preferably from about −50° C. to room temperature.

(III) A compound wherein n is 0, m is 0, $Z^1$ is a single bond, and $A^1$ is 1,4-cyclohexylene; a compound wherein n is 1, m is 0, $Z^2$ is a single bond, and $A^2$ is 1,4-cyclohexylene; or a compound wherein n is 1, m is 1, $Z^3$ is a single bond, and $A^2$ is 1,4-cyclohexylene:

The compound (50) is synthesized by allowing the compound (46) to react with a cyclohexanone (51). Such a reaction is preferably carried out in a solvent such as tetrahydrofuran at a temperature of from −100° C. to the boiling point of the solvent. A compound (52) is synthesized by dehydrating the compound (51) using an acid such as p-toluenesulfonic acid and sulfuric acid. Such a reaction is preferably carried out in a solvent such as toluene at a temperature of from room temperature to the boiling point of the solvent. The compound (1) is synthesized by hydrogenating a compound (53) using a catalyst such as Raney nickel and palladium-on-carbon. Such a reaction is preferably carried out in a solvent such as an alcoholic hydrocarbon (for example, methanol and ethanol), an aromatic hydrocarbon (for example, toluene), an aliphatic hydrocarbon (for example, heptane), and a mixed solution thereof at a temperature of from room temperature to the boiling point of the solvent. The hydrogen pressure is preferably from the atmospheric pressure to 10 atms. After the hydrogenation, though the compound (1) is obtained as an isomer mixture of a cis-isomer and a trans-isomer thereof, the trans-isomer can be obtained as the principal component by recrystallization. Alternatively, the compound (1) can also be synthesized by allowing the compound (52) to react with a hydrosilane such as triethylsilane in a trifluoroacetic acid solvent or in methylene chloride in the presence of titanium tetrachloride. In this reaction, the reaction temperature is preferably from about −50° C. to room temperature.

(IV) A compound wherein R is an alkenyl:

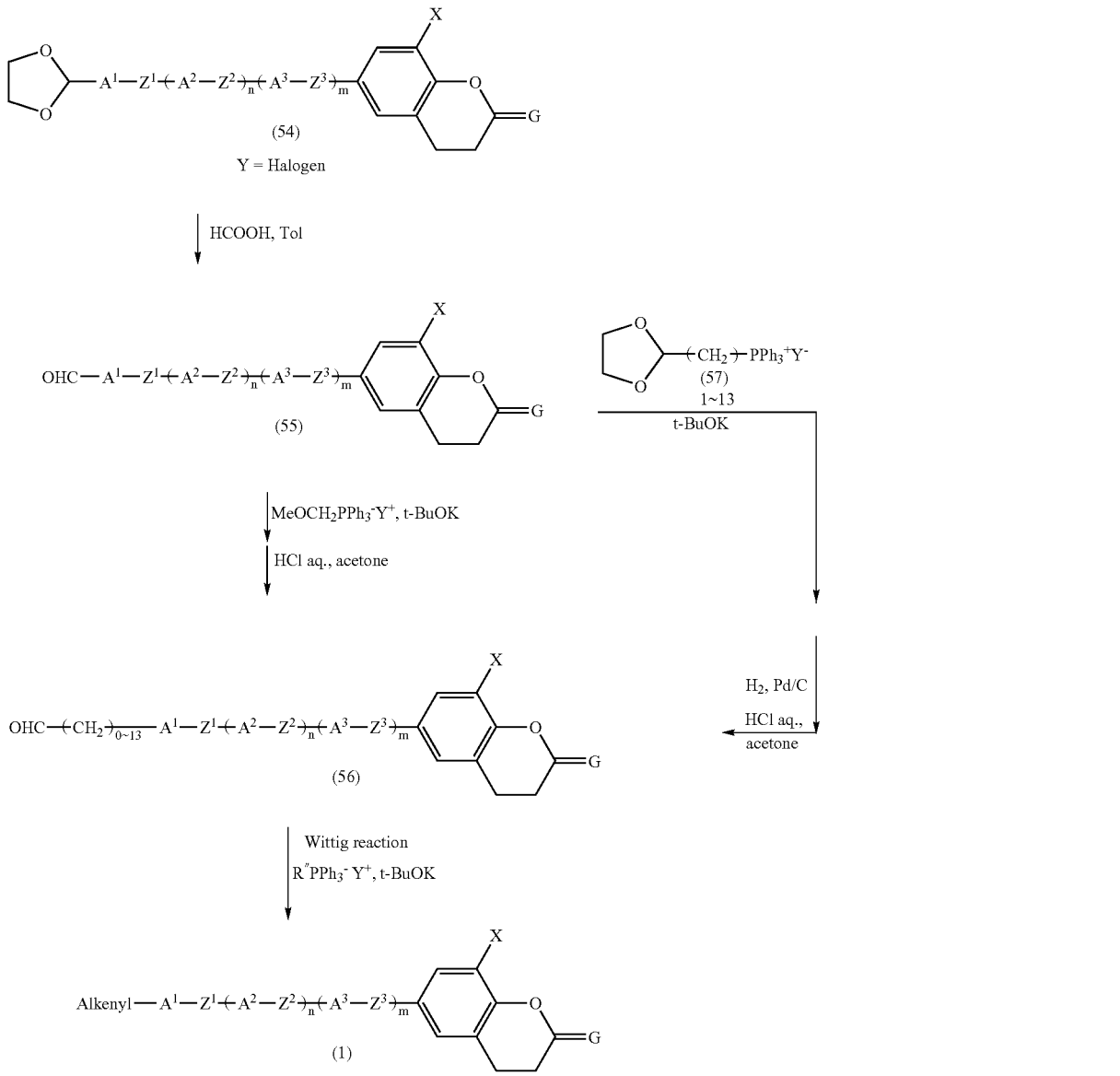

A compound (54) which is synthesized by any one of the methods as described previously is subjected to cleavage of a ketal in the presence of an acid catalyst to obtain a compound (55). The compound (55) is allowed to react with methoxymethylidene triphenylphosphorane to form a methyl vinyl ether, which is then deprotected under an acidic condition with dilute hydrochloric acid, etc., thereby obtaining an aldehyde (56) resulting from extension of the compound (55) by one carbon. This method is repeated necessary times to form the compound (56) which is a synthesis intermediate having a desired carbon chain. This compound (56) is then allowed to react with an alkylidene triphenylphosphorane having a desired chain length, thereby obtaining the compound (1). Such a reaction is preferably carried out in a solvent such as tetrahydrofuran at a temperature of from −75° C. to the boiling point of the solvent. Though the compound (1) is usually obtained as a mixture of stereo isomers, only a desired stereo isomer can be isolated by isomerization using benzenesulfinic acid, iodine, etc. or recrystallization, if desired. Furthermore, the compound (1) can also be produced by allowing the compound (55) to react with an alkylidene phosphorane which is generated by allowing a phosphonium salt for extension of the carbon chain as represented by the formula (57) to react with a base such as potassium tert-butoxide, sodium hydride, and butyllithium and hydrogenating a generated intermediate, which is then subjected to cleavage of a ketal by processing with an acid to synthesize the compound (56), and allowing the compound (56) to react with an alkylidene phosphorane generated from an alkyltriphenyl phosphonium salt. In this case, though the compound (1) is usually obtained as a mixture of stereo isomers, too, only a desired stereo isomer can be isolated by isomerization using benzenesulfinic acid, iodine, etc. or recrystallization, if desired.

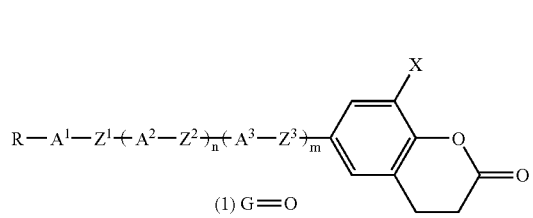

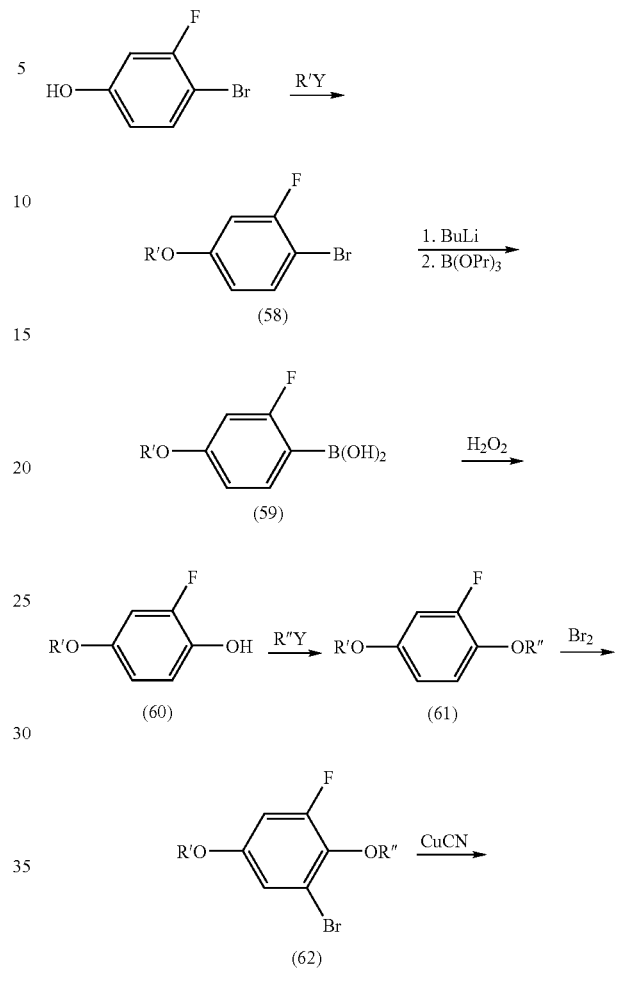

(V) Compound (1) wherein G is sulfur:

A compound (1) wherein G is sulfur is obtained by converting oxygen of a compound (1) wherein G is oxygen into sulfur using a Lowesson's reagent, etc. This reaction is preferably carried out in a solvent such as an aromatic hydrocarbon (for example, toluene, xylene, and mesitylene) in a temperature region of from room temperature to the boiling point of the solvent. As the need arises, the reaction can also be carried out in a pressure unit such as a sealed tube and an autoclave.

(VI) Compound (1) wherein X is fluorine:

A compound (1) wherein X is fluorine can be synthesizing by directly fluorinating a compound (1) wherein X is hydrogen using an MEC reagent, a fluorinating agent such as $(PhSO_2)NF$, etc. This is carried out in the presence of a solvent such as methylene chloride and THF in a temperature region of from $-100°$ C. to the boiling point of the solvent.

(VII) Synthesis of compound (44) wherein X is fluorine:

The foregoing compound (44) which is a synthesis intermediate is synthesized by, for example, the following synthesis scheme.

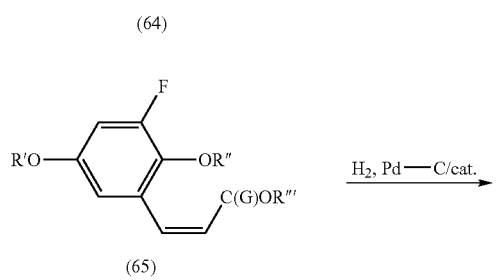

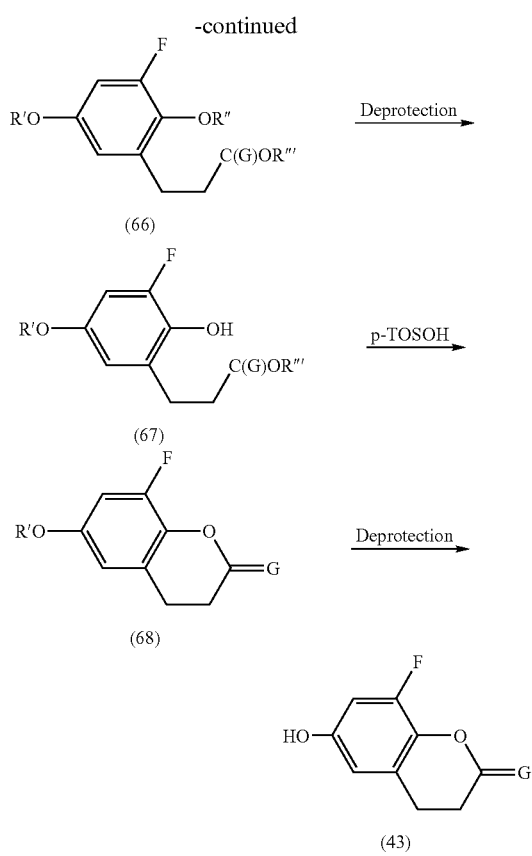

R' = Me, i-Pro, t-Bu Benzyl, Benzoyl, Alloc, Troc, TMS, TBDMS Tips etc.
R" = Me, i-Pro, t-Bu, Benzyl, Benzoyl, Alloc, Troc, TMS, TBDMS Tips etc.,
R''' = alkyl That is, commercially available 3-fluoro-4-bromophenol is allowed to react with a protecting reagent such as a trialkysilyl chloride in a solvent such as methylene chloride in the presence of an appropriate base such as an imidazole, thereby protecting a hydroxyl group by a trialkylsilyl group to form a compound (58). This compound (58) is converted into a metal reagent using butyllithium, etc. and then converted into a boric acid ester derivative (59) using a trialkyl borate, etc. This reaction is carried out in a solvent such as THF and diethyl ether in a temperature region of from −100° C. to the boiling point of the solvent. The resulting compound (59) is converted into a compound (60) by allowing it to react with hydrogen peroxide under basic condition. This reaction is usually carried out in a sodium hydroxide aqueous solution. The resulting compound (60) is protected by an appropriate protective group (for example, a benzyl group and a benzoyl group) as described in Protective Groups in Organic Synthesis 3rd ed., T. W. Green and P. G. M. Wuts, John Wiley & Sons, New York, N.Y. (1999), thereby forming a compound (61). The compound (61) is further converted into a compound (62) by brominating it with bromine in the absence of a solvent or a solvent such as methylene chloride. The compound (62) is converted into a compound (63) by cyanation using a cyanating reagent such as copper cyanide in a solvent such as DMF and NMP and then reduced into an aldehyde (64) using a reducing agent such as DIBAL. The compound (64) is further converted into a cinnamic acid ester (65) using triethyl phosphonoacetate and a base such as sodium hydride. A compound (66) is synthesized by hydrogenating the compound (65) using a catalyst such as Raney nickel and palladium-on-carbon. Such a reaction is preferably carried out in a solvent such as an alcoholic hydrocarbon (for example, methanol and ethanol), an aromatic hydrocarbon (for example, toluene), an aliphatic hydrocarbon (for example, heptane), and a mixed solution thereof at a temperature of from room temperature to the boiling point of the solvent. A compound (67) is allowed to react by applying a condition under which R" can be removed while retaining R'. For example, in the case where R' is a trimethylsilyl group and R" is a benzyl group, only the benzyl group can be removed depending upon the hydrogenation condition. A compound (68) is obtained by treating the compound (67) with an acid such as toluenesulfonic acid. The compound (43) is obtained by removing the R' group of the compound (68) by a method as described in Protective Groups in Organic Synthesis 3rd ed., T. W. Green and P. G. M. Wuts, John Wiley & Sons, New York, N.Y. (1999).

The composition of the invention is further described below. The components of this composition may be composed of only multiple compounds selected from the compound (1). A preferred composition contains at least one compound selected from the compound (1) in a proportion of from 1 to 99%. This composition mainly contains a component selected from the group consisting of the compounds (2) to (14). At the time of preparing the composition, the components are selected while taking into consideration the dielectric anisotropy of the compound (1).

A preferred composition containing the compound (1) in which the dielectric anisotropy is positive and large is as follows. This preferred composition contains at least one compound selected from the group consisting of the compound (2), the compound (3) and the compound (4). Another preferred composition contains at least one compound selected from the group consisting of the compound (5) and the compound (6). A still another preferred composition contains at least two compounds selected from the foregoing respective two groups. For the purpose of adjusting the temperature range of the liquid crystal phase, the viscosity, the optical anisotropy, the dielectric anisotropy, the threshold voltage, and the like, such a composition may further contain at least one compound selected from the group consisting of the compound (12), the compound (13) and the compound (14). For the purpose of further adjusting the physical properties, such a composition may further contain at least one compound selected from the group of the compounds (7) to (11). For the purpose of adapting to an AM-TN device, an STN device, etc., such a composition may further contain a compound such as other liquid crystalline compounds and additives.

An even another preferred composition contains at least one compound selected from the group consisting of the compounds (12) to (14). For the purpose of further adjusting the physical properties, this composition may further contain at least one compound selected from the group consisting of the compounds (7) to (11). For the purpose of adapting to an AM-TN device, an STN device, etc., this composition may further contain a compound such as other liquid crystalline compounds and additives.

A preferred composition containing the compound (1) in which the dielectric anisotropy is small is as follows. This preferred composition contains at least one compound selected from the group consisting of the compounds (2) to (4). Another preferred composition contains at least one compound selected from the group consisting of the compound (5) and the compound (6). A still another preferred composition contains at least two compounds selected from the foregoing respective two groups. For the purpose of adjusting the temperature range of the liquid crystal phase, the viscosity, the optical anisotropy, the dielectric anisotropy, the threshold voltage, and the like, such a composition may further contain at least one compound selected from the group consisting of the compounds (12) to (14). For the purpose of further adjusting the physical properties, such a composition may further contain at least one compound selected fro the group of the compounds (7) to (11). For the purpose of adapting to an AM-TN device, an STN device, etc., such a composition may further contain a compound such as other liquid crystalline compounds and additives.

An even another preferred composition contains at least one compound selected from the group consisting of the compounds (7) to (11). This composition may further contain at least one compound selected from the group consisting of the compounds (12) to (14). For the purpose of further adjusting the physical properties, this composition may further contain at least one compound selected from the group consisting of the compounds (2) to (6). For the purpose of adapting to a VA device, etc., this composition may further contain a compound such as other liquid crystalline compounds and additives.

In the compounds (2) to (4), since the dielectric anisotropy is positive and large, these compounds are used mainly in a composition for an AM-TN device. In this composition, the amount of such a compound is from 1 to 99%, preferably from 10 to 97%, and more preferably from 40 to 95%. In the case of further adding the compound (12), (13) or (14) in this composition, the amount of this compound is preferably not more than 60%, and more preferably not more than 40%.

In the compounds (5) and (6), since the dielectric anisotropy is positive and very large, these compounds are used mainly in a composition for an STN device. In this composition, the amount of such a compound is from 1 to 99%, preferably from 10 to 97%, and more preferably from 40 to 95%. In the case of further adding the compound (12), (13) or (14) in this composition, the amount of this compound is preferably not more than 60%, and more preferably not more than 40%.

In the compounds (7) to (11), since the dielectric anisotropy is negative, these compounds are used mainly in a composition for a VA device. The amount of such a compound is preferably not more than 80%, and more preferably from 40 to 80%. In the case of further adding the compound (12), (13) or (14) in this composition, the amount of this compound is preferably not more than 60%, and more preferably not more than 40%.

In the compounds (12) to (14), the dielectric anisotropy is small. The compound (12) is used mainly for the purpose of adjusting the viscosity or optical anisotropy. The compounds (13) and (14) are used mainly for the purpose of increasing the upper limit temperature to widen the temperature range of the liquid crystal phase or adjusting the optical anisotropy. When the amount of the compound (12), (13) or (14) is increased, the threshold voltage of the composition becomes high, and the viscosity becomes low. Accordingly, such a compound may be used in a large amount so far as the required value of the threshold voltage of the composition is met.

Preferred examples of the compounds (2) to (14) are the following compounds (2-1) to (2-9), compounds (3-1) to (3-97), compounds (4-1) to (4-33), compounds (5-1) to (5-56), compounds (6-1) to (6-3), compounds (7-1) to (7-4), compounds (8-1) to (8-6), compounds (9-1) to (9-4), compound (10-1), compound (11-1), compounds (12-1) to (12-11), compounds (13-1) to (13-21) and compounds (14-1) to (14-6), respectively. In these compounds, the meanings of the symbols $R^1, R^2, R^3, R^4, R^5, R^6, R^7, X^1$, and $X^2$ have the same meanings in the formulae (2) to (14), respectively.

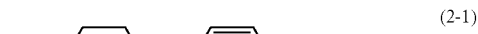

(2-1)

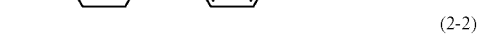

(2-2)

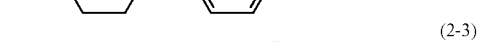

(2-3)

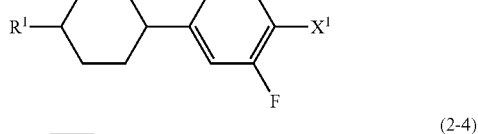

(2-4)

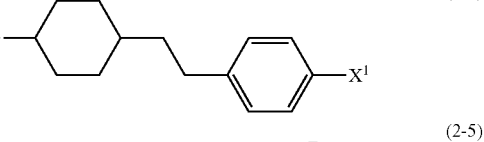

(2-5)

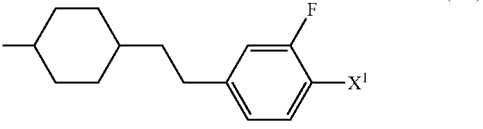

(2-6)

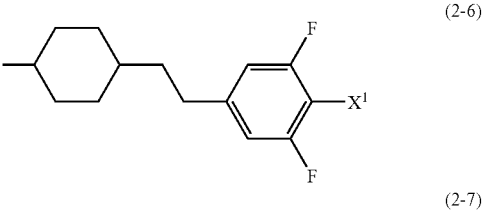

(2-7)

(2-8)

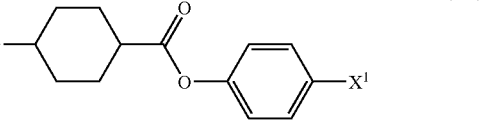

(2-9)

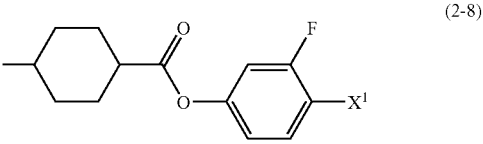

(3-1)

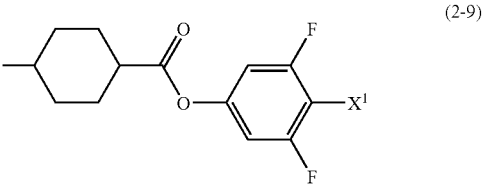

(3-2)

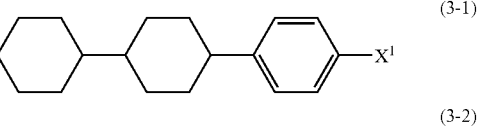

-continued

-continued
(3-20) 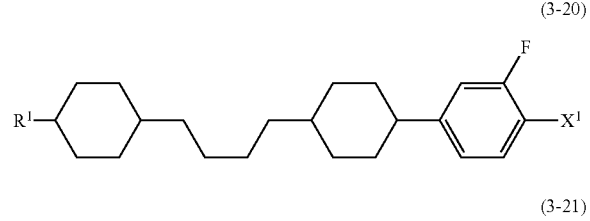
(3-21) 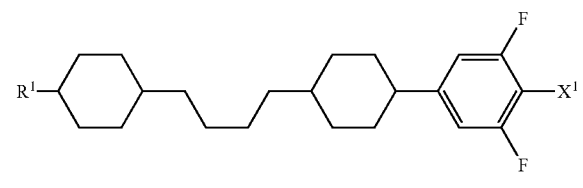
(3-22) 
(3-23) 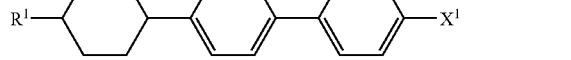
(3-24) 
(3-25) 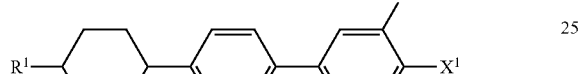
(3-26) 
(3-27) 
(3-28) 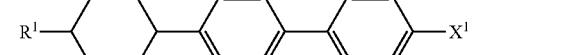
(3-29) 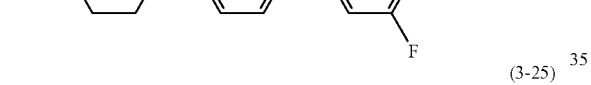
-continued
(3-30) 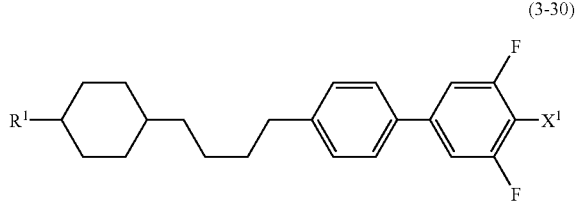
(3-31) 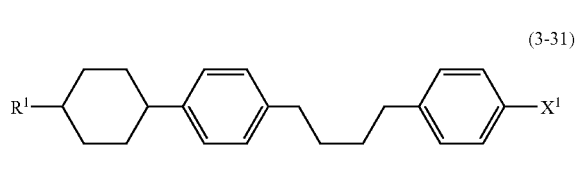
(3-32) 
(3-33) 
(3-34) 
(3-35) 
(3-36) 
(3-37) 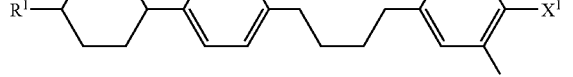
(3-38) 

(3-39)
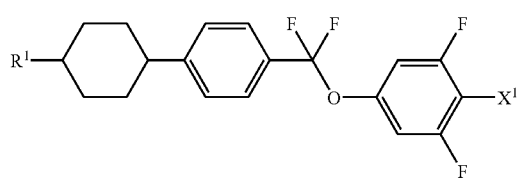
(3-40)
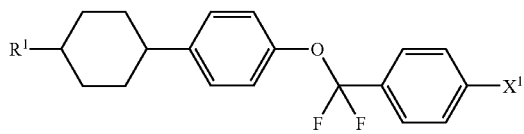
(3-41)
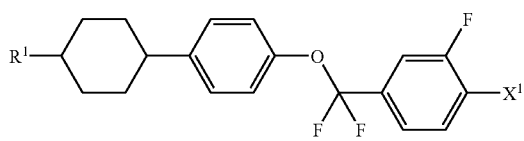
(3-42)
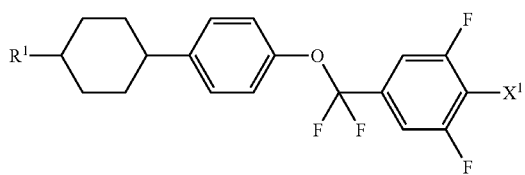
(3-43)
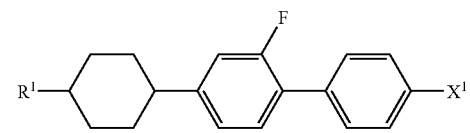
(3-44)
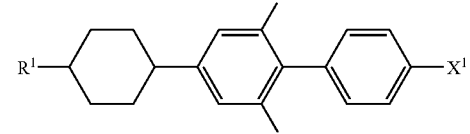
(3-45)
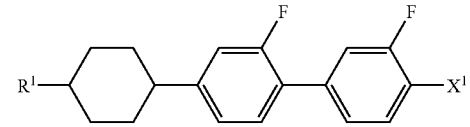
(3-46)
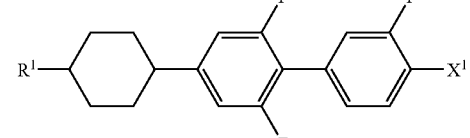
(3-47)
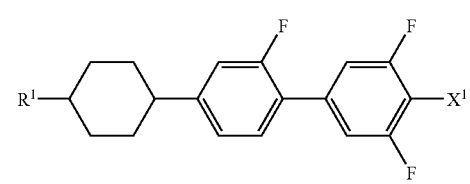
(3-48)
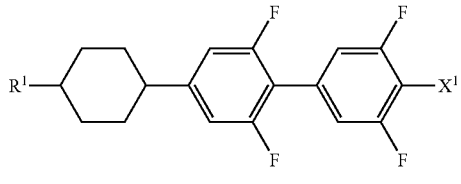
(3-49)
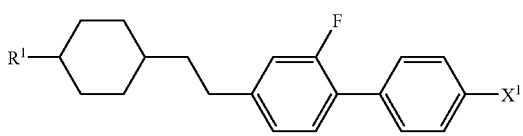
(3-50)
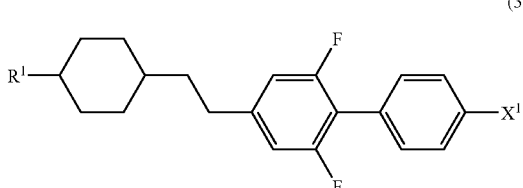
(3-51)
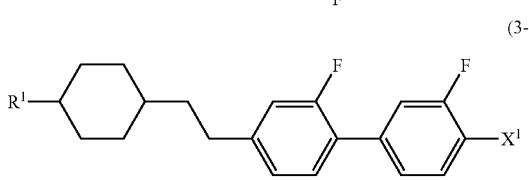
(3-52)
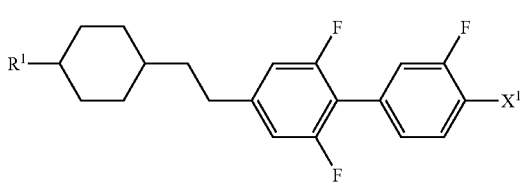
(3-53)
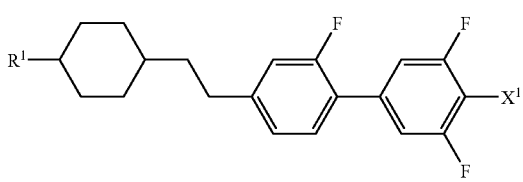
(3-54)
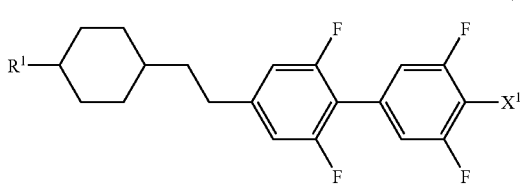
(3-55)
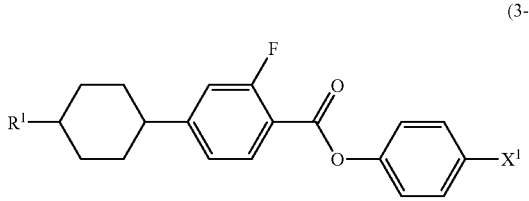

(3-56)
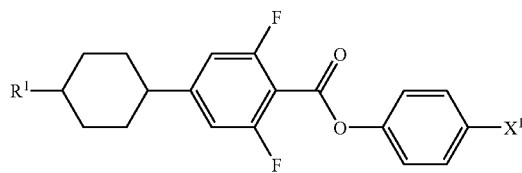
(3-57)
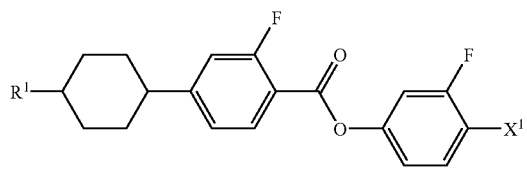
(3-58)
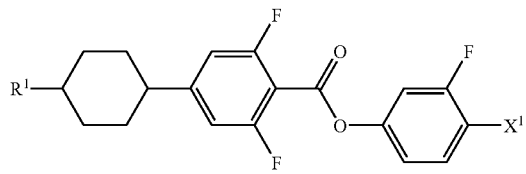
(3-59)
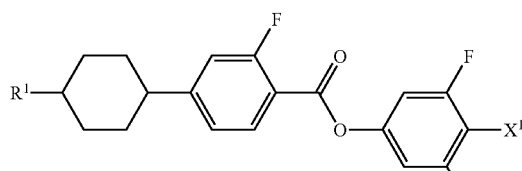
(3-60)
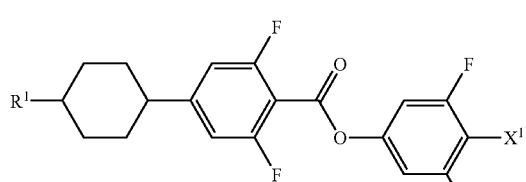
(3-61)
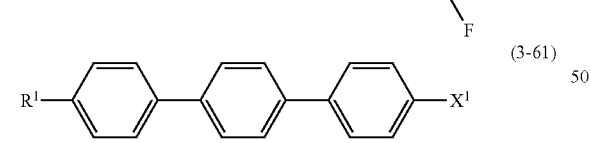
(3-62)
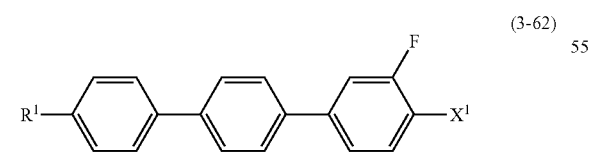
(3-63)
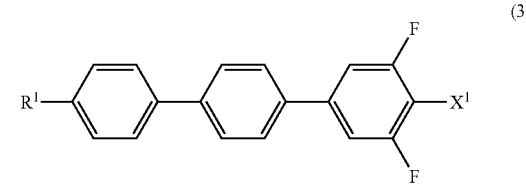
(3-64)
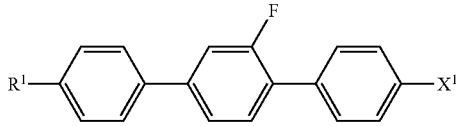
(3-65)
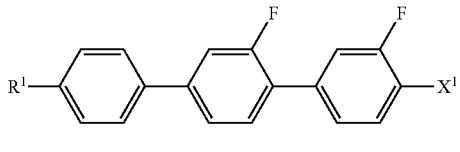
(3-66)
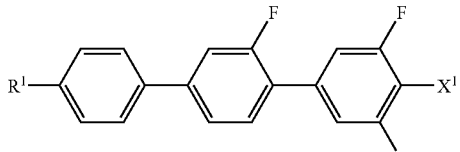
(3-67)
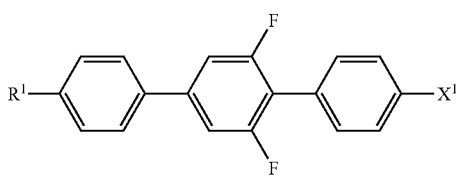
(3-68)
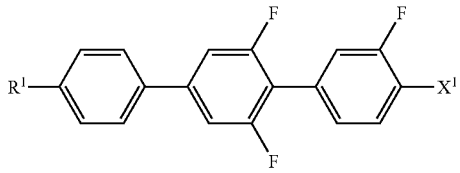
(3-69)
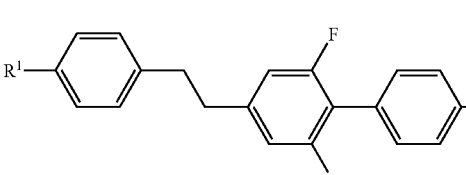
(3-70)
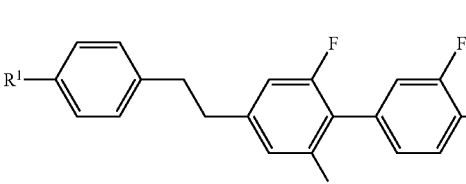
(3-71)
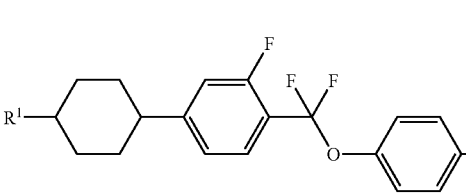

(3-72) 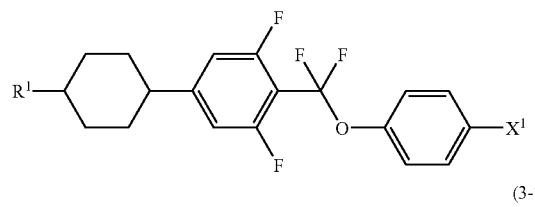
(3-73) 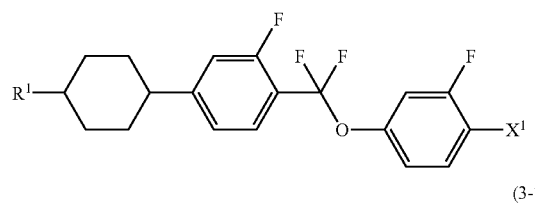
(3-74) 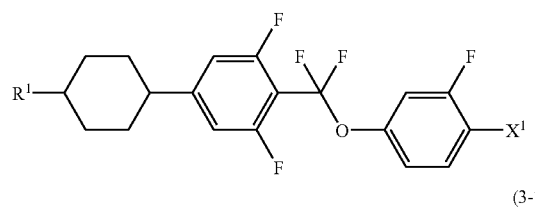
(3-75) 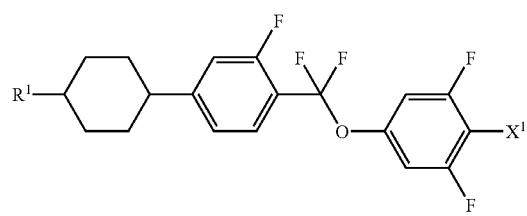
(3-76) 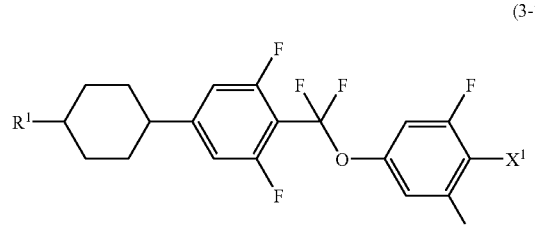
(3-77) 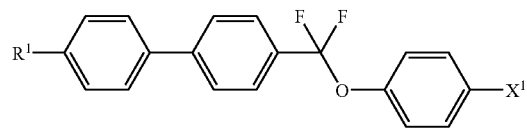
(3-78) 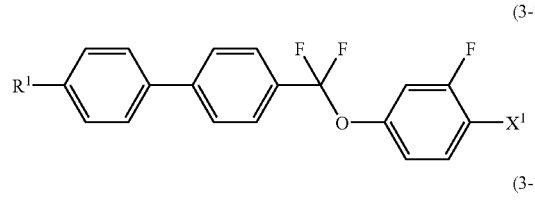
(3-79) 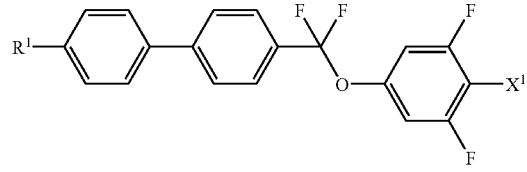
(3-80) 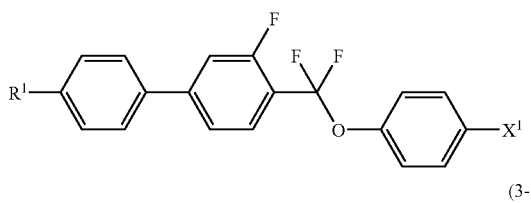
(3-81) 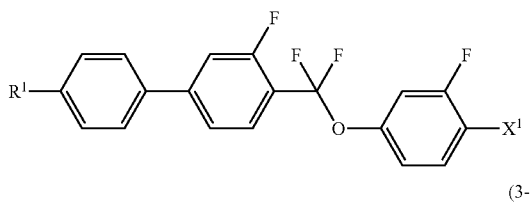
(3-82) 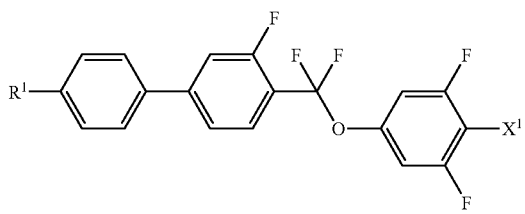
(3-83) 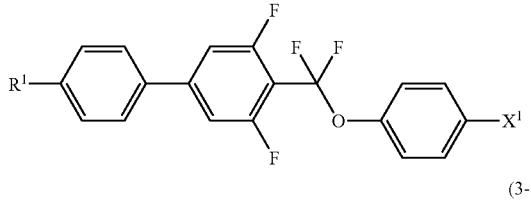
(3-84) 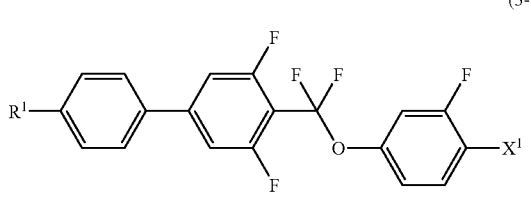
(3-85) 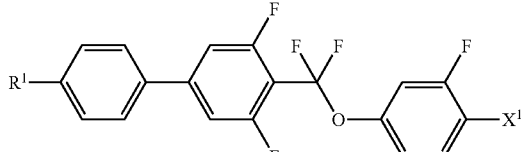
(3-86) 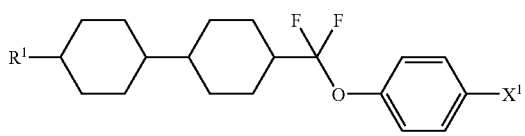
(3-87)

-continued
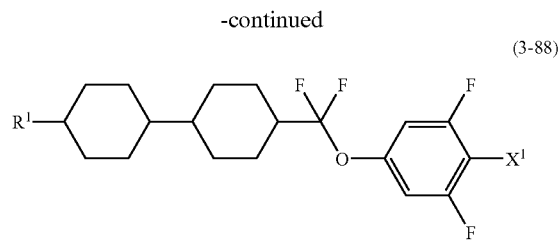 (3-88)
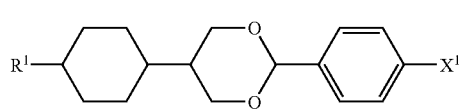 (3-89)
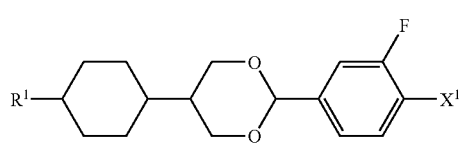 (3-90)
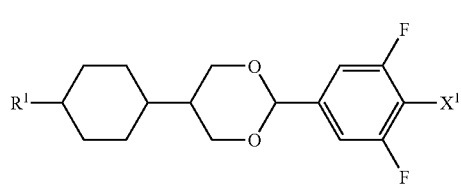 (3-91)
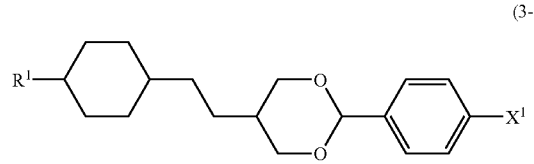 (3-92)
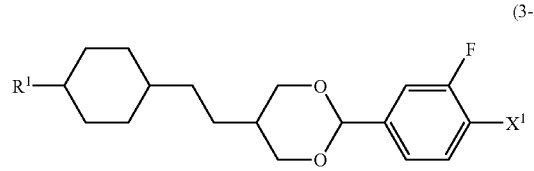 (3-93)
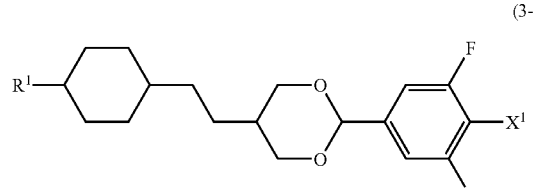 (3-94)
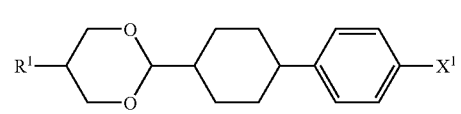 (3-95)
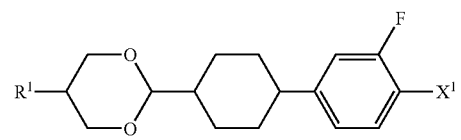 (3-96)
-continued
 (3-97)
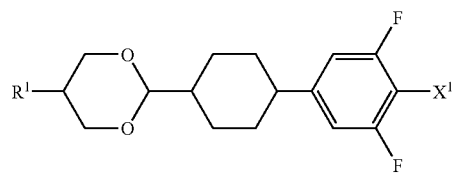
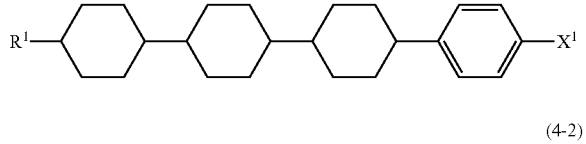 (4-1)
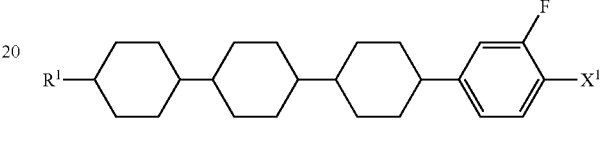 (4-2)
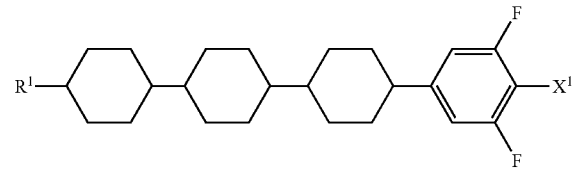 (4-3)
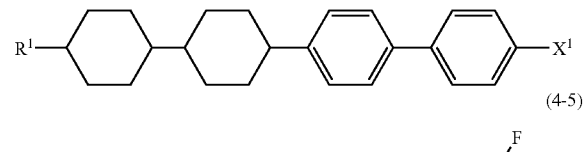 (4-4)
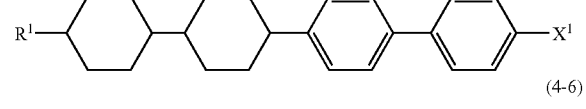 (4-5)
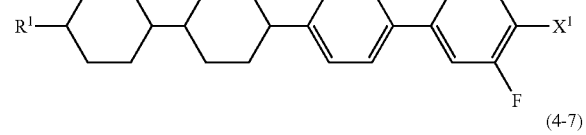 (4-6)
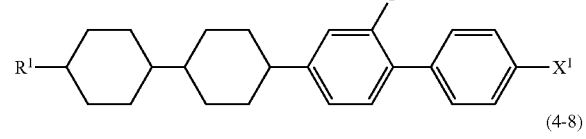 (4-7)
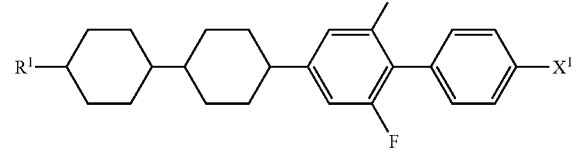 (4-8)

-continued
(4-9) 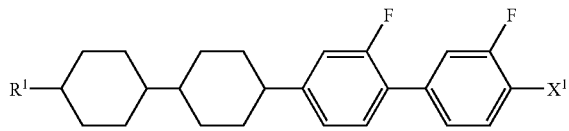
(4-10) 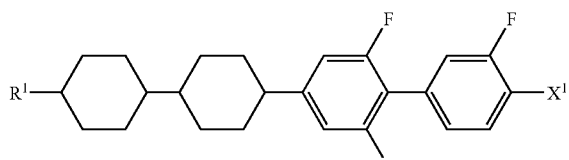
(4-11) 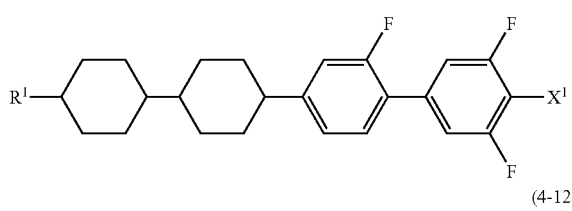
(4-12) 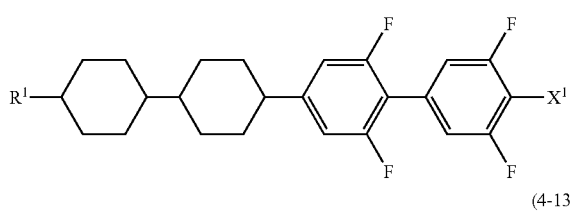
(4-13) 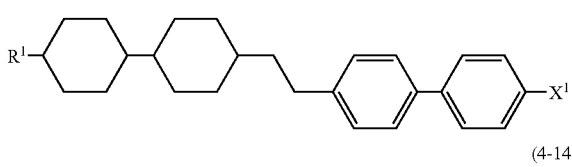
(4-14) 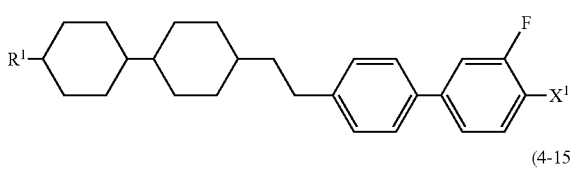
(4-15) 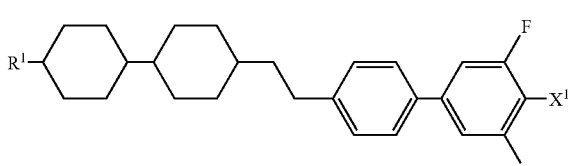
(4-16) 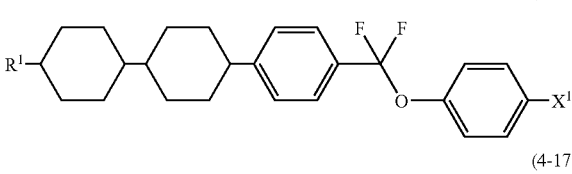
(4-17) 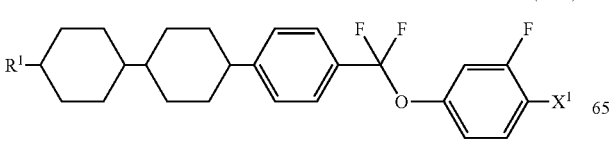
-continued
(4-18) 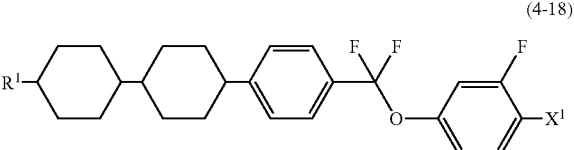
(4-19) 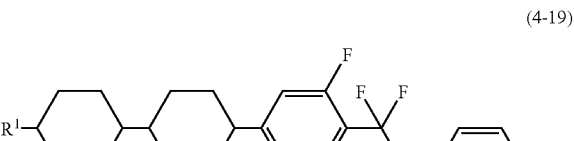
(4-20) 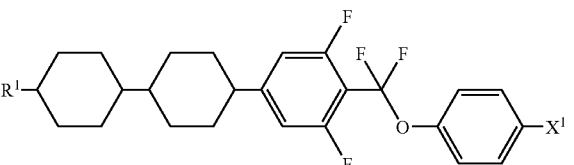
(4-21) 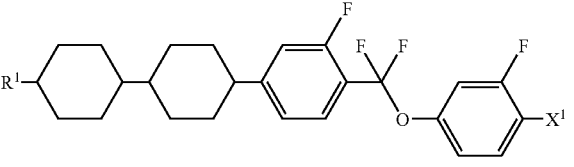
(4-22) 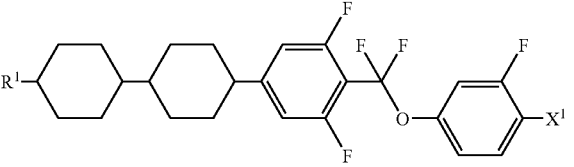
(4-23) 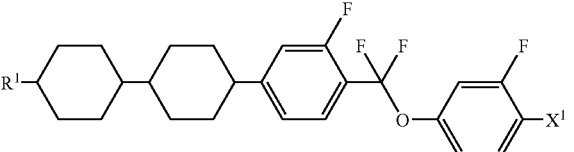
(4-24) 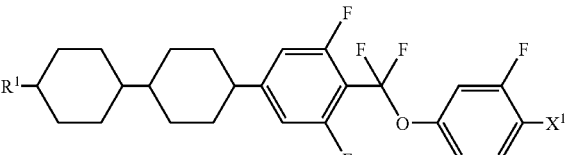
(4-25)

-continued
(4-26)
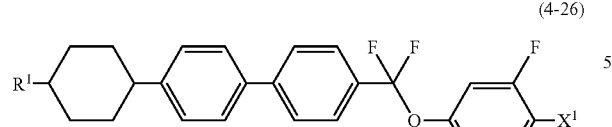
(4-27)
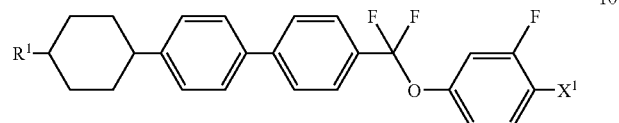
(4-28)
(4-29)
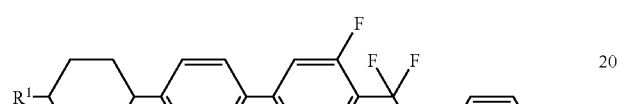
(4-30)
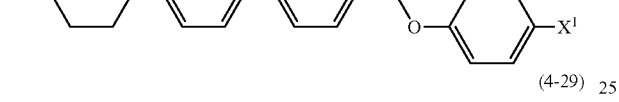
(4-31)
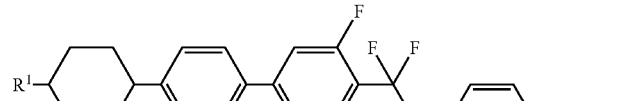
(4-32)
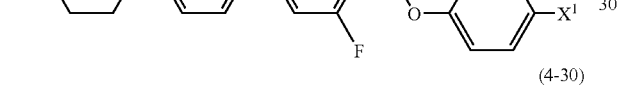
(4-33)
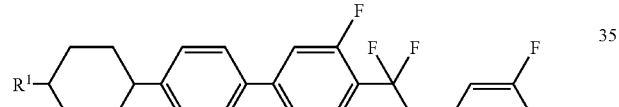
-continued
(5-1)
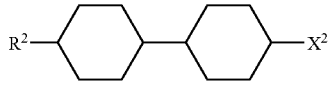
(5-2)
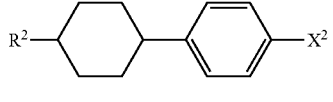
(5-3)
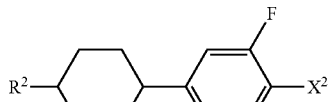
(5-4)
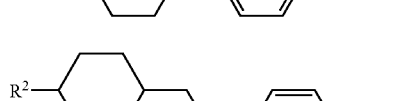
(5-5)
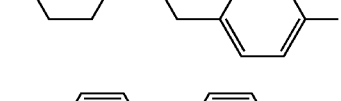
(5-6)
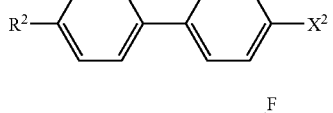
(5-7)
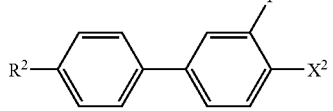
(5-8)
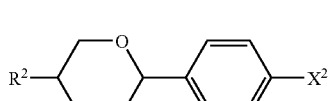
(5-9)
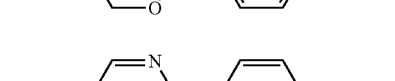
(5-10)
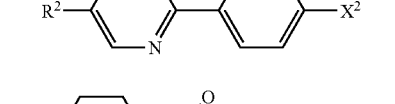
(5-11)
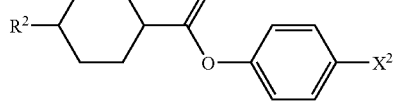
(5-12)
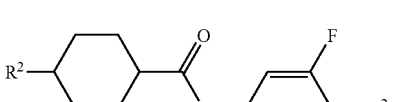

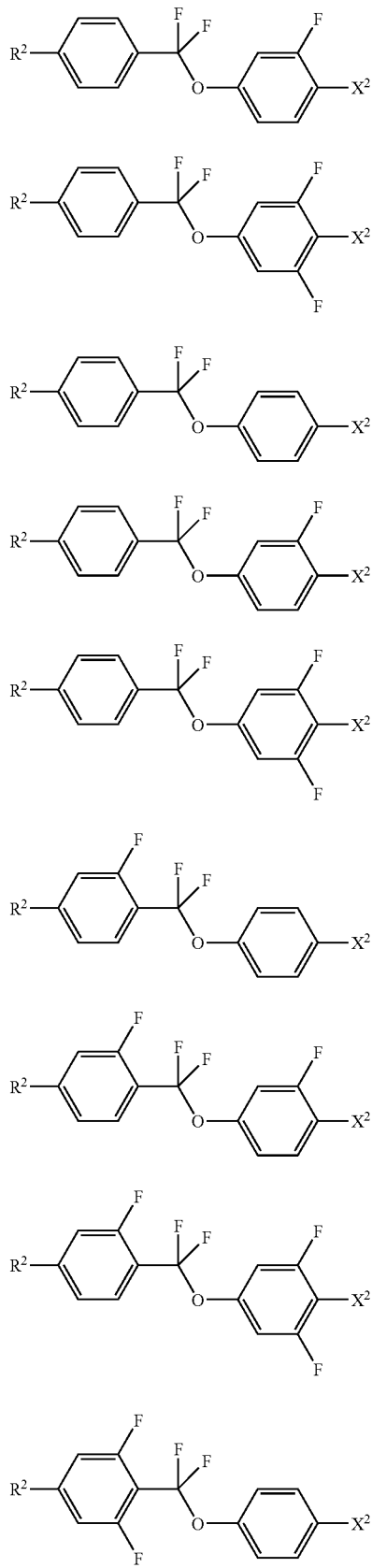
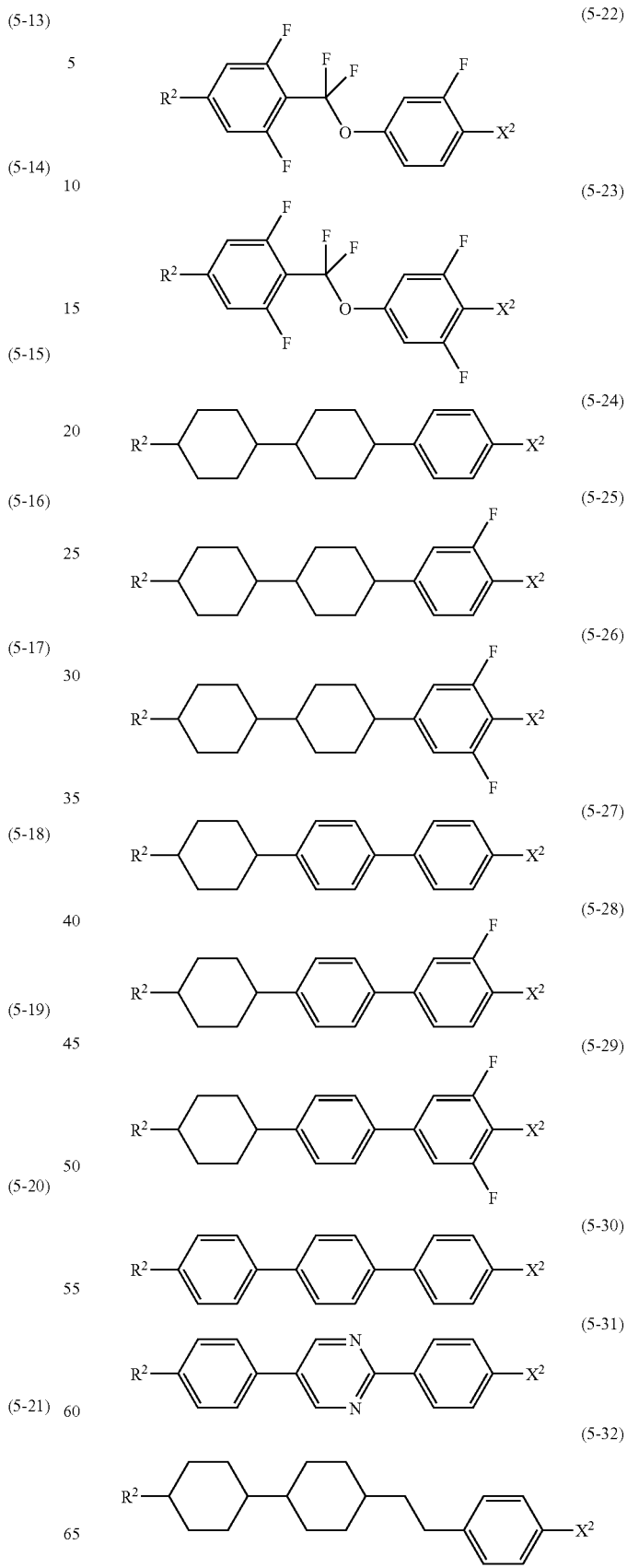

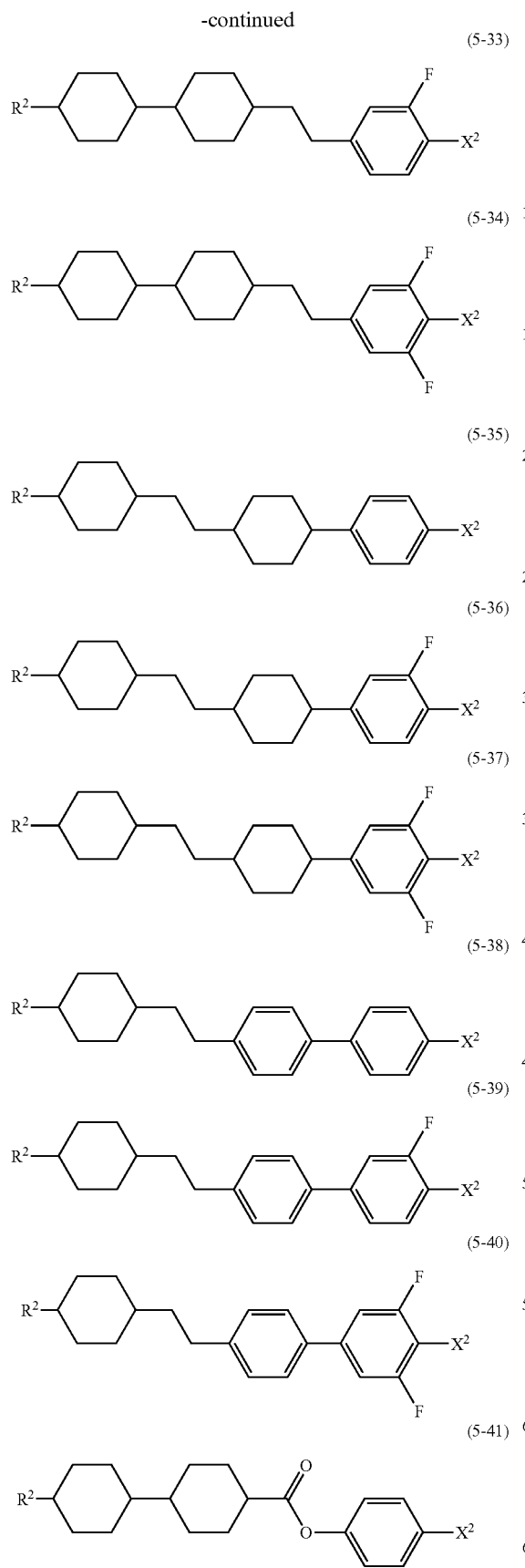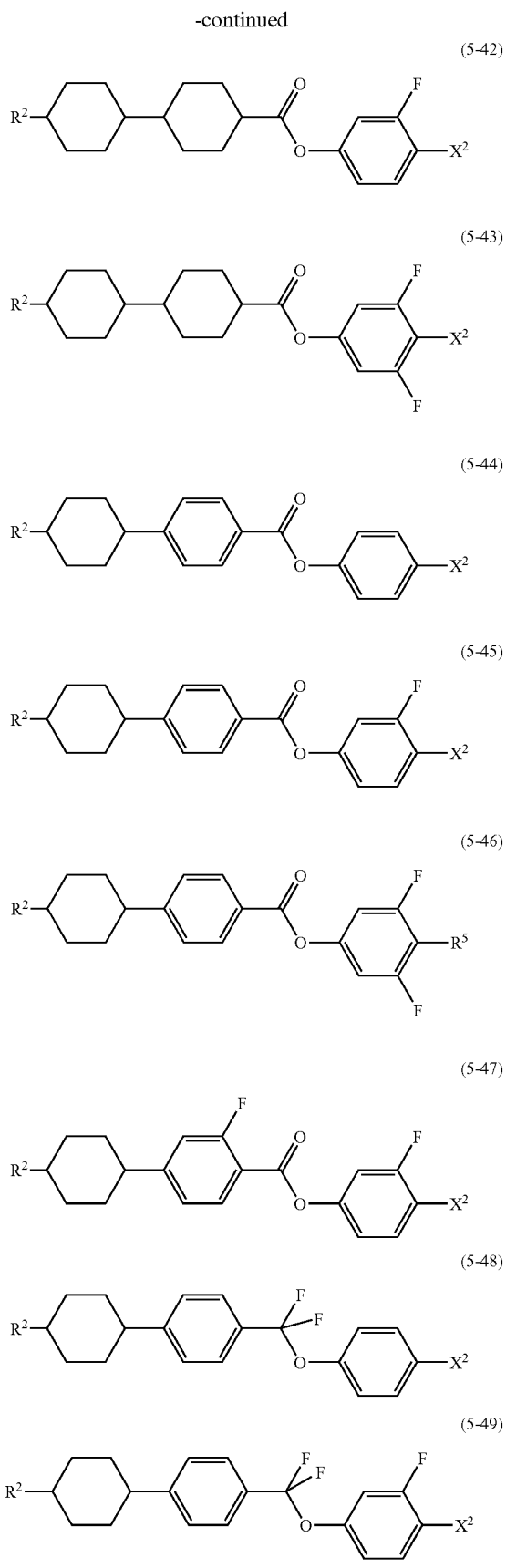

-continued
(5-50)
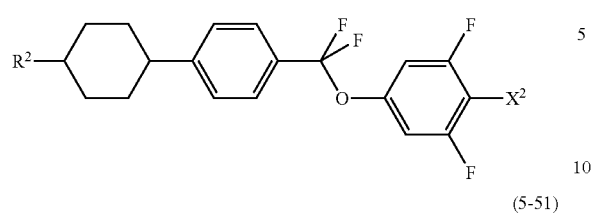
(5-51)
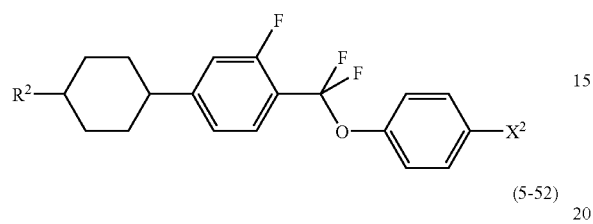
(5-52)
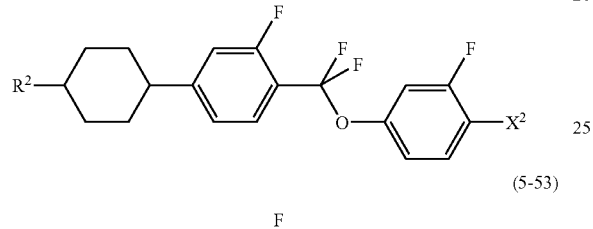
(5-53)
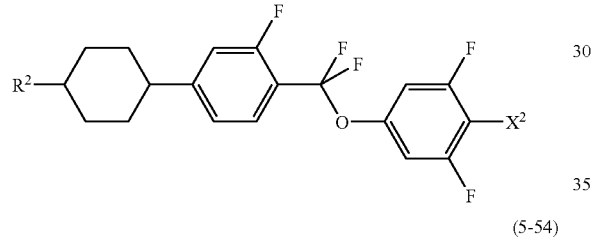
(5-54)
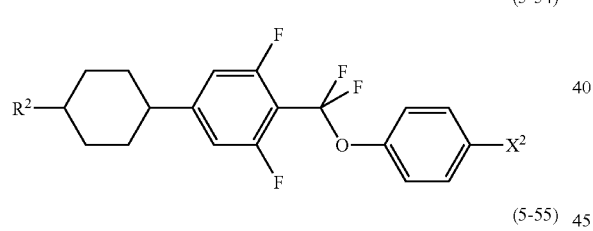
(5-55)
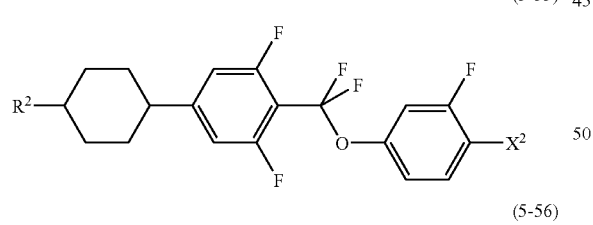
(5-56)
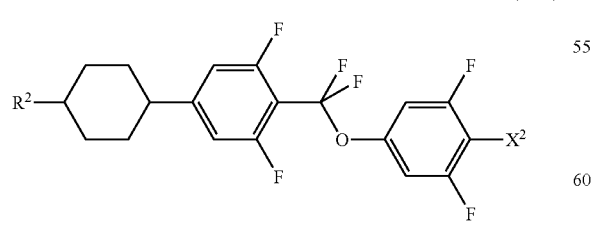
(6-1)
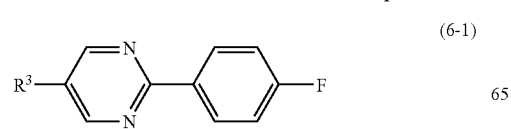
-continued
(6-2)
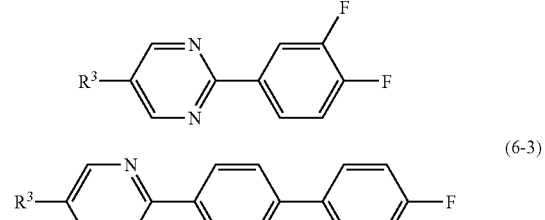
(6-3)
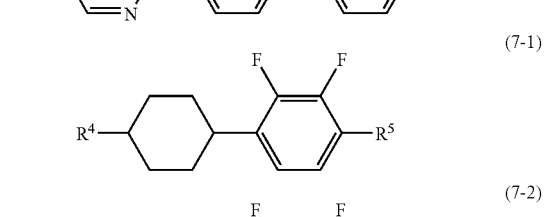
(7-1)
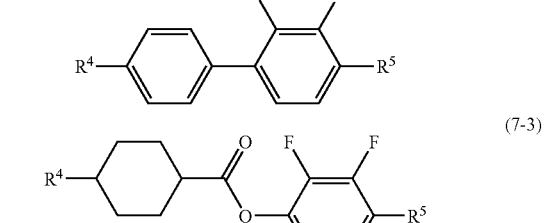
(7-2)
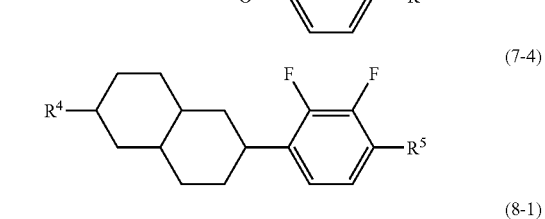
(7-3)
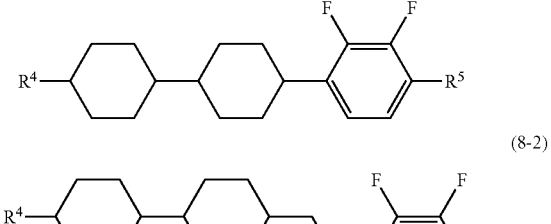
(7-4)
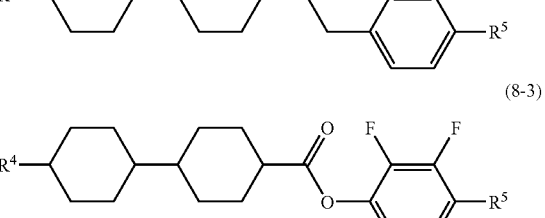
(8-1)
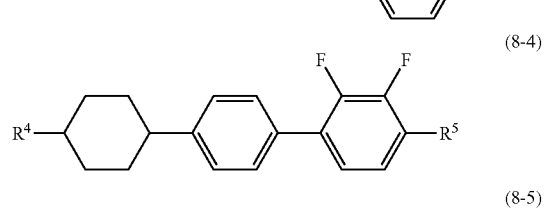
(8-2)
(8-3)
(8-4)
(8-5)
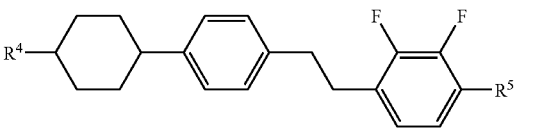

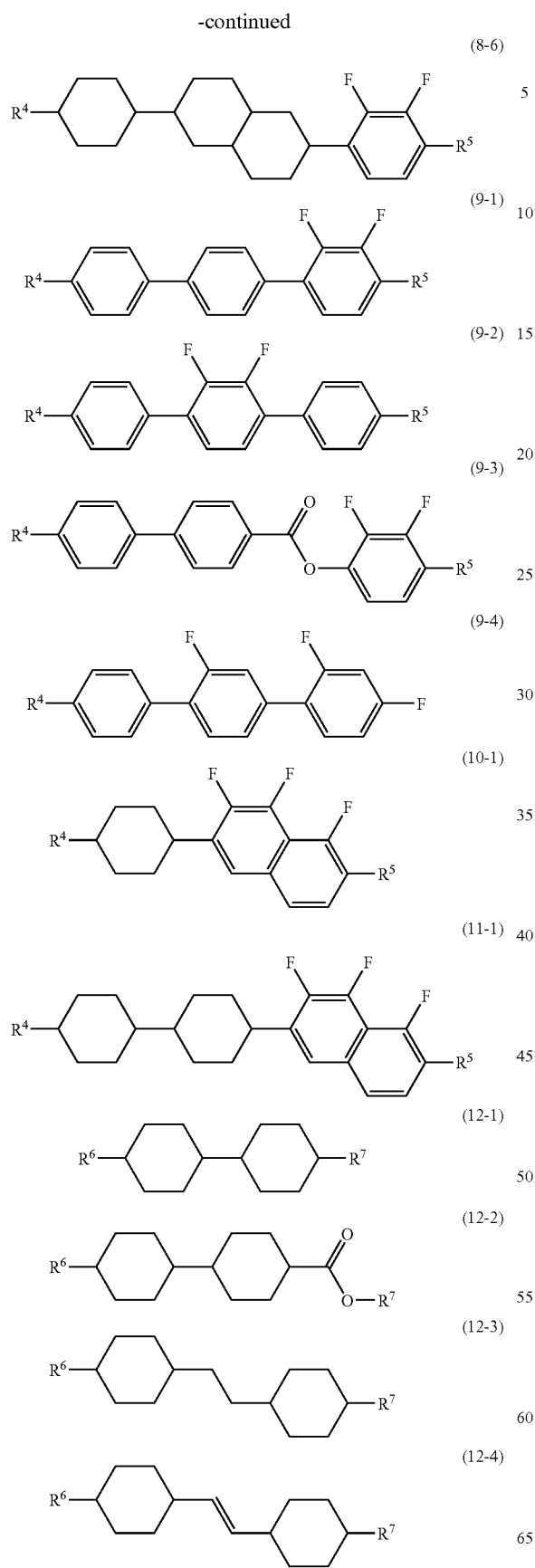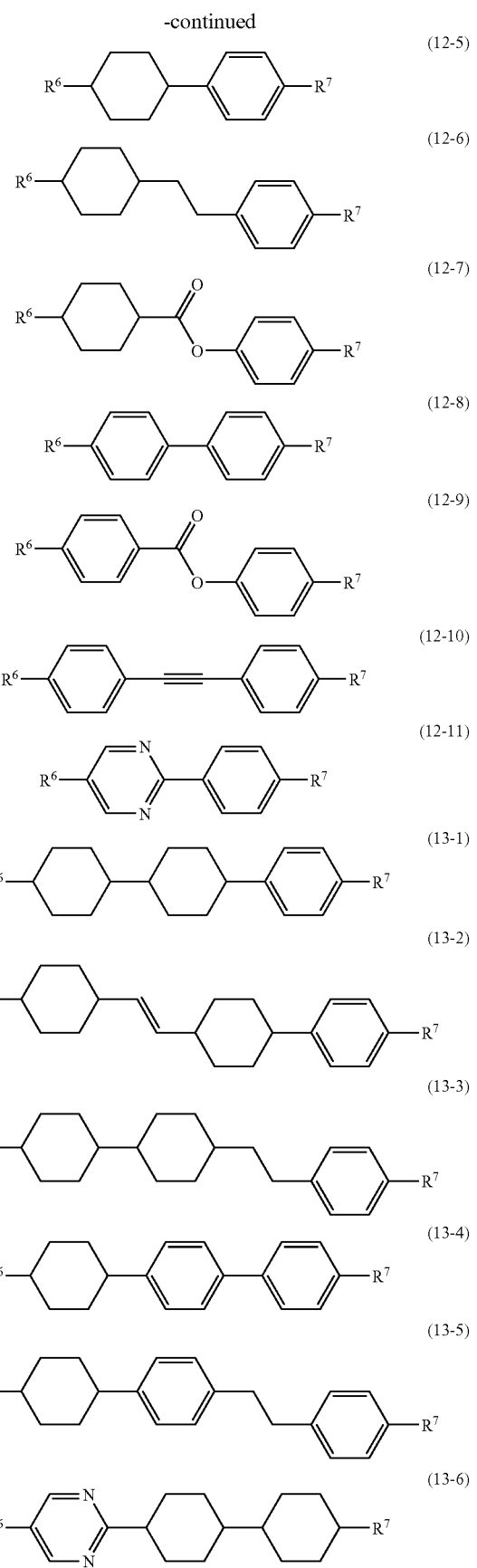

-continued
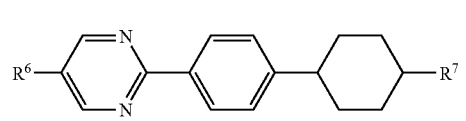 (13-7)
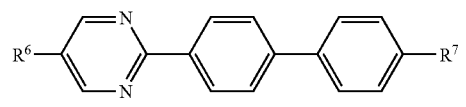 (13-8)
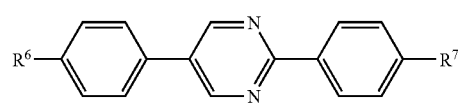 (13-9)
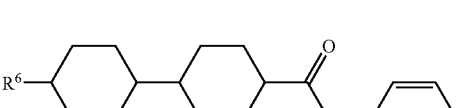 (13-10)
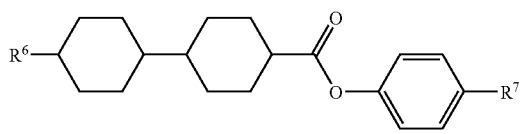 (13-11)
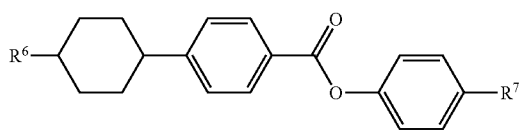 (13-12)
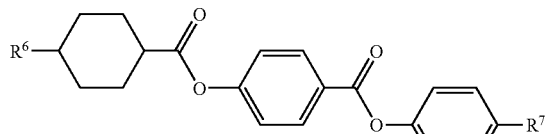 (13-13)
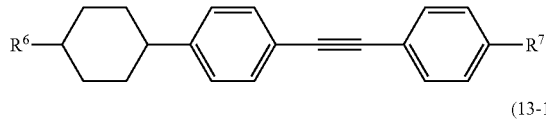 (13-14)
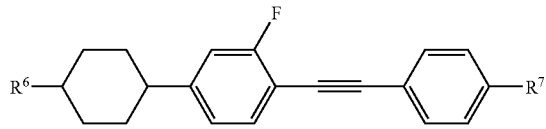 (13-15)
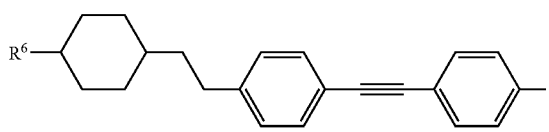 (13-16)
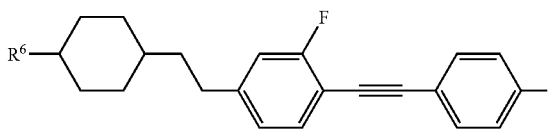 (13-17)
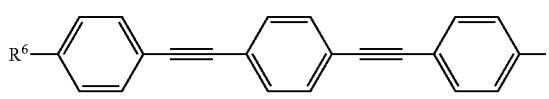
-continued
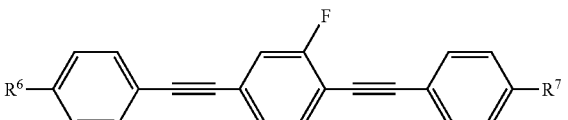 (13-18)
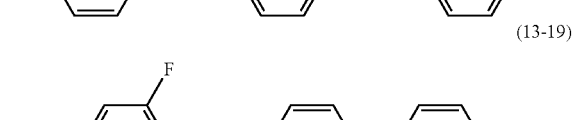 (13-19)
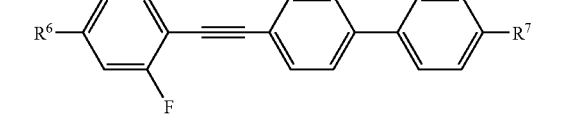 (13-20)
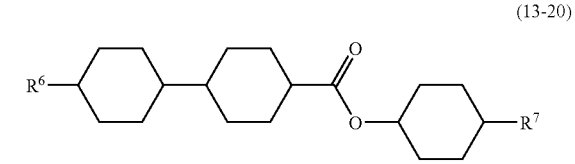 (13-21)
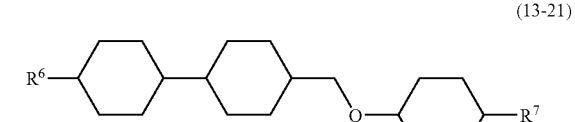 (14-1)
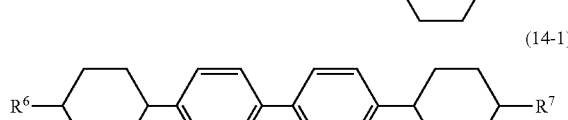 (14-2)
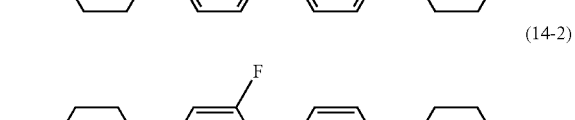 (14-3)
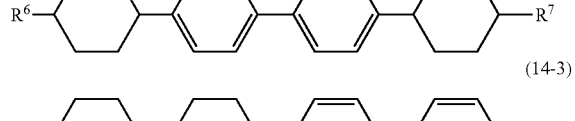 (14-4)
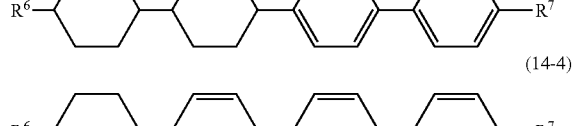 (14-5)
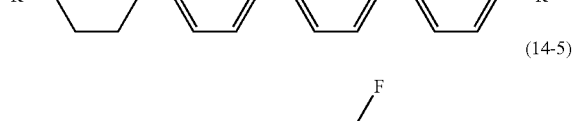 (14-6)
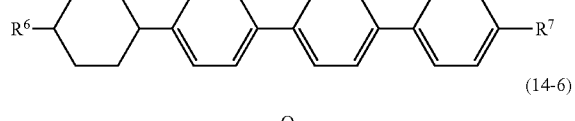
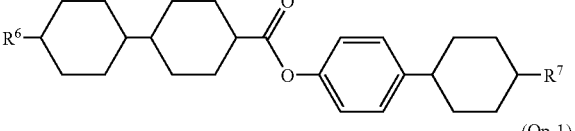 (Op-1)
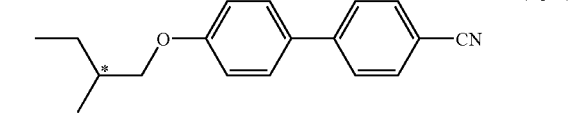

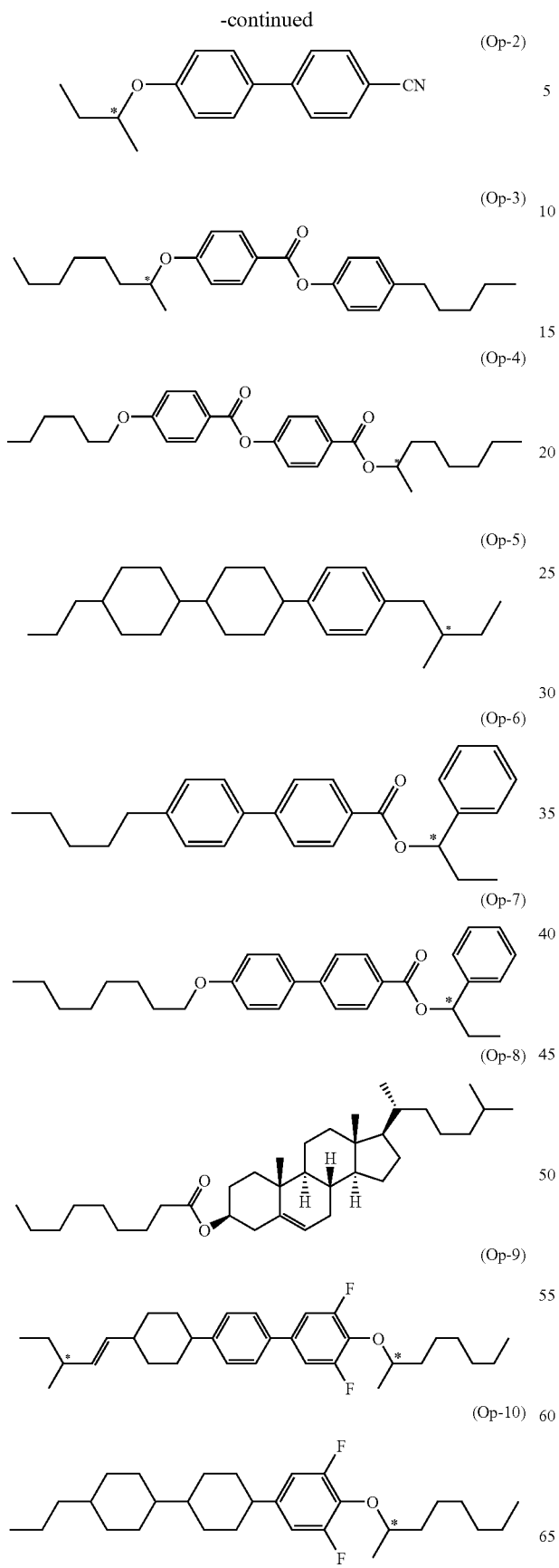
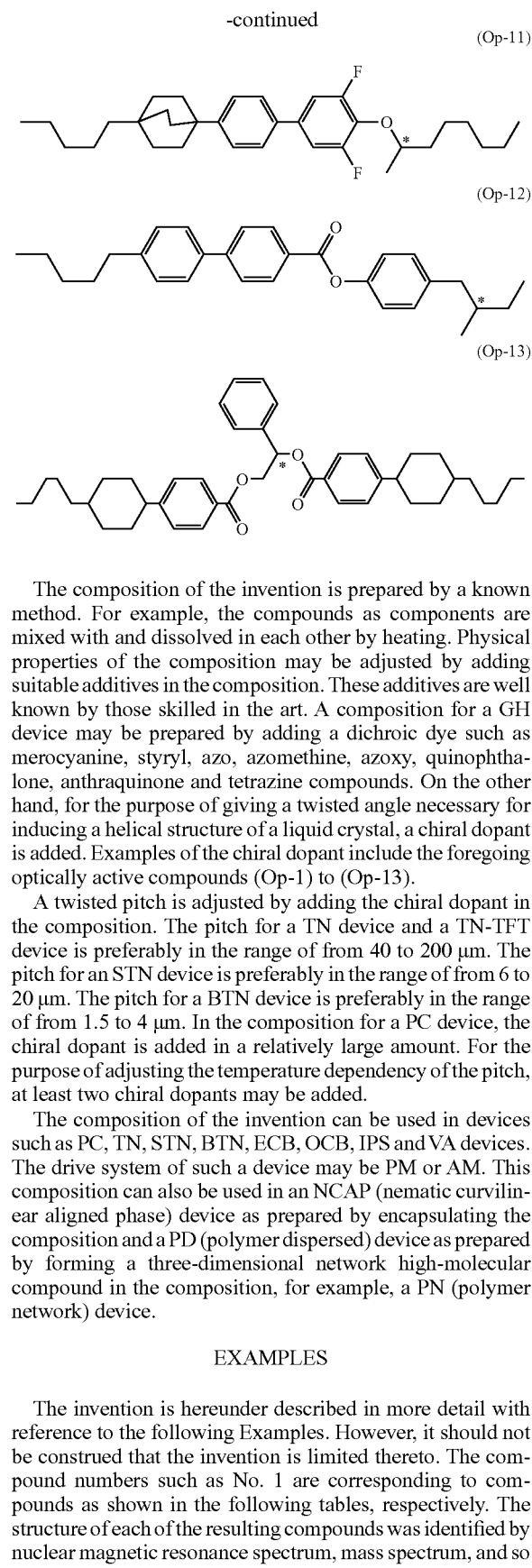

The composition of the invention is prepared by a known method. For example, the compounds as components are mixed with and dissolved in each other by heating. Physical properties of the composition may be adjusted by adding suitable additives in the composition. These additives are well known by those skilled in the art. A composition for a GH device may be prepared by adding a dichroic dye such as merocyanine, styryl, azo, azomethine, azoxy, quinophthalone, anthraquinone and tetrazine compounds. On the other hand, for the purpose of giving a twisted angle necessary for inducing a helical structure of a liquid crystal, a chiral dopant is added. Examples of the chiral dopant include the foregoing optically active compounds (Op-1) to (Op-13).

A twisted pitch is adjusted by adding the chiral dopant in the composition. The pitch for a TN device and a TN-TFT device is preferably in the range of from 40 to 200 μm. The pitch for an STN device is preferably in the range of from 6 to 20 μm. The pitch for a BTN device is preferably in the range of from 1.5 to 4 μm. In the composition for a PC device, the chiral dopant is added in a relatively large amount. For the purpose of adjusting the temperature dependency of the pitch, at least two chiral dopants may be added.

The composition of the invention can be used in devices such as PC, TN, STN, BTN, ECB, OCB, IPS and VA devices. The drive system of such a device may be PM or AM. This composition can also be used in an NCAP (nematic curvilinear aligned phase) device as prepared by encapsulating the composition and a PD (polymer dispersed) device as prepared by forming a three-dimensional network high-molecular compound in the composition, for example, a PN (polymer network) device.

EXAMPLES

The invention is hereunder described in more detail with reference to the following Examples. However, it should not be construed that the invention is limited thereto. The compound numbers such as No. 1 are corresponding to compounds as shown in the following tables, respectively. The structure of each of the resulting compounds was identified by nuclear magnetic resonance spectrum, mass spectrum, and so on.

Example 1

Synthesis of 6-(4-(4-propylcyclohexyl)cyclohexyl)-3,4-dihydrocoumarin (No. 72)

<First Stage>

4-(4-(4-Propylcyclohexyl)cyclohexyl)phenol (0.5 g) was dissolved in a mixed solvent of methylene chloride (5 ml) and chlorobenzene (1 ml), to which was then added dropwise a solution of bromine (0.28 g) in methylene chloride (2 ml) under ice cooling while stirring. After completion of the dropwise addition, the reaction mixture was stirred at room temperature for 30 minutes, added in ice water, and then extracted with methylene chloride. An organic layer was washed with water, rinsed with a sodium thiosulfate aqueous solution, and then dried over anhydrous magnesium sulfate. The methylene chloride solution was concentrated in vacuo and then subjected to isolation and purification by silica gel column chromatography, thereby obtaining a white crystal (0.25 g) of 2-bromo-4-(4-(4-propylcyclohexyl)cyclohexyl)phenol.

<Second Stage>

The foregoing 2-bromo-4-(4-(4-propylcyclohexyl)cyclohexyl)phenol (250 mg), potassium carbonate (109 mg), and benzyl chloride (135 mg) were mixed, to which were then added DMF (2 ml) and tetrabutylammonium bromide (20 mg), and the mixture was refluxed by heating for 30 minutes. After completion of the reaction, the reaction mixture was added in water and extracted with toluene. The resulting toluene layer was washed with water, rinsed with a sodium hydrogencarbonate aqueous solution, and then dried over anhydrous magnesium sulfate. The solution was concentrated in vacuo and then subjected to isolation and purification by silica gel column chromatography, thereby obtaining a colorless crystal (300 mg) of 2-bromo-4-(4-(4-propylcyclohexyl)cyclohexyl)phenylbenzyl ether.

<Third Stage>

A cyclohexane solution of sec-butyllithium (2.82 ml, 1.0 M) was added dropwise to a THF solution of the foregoing 2-bromo-4-(4-(4-propylcyclohexyl)cyclohexyl)phenylbenzyl ether (0.8 g) at −60° C. After completion of the dropwise addition, the reaction mixture was stirred at the same temperature for one hour, to which was then added dropwise DMF (340 mg), followed by raising the temperature to room temperature step by step. After completion of the reaction, the reaction mixture was added in ice water, extracted with toluene, washed with water, and then dried over anhydrous magnesium sulfate. The solution was concentrated in vacuo and then subjected to isolation and purification by silica gel column chromatography, thereby obtaining a white crystal (0.5 g) of 2-formyl-4-(4-(4-propylcyclohexyl)cyclohexyl)phenylbenzyl ether.

<Fourth Stage>

A THF solution of ethyl diethylphosphonoacetate (220 mg) was added to potassium butoxide (109 mg) while cooling at −40° C., and the mixture was stirred at the same temperature for an additional one hour. A THF solution of the foregoing 2-formyl-4-(4-(4-propylcyclohexyl)cyclohexyl)phenylbenzyl ether (340 mg) was added dropwise to the reaction mixture, and after completion of the dropwise addition, the temperature was raised to room temperature step by step. After completion of the reaction, the reaction mixture was added in ice water, extracted with toluene, washed with water, and then dried over anhydrous magnesium sulfate. The solution was concentrated in vacuo and then subjected to isolation and purification by silica gel column chromatography, thereby obtaining a white crystal of ethyl 2-(2-benzyloxy-5-(4-(4-propylcyclohexyl)cyclohexyl)cinnamate.

<Fifth Stage>

Palladium-on-carbon (5%, 100 mg) was added to the foregoing ethyl 2-(2-benzyloxy-5-(4-(4-propylcyclohexyl)cyclohexyl)cinnamate (400 mg), the mixture was dissolved in a toluene/SOLMIX (1/1) mixed solvent (2 ml), and the solution was stirred in a hydrogen atmosphere at an atmospheric pressure for 20 hours. After completion of the reaction, the palladium-on-carbon was removed from the solution by filtration, and the residual solution was concentrated in vacuo, thereby obtaining ethyl 3-(2-hydroxy-5-(4-(4-propylcyclohexyl)cyclohexyl)phenyl)propionate. This was used for the next reaction without performing additional purification.

<Sixth Stage>

The foregoing ethyl 3-(2-hydroxy-5-(4-(4-propylcyclohexyl)cyclohexyl)phenyl)propionate was dissolved in toluene, to which was then added p-toluenesulfonic acid (100 mg). A Dean-Stark apparatus was attached, and the mixture was stirred under reflux by heating for 3 hours. After completion of the reaction, the reaction mixture was washed with water, rinsed with a sodium hydrogencarbonate aqueous solution, and then dried over anhydrous magnesium sulfate. The solution was concentrated in vacuo and then subjected to isolation and purification by silica gel column chromatography, thereby obtaining a titled compound (100 mg). As a result of a variety of instrumental analyses, it was confirmed that this was the titled compound.

Example 2

Synthesis of 6-(4-(4-propylcyclohexyl)phenyl)-3,4-dihydrocoumarin (No. 60)

4-(4-propylcyclohexyl)phenylboronic acid (1.3 g), 6-bromo-3,4-dihydrocoumarin (1.0 g), potassium carbonate (1.2 g), tetrakistriphenylphosphine-palladium (51 mg), and tetrabutylammonium bromide (10 mg) were suspended in DME (10 ml), and the suspension was stirred under reflux by heating for 3 hours. After completion of the reaction, the reaction mixture was added in ice water and extracted with toluene. An organic layer was washed with water and then dried over anhydrous magnesium sulfate. The solution was concentrated in vacuo and then subjected to isolation and purification by silica gel column chromatography, thereby obtaining a titled compound (500 mg). As a result of a variety of instrumental analyses, it was confirmed that this was the titled compound.

Example 3

Synthesis of 8-fluoro-6-(4-(4-propylcyclohexyl)cyclohexyl)-3,4-dihydrocoumarin (No. 75)

A titled compound (0.1 g) was synthesized from 2-fluoro-4-(4-(4-propylcyclohexyl)cyclohexyl)phenol (0.5 g) in the same manner as described in Example 1.

Example 4

Synthesis of 6-(2-(4-pentylphenyl)ethyl)-3,4-dihydrocoumarin (No. 28)

<First Stage>

Butyllithium (16 ml, 1.5 M) was added dropwise to a solution of 6-bromo-3,4-dihydrocoumarin (4.5 g) in THF (50 ml) as cooled at −100° C. in an argon gas stream. After completion of the dropwise addition, the temperature of the reaction mixture was raised to −78° C., and a solution of zinc bromide (4.5 g) in THF (10 ml) was added dropwise to the reaction mixture. After completion of the dropwise addition, the temperature of the reaction mixture was raised to −30° C., and a solution of 2-(4-pentyl-2-fluorophenyl)acetaldehyde (4.1 g) in THF (40 ml) was added dropwise thereto. After completion of the dropwise addition, the temperature of the reaction mixture was raised to room temperature, followed by stirring for 18 hours. The reaction mixture was added in ice water, extracted with toluene, washed with water, and then dried over anhydrous magnesium sulfate. The solution was concentrated in vacuo and then subjected to isolation and purification by silica gel column chromatography, thereby obtaining 6-(1-hydroxy-2-(4-pentyl-2-fluorophenyl)ethyl)-3,4-dihydrocoumarin (3 g).

<Second Stage> p-Toluenesulfonic acid (0.4 g) was added to a solution of 6-(1-hydroxy-2-(4-pentyl-2-fluorophenyl)ethyl)-3,4-dihydrocoumarin (4 g) in toluene (30 ml), a Dean-Stark apparatus was attached, and the mixture was stirred under reflux by heating for 3 hours. After completion of the reaction, the reaction mixture was washed with water and dried over anhydrous magnesium sulfate. The solution was concentrated in vacuo, and the resulting yellow oily material was subjected to isolation and purification by silica gel column chromatography, thereby obtaining 6-(2-(4-pentylphenyl)ethenyl)-3,4-dihydrocoumarin (3.2 g).

<Third Stage>

Palladium-on-carbon (5%, 0.3 g) was added to a solution of 6-(2-(4-pentyl-2-fluorophenyl)ethenyl)-3,4-dihydrocoumarin (3.2 g) in ethanol (30 ml), and the mixture was stirred in a hydrogen atmosphere for 24 hours. The catalyst was removed from the reaction mixture by filtration, and the resulting solution was concentrated in vacuo and subjected to isolation and purification by silica gel column chromatography, thereby obtaining a while crystal (2.1 g) of a titled compound.

Example 5

Synthesis of 8-fluoro-6-(4-(4-vinylcyclohexyl)cyclohexyl)-3,4-dihydrocoumarin (No. 77)

<First Stage>

Butyllithium (1.6 ml, 1.5 M) was added dropwise to a solution of 6-bromo-8-fluoro-3,4-dihydrocoumarin (4.8 g) in THF (50 ml) as cooled at −100° C. in an argon gas stream. After completion of the dropwise addition, the temperature of the reaction mixture was raised to −78° C., and a solution of zinc bromide (5 g) in THF (100 ml) was added dropwise thereto. After completion of the dropwise addition, the temperature of the reaction mixture was raised to −30° C., and a solution of 4-(4-(1,3-dioxolan-2-yl)cyclohexyl)cyclohexanone (5.0 g) in THF (50 ml) was added dropwise thereto. After completion of the dropwise addition, the temperature of the reaction mixture was raised to room temperature, followed by stirring for 18 hours. The reaction mixture was added in ice water, extracted with toluene, washed with water, and then dried over anhydrous magnesium sulfate. The solution was concentrated in vacuo and then subjected to isolation and purification by silica gel column chromatography, thereby obtaining a colorless crystal of 1-(8-fluoro-3,4-dihydrocoumarin-6-yl)-4-(4-(1,3-dioxolan-2-yl)cyclohexyl)cyclohexanol (4.5 g).

<Second Stage> p-Toluenesulfonic acid (0.5 g) was added to a solution of 1-(8-fluoro-3,4-dihydrocoumarin-6-yl)-4-(4-(1,3-dioxolan-2-yl)cyclohexyl)cyclohexanol (4.5 g) in toluene (50 ml), a Dean and Stark apparatus was attached, and the mixture was refluxed for 3 hours. After completion of the reaction, the reaction mixture was washed with water and dried over anhydrous magnesium sulfate. The solution was concentrated in vacuo, and the resulting yellow oily material was subjected to isolation and purification by silica gel column chromatography, thereby obtaining 6-(4-(4-(1,3-dioxolan-2-yl)cyclohexyl)cyclohexenyl)-8-fluoro-3,4-dihydrocoumarin (4 g).

<Third Stage>

Palladium-on-carbon (5%, 0.4 g) was added to an ethanol solution of 6-(4-(4-(1,3-dioxolan-2-yl)cyclohexyl)cyclohexenyl)-8-fluoro-3,4-dihydrocoumarin (4 g), and the mixture was stirred in a hydrogen atmosphere for 24 hours. The catalyst was removed from the reaction mixture by filtration, and the resulting solution was concentrated in vacuo and subjected to isolation and purification by silica gel column chromatography, thereby obtaining 6-(4-(4-(1,3-dioxolan-2-yl)cyclohexyl)cyclohexyl)-8-fluoro-3,4-dihydrocoumarin (3.2 g).

<Fourth Stage>

Formic acid (98%, 5 ml) was added to a solution of 6-(4-(4-(1,3-dioxolan-2-yl)cyclohexyl)cyclohexyl)-8-fluoro-3,4-dihydrocoumarin (3.2 g) in toluene (30 ml), and the mixture was stirred under reflux by heating for 5 hours. The reaction mixture was washed with water and then dried over anhydrous magnesium sulfate, followed by concentration in vacuo. The resulting oily material was subjected to isolation and purification by silica. gel column chromatography, thereby obtaining 6-(4-(4-formylcyclohexyl)cyclohexyl)-8-fluoro-3,4-dihydrocoumarin (2.5 g).

<Fifth Stage>

Methyltriphenylphosphonium bromide (3.5 g) was suspended in THF (30 ml), to which was then added potassium butoxide (1.2 g) with stirring while cooling at −30° C. After continuing the stirring at the same temperature for 30 minutes, a solution of 6-(4-(4-formylcyclohexyl)cyclohexyl)-8-fluoro-3,4-dihydrocoumarin (3.2 g) in THF (30 ml) was added dropwise to the reaction mixture. After completion of the dropwise addition, the temperature of the reaction mixture was raised to room temperature, and the resulting reaction mixture was added in ice water and extracted with toluene. An organic layer was washed with water, dried over anhydrous magnesium sulfate, and then concentrated in vacuo. The resulting oily material was subjected to isolation and purification by silica gel column chromatography and recrystallized, thereby obtaining a titled compound (2.1 g).

Example 6

Synthesis of 6-(4-ethylcyclohexyl)-chroman-2-thione (No. 175)

6-(4-Ethylcyclohexyl)-3,4-dihydrocoumarin (2.6 g) and a Lowesson's reagent (3 g) were dissolved in xylene (50 ml), and the solution was allowed to react under reflux by heating for 5 hours. The reaction mixture was added in ice water and extracted with toluene. An organic layer was washed with water, dried over anhydrous magnesium sulfate, and then concentrated in vacuo. The resulting oily material was subjected to isolation and purification by silica gel column chromatography, thereby obtaining a white crystal (1.1 g) of a titled compound.

The following compounds Nos. 1 to 193 are synthesized on the basis of Examples 1 to 6 and the foregoing synthesis methods. The measurement procedures of the upper limit temperature, the viscosity, the optical anisotropy and the dielectric anisotropy are explained in the following Composition Examples.

1a

| No. | R | $Y^1$ | $Y^2$ | $Y^3$ | Transition Temp |
|---|---|---|---|---|---|
| 1 | $CH_3$ | H | H | H | |
| 2 | $C_3H_7$ | H | H | H | |
| 3 | $C_5H_{11}$ | H | H | H | |
| 4 | $C_2H_5O$ | H | H | H | |
| 5 | $CH_2=CHC_2H_4$ | H | H | H | |
| 6 | $C_3H_7$ | F | H | H | C 67.0 I |
| 7 | $C_3H_7$ | H | F | H | |
| 8 | $C_2H_5O$ | H | F | H | |
| 9 | $CH_2=CHC_2H_4$ | H | F | H | |
| 10 | $C_2H_5O$ | F | F | H | |
| 11 | $CH_2=CHC_2H_4$ | F | F | H | |
| 12 | $C_3H_7$ | F | F | F | |
| 13 | $CH_2=CHC_2H_4$ | F | F | F | |

1b

| No. | R | $Y^1$ | Transition Temp |
|---|---|---|---|
| 14 | $C_3H_7$ | H | |
| 15 | $C_2H_5O$ | H | |
| 16 | $CH_2=CHC_2H_4$ | H | |
| 17 | $C_2H_5$ | F | |
| 18 | $C_2H_5O$ | F | |
| 19 | $CH_2=CHC_2H_4$ | F | |

1c

| No. | R | $Y^1$ | $Y^2$ | $Y^3$ | Transition Temp |
|---|---|---|---|---|---|
| 26 | $CH_3$ | H | H | H | |
| 27 | $C_3H_7$ | H | H | H | |
| 28 | $C_5H_{11}$ | H | H | H | |
| 29 | $C_2H_5O$ | H | H | H | |
| 30 | $CH_2=CHC_2H_4$ | H | H | H | |
| 31 | $C_2H_5$ | F | H | H | |
| 32 | $C_3H_7$ | H | F | H | |
| 33 | $C_2H_5O$ | H | F | H | |
| 34 | $C_3H_7$ | H | F | F | |
| 35 | $C_3H_7$ | F | F | H | |
| 36 | $CH_2=CHC_2H_4$ | F | F | H | |
| 37 | $C_3H_7$ | F | F | F | |
| 38 | $CH_2=CHC_2H_4$ | F | F | F | |

1d

| No. | R | $Y^1$ | Transition Temp |
|---|---|---|---|
| 20 | $C_3H_7$ | H | |
| 21 | $C_2H_5O$ | H | |
| 22 | $CH_2=CH$ | H | |
| 23 | $C_2H_5$ | F | |
| 24 | $CH_3O$ | F | |
| 25 | $CH_2=CHC_2H_4$ | F | |

1e

| No. | R | $Y^1$ | $Y^2$ | $Y^3$ | $Y^4$ | $Y^5$ | Transition Temp |
|---|---|---|---|---|---|---|---|
| 39 | $C_2H_5$ | H | H | H | H | H | |
| 40 | $C_2H_5O$ | H | H | H | H | H | |
| 41 | $CH_2=CHC_2H_4$ | H | H | H | H | H | |
| 42 | $C_2H_5$ | F | H | H | H | H | |
| 43 | $C_3H_7$ | H | F | H | H | H | |
| 44 | $C_5H_{11}$ | H | H | H | F | H | |
| 45 | $C_2H_5$ | F | H | H | H | H | |
| 46 | $C_3H_7$ | H | F | H | F | H | |
| 47 | $C_5H_{11}$ | F | F | H | H | H | |
| 48 | $C_2H_5O$ | F | H | H | H | H | |
| 49 | $CH_2=CHC_2H_4$ | H | F | F | H | H | |

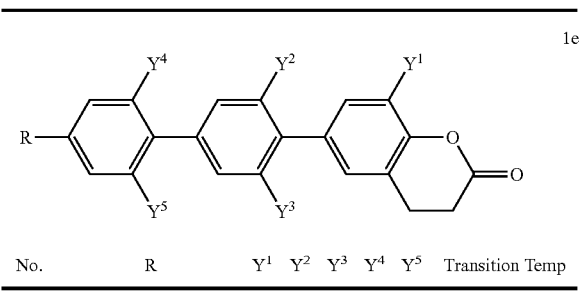

1e

| No. | R | Y¹ | Y² | Y³ | Y⁴ | Y⁵ | Transition Temp |
|---|---|---|---|---|---|---|---|
| 50 | $CH_3CH_2=CHC_2H_4$ | H | H | H | F | F | |
| 51 | $C_3H_7$ | F | F | H | F | H | |
| 52 | $C_5H_{11}$ | F | F | F | H | H | |
| 53 | $CH_3O$ | F | F | H | F | H | |
| 54 | $CH_2=CHC_2H_4$ | F | H | H | F | F | |
| 55 | $C_3H_7$ | F | F | F | F | H | |
| 56 | $CH_2=CHC_2H_4$ | F | F | H | F | F | |
| 57 | $C_3H_7$ | H | F | F | F | F | |
| 58 | $CH_2=CHC_2H_4$ | F | F | F | F | F | |

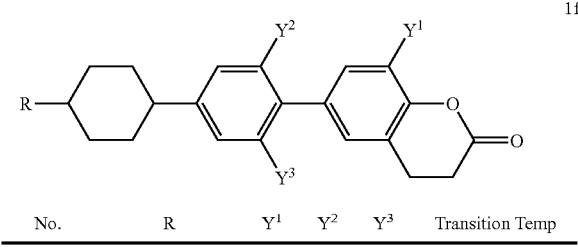

1f

| No. | R | Y¹ | Y² | Y³ | Transition Temp |
|---|---|---|---|---|---|
| 59 | $CH_3$ | H | H | H | |
| 60 | $C_3H_7$ | H | H | H | C 136.5 N 204.1 I |
| 61 | $C_5H_{11}$ | H | H | H | |
| 62 | $C_2H_5O$ | H | H | H | |
| 63 | $CH_2=CHC_2H_4$ | H | H | H | |
| 64 | $C_2H_5$ | F | H | H | |
| 65 | $C_3H_7$ | H | F | H | |
| 66 | $C_2H_5O$ | H | F | H | |
| 67 | $CH_2=CHC_2H_4$ | H | F | H | |
| 68 | $C_2H_5O$ | F | F | H | |
| 69 | $CH_2=CHC_2H_4$ | F | F | H | |
| 70 | $C_3H_7$ | F | F | F | |
| 71 | $CH_2=CHC_2H_4$ | F | F | F | |

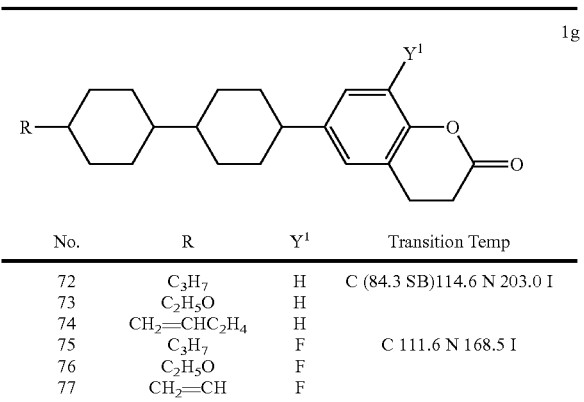

1g

| No. | R | Y¹ | Transition Temp |
|---|---|---|---|
| 72 | $C_3H_7$ | H | C (84.3 SB)114.6 N 203.0 I |
| 73 | $C_2H_5O$ | H | |
| 74 | $CH_2=CHC_2H_4$ | H | |
| 75 | $C_3H_7$ | F | C 111.6 N 168.5 I |
| 76 | $C_2H_5O$ | F | |
| 77 | $CH_2=CH$ | F | |

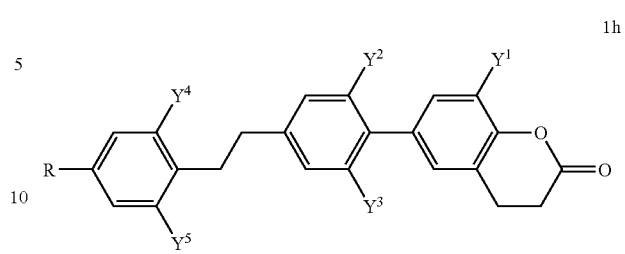

1h

| No. | R | Y¹ | Y² | Y³ | Y⁴ | Y⁵ | Transition Temp |
|---|---|---|---|---|---|---|---|
| 84 | $C_2H_5$ | H | H | H | H | H | |
| 85 | $C_2H_5O$ | H | H | H | H | H | |
| 86 | $CH_2=CHC_2H_4$ | H | H | H | H | H | |
| 87 | $C_2H_5$ | F | H | H | H | H | |
| 88 | $C_3H_7$ | H | F | H | H | H | |
| 89 | $C_5H_{11}$ | H | H | H | F | H | |
| 90 | $C_2H_5$ | F | H | H | F | H | |
| 91 | $C_3H_7$ | H | F | H | F | H | |
| 92 | $C_5H_{11}$ | F | F | H | H | H | |
| 93 | $C_2H_5O$ | F | H | H | H | H | |
| 94 | $CH_2=CHC_2H_4$ | H | F | F | H | H | |
| 95 | $CH_3CH_2=CHC_2H_4$ | H | H | H | F | F | |
| 96 | $C_3H_7$ | F | F | H | F | H | |
| 97 | $C_5H_{11}$ | F | F | F | H | H | |
| 98 | $CH_3O$ | F | F | H | F | H | |
| 99 | $CH_2=CHC_2H_4$ | F | H | H | F | F | |
| 100 | $C_3H_7$ | F | F | F | F | H | |
| 101 | $CH_2=CHC_2H_4$ | F | F | H | F | F | |
| 102 | $C_3H_7$ | H | F | F | F | F | |
| 103 | $CH_2=CHC_2H_4$ | F | F | F | F | F | |

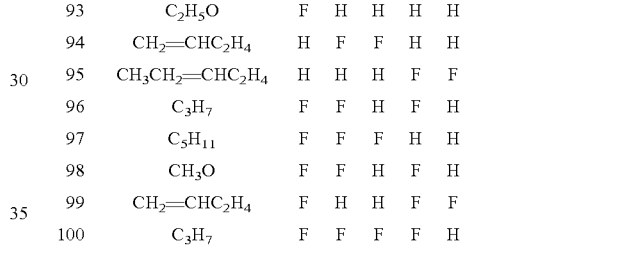

1i

| No. | R | Y¹ | Y² | Y³ | Transition Temp |
|---|---|---|---|---|---|
| 104 | $CH_3$ | H | H | H | |
| 105 | $C_3H_7$ | H | H | H | |
| 106 | $C_5H_{11}$ | H | H | H | |
| 107 | $C_2H_5O$ | H | H | H | |
| 108 | $CH_2=CHC_2H_4$ | H | H | H | |
| 109 | $C_2H_5$ | F | H | H | |
| 110 | $C_3H_7$ | H | F | H | |
| 111 | $C_2H_5O$ | H | F | H | |
| 112 | $CH_2=CHC_2H_4$ | H | F | H | |
| 113 | $C_2H_5O$ | F | F | H | |
| 114 | $CH_2=CHC_2H_4$ | F | F | H | |
| 115 | $C_3H_7$ | F | F | F | |
| 116 | $CH_2=CHC_2H_4$ | F | F | F | |

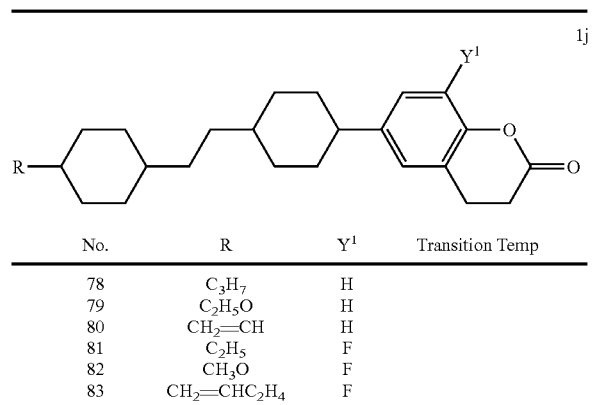

1j

| No. | R | Y¹ | Transition Temp |
|---|---|---|---|
| 78 | $C_3H_7$ | H | |
| 79 | $C_2H_5O$ | H | |
| 80 | $CH_2{=}CH$ | H | |
| 81 | $C_2H_5$ | F | |
| 82 | $CH_3O$ | F | |
| 83 | $CH_2{=}CHC_2H_4$ | F | |

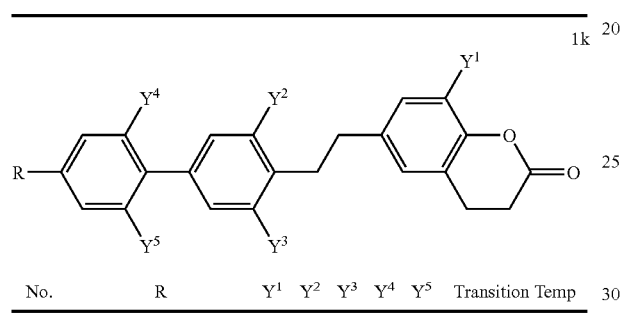

1k

| No. | R | Y¹ | Y² | Y³ | Y⁴ | Y⁵ | Transition Temp |
|---|---|---|---|---|---|---|---|
| 117 | $C_2H_5$ | H | H | H | H | H | |
| 118 | $C_2H_5O$ | H | H | H | H | H | |
| 119 | $CH_2{=}CHC_2H_4$ | H | H | H | H | H | |
| 120 | $C_2H_5$ | F | H | H | H | H | |
| 121 | $C_3H_7$ | H | F | H | H | H | |
| 122 | $C_5H_{11}$ | H | H | H | F | H | |
| 123 | $C_2H_5$ | F | H | H | F | H | |
| 124 | $C_3H_7$ | H | F | H | F | H | |
| 125 | $C_5H_{11}$ | F | H | H | H | H | |
| 126 | $C_2H_5O$ | F | H | H | H | H | |
| 127 | $CH_2{=}CHC_2H_4$ | H | F | F | H | H | |
| 128 | $CH_3CH_2{=}CHC_2H_4$ | H | H | H | F | F | |
| 129 | $C_3H_7$ | F | F | H | F | H | |
| 130 | $C_5H_{11}$ | F | F | H | F | H | |
| 131 | $CH_3O$ | F | F | H | F | H | |
| 132 | $CH_2{=}CHC_2H_4$ | F | H | H | F | F | |
| 133 | $C_3H_7$ | F | F | F | F | H | |
| 134 | $CH_2{=}CHC_2H_4$ | F | F | F | F | H | |
| 135 | $C_3H_7$ | H | F | F | F | F | |
| 136 | $CH_2{=}CHC_2H_4$ | F | F | F | F | F | |

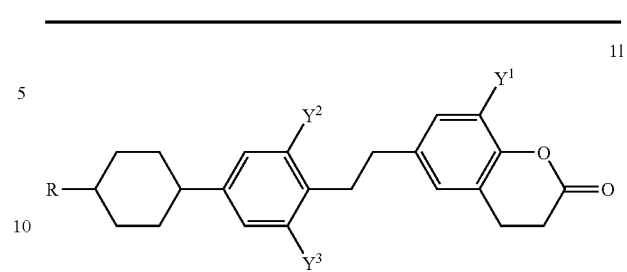

1l

| No. | R | Y¹ | Y² | Y³ | Transition Temp |
|---|---|---|---|---|---|
| 137 | $CH_3$ | H | H | H | |
| 138 | $C_3H_7$ | H | H | H | |
| 139 | $C_5H_{11}$ | H | H | H | |
| 140 | $C_2H_5O$ | H | H | H | |
| 141 | $CH_2{=}CHC_2H_4$ | H | H | H | |
| 142 | $C_2H_5$ | F | H | H | |
| 143 | $C_3H_7$ | H | F | H | |
| 144 | $C_2H_5O$ | H | F | H | |
| 145 | $C_3H_7$ | H | F | F | |
| 146 | $C_3H_7$ | F | F | H | |
| 147 | $CH_2{=}CHC_2H_4$ | F | F | H | |
| 148 | $C_3H_7$ | F | F | F | |
| 149 | $CH_2{=}CHC_2H_4$ | F | F | F | |

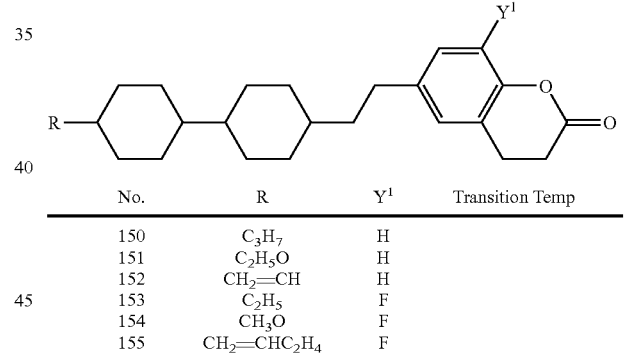

1m

| No. | R | Y¹ | Transition Temp |
|---|---|---|---|
| 150 | $C_3H_7$ | H | |
| 151 | $C_2H_5O$ | H | |
| 152 | $CH_2{=}CH$ | H | |
| 153 | $C_2H_5$ | F | |
| 154 | $CH_3O$ | F | |
| 155 | $CH_2{=}CHC_2H_4$ | F | |

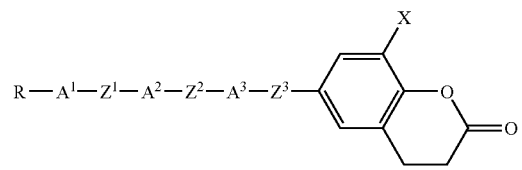

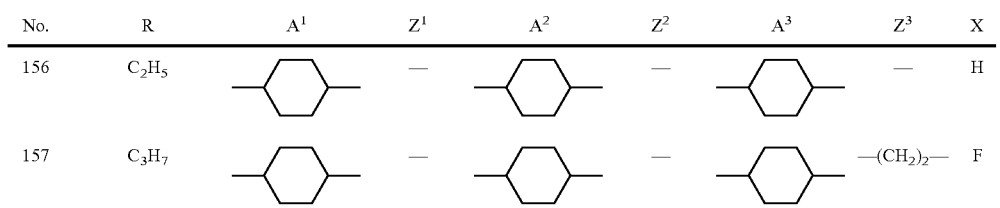

| No. | R | A¹ | Z¹ | A² | Z² | A³ | Z³ | X |
|---|---|---|---|---|---|---|---|---|
| 156 | $C_2H_5$ | cyclohexyl | — | cyclohexyl | — | cyclohexyl | — | H |
| 157 | $C_3H_7$ | cyclohexyl | — | cyclohexyl | — | cyclohexyl | $-(CH_2)_2-$ | F |

-continued
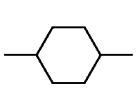
| No. | R | A¹ | Z¹ | A² | Z² | A³ | Z³ | X |
|---|---|---|---|---|---|---|---|---|
| 158 | CH₂=CHC₂H₄ | Cy | — | Cy | —(CH₂)₂— | Cy | — | H |
| 159 | C₂H₅ | Cy | —(CH₂)₂— | Cy | — | Cy | — | F |
| 160 | C₃H₇ | Cy | — | Cy | — | Ph | — | H |
| 161 | C₅H₁₁ | Cy | — | Cy | — | Ph(F) | — | H |
| 162 | C₂H₅ | Cy | — | Cy | — | Ph | —(CH₂)₂— | F |
| 163 | C₃H₇ | Cy | — | Cy | —(CH₂)₂— | Ph | — | H |
| 164 | C₅H₁₁ | Cy | —(CH₂)₂— | Cy | — | Ph(F) | — | F |
| 165 | C₄H₉ | Cy | — | Ph | — | Ph | — | F |
| 166 | CH₂=CHC₂H₄ | Cy | — | Ph | — | Ph(F) | — | H |
| 167 | CH₃CH₂=CHC₂H₄ | Cy | — | Ph(F,F) | — | Ph | —(CH₂)₂— | H |
| 168 | C₃H₇ | Cy | — | Ph | —(CH₂)₂— | Ph | — | F |
| 169 | C₅H₁₁ | Cy | —(CH₂)₂— | Ph(F) | — | Ph(F) | — | F |
| 170 | CH₃O | Ph | — | Ph | — | Ph | — | F |
| 171 | CH₂=CHC₂H₄ | Ph | — | Ph | — | Ph(F) | — | F |

-continued

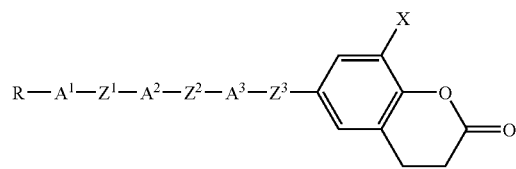

| No. | R | A¹ | Z¹ | A² | Z² | A³ | Z³ | X |
|---|---|---|---|---|---|---|---|---|
| 172 | $C_3H_7$ | phenyl | — | 2-fluorophenyl | — | phenyl | $-(CH_2)_2-$ | F |
| 173 | $CH_2=CHC_2H_4$ | phenyl | — | phenyl | $-(CH_2)_2-$ | phenyl | — | F |
| 174 | $C_3H_7$ | phenyl | $-(CH_2)_2-$ | 2-fluorophenyl | — | 2-fluorophenyl | — | H |

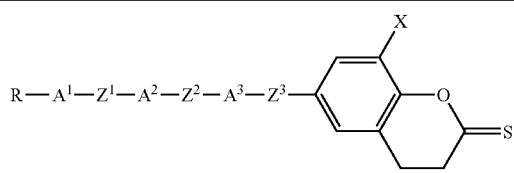

| No. | R | A¹ | Z¹ | A² | Z² | A³ | Z³ | X |
|---|---|---|---|---|---|---|---|---|
| 175 | $C_2H_5$ | cyclohexyl | — | | | | | H |
| 176 | $C_3H_7$ | cyclohexyl | $-(CH_2)_2-$ | | | | | F |
| 177 | $C_2H_5$ | phenyl | — | | | | | H |
| 178 | $C_3H_7$ | 2,3-difluorophenyl | — | | | | | F |
| 179 | $C_3H_7$ | 2-fluorophenyl | $-(CH_2)_2-$ | | | | | F |
| 180 | $CH_2=CHC_2H_4$ | cyclohexyl | — | cyclohexyl | — | | | H |
| 181 | $C_2H_5$ | cyclohexyl | $-(CH_2)_2-$ | cyclohexyl | — | | | F |
| 182 | $C_3H_7$ | cyclohexyl | — | phenyl | — | | | H |

-continued

R—A¹—Z¹—A²—Z²—A³—Z³—[chroman-2-thione with X]

| No. | R | A¹ | Z¹ | A² | Z² | A³ | Z³ | X |
|---|---|---|---|---|---|---|---|---|
| 183 | C₅H₁₁ | cyclohexyl | — | 2-F-phenyl | — | | | F |
| 184 | C₂H₅ | cyclohexyl | —(CH₂)₂— | phenyl | — | | | F |
| 185 | C₃H₇ | cyclohexyl | — | 2-F-phenyl | —(CH₂)₂— | | | H |
| 186 | C₅H₁₁ | phenyl | — | phenyl | — | | | H |
| 187 | C₄H₉ | phenyl | — | 2,3-diF-phenyl | — | | | F |
| 188 | CH₂=CHC₂H₄ | phenyl | —(CH₂)₂— | cyclohexyl | — | | | F |
| 189 | CH₃CH₂=CHC₂H₄ | 2,3-diF-phenyl | — | phenyl | —(CH₂)₂— | | | F |
| 190 | C₃H₇ | cyclohexyl | — | cyclohexyl | — | 2-F-phenyl | — | F |
| 191 | C₅H₁₁ | cyclohexyl | —(CH₂)₂— | 2-F-phenyl | — | 2-F-phenyl | — | F |
| 192 | CH₃O | phenyl | — | phenyl | — | phenyl | — | F |
| 193 | CH₂=CHC₂H₄ | phenyl | — | phenyl | —(CH₂)₂— | 2-F-phenyl | — | H |

Examples of representative compositions of the invention are shown below. The measurement of physical properties was carried out according to methods as described later.

Composition Example 1

Four compounds were mixed to prepare a composition A (matrix liquid crystal) having a nematic phase. The four compounds are as follows.

4-(4-Propylcyclohexyl)benzonitrile (24%)
4-(4-Pentylcyclohexyl)benzonitrile (36%)
4-(4-Heptylcyclohexyl)benzonitrile (25%)
4-(4-Pentylcyclohexyl)-4'-cyanobiphenyl (15%)

Physical properties of the composition A are as follows. Upper limit temperature (NI)=71.7° C., viscosity ($\eta_{20}$)=27.0 mPa·s, optical anisotropy ($\Delta n$)=0.137, and dielectric anisotropy ($\Delta \epsilon$)=11.0.

10% by weight of the 6-(4-(4-propylcyclohexyl)phenyl)-3,4-dihydrocoumarin as described in Example 2 was added to this composition A, and physical properties of the mixture were measured. The results obtained are as follows. Upper limit temperature (NI)=80.4° C., optical anisotropy ($\Delta n$)=0.143, and dielectric anisotropy ($\Delta \epsilon$)=11.4.

In addition, representative compositions of the invention are summarized in Composition Examples 2 to 13. First of all, compounds as components of a composition and their amounts (% by weight) are shown. Each of the compounds is expressed with symbols of the left terminal group, the bonding group, the ring structure and the right terminal group according to the agreement of the following Table 1.

TABLE 1

R—($A_1$)—$Z_1$— $\cdots$ —$Z_n$—($A_n$)—X

| 1) Left terminal group R— | Symbol |
|---|---|
| $C_nH_{2n+1}$— | n— |
| $C_nH_{2n+1}OC_mH_{2m}$— | nOm— |
| $CH_2$=CH— | V— |
| $C_nH_{2n+1}CH$=CH— | nV— |
| $CH_2$=$CHC_nH_{2n}$— | Vn— |
| $C_nH_{2n+1}CH$=$CHC_mH_{2m}$— | nVm— |
| $CF_2$=CH— | VFF— |
| $CF_2$=$CHC_nH_{2n}$— | VFFn— |

| 2) Ring structure —$A_n$— | Symbol |
|---|---|
| 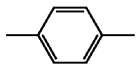 | B |
| 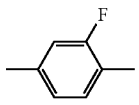 | B(F) |
| 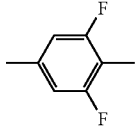 | B(F,F) |
| 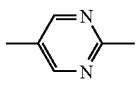 | Py |
| 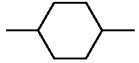 | H |

TABLE 1-continued

| | |
|---|---|
| 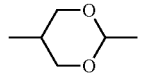 | G |
| 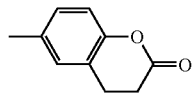 | Cro=O |
| 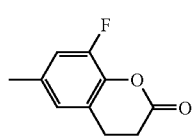 | Cro(F)=O |

| 3) Bonding group —$Z_n$— | Symbol |
|---|---|
| —$C_2H_4$— | 2 |
| —$C_4H_8$— | 4 |
| —CH=CH— | V |
| —COO— | E |
| —C≡C— | T |
| —$CF_2O$— | X |

| 4) Right terminal group —X | Symbol |
|---|---|
| —F | —F |
| —Cl | —CL |
| —CN | —C |
| —$OCF_2H$ | —OCF2H |
| —$OCF_3$ | —OCF3 |
| —$CF_3$ | —CF3 |
| —$C_nH_{2n+1}$ | —n |
| —$OC_nH_{2n+1}$ | —On |
| —CH=$CH_2$ | —V |
| —$C_nH_{2n}CH$=$CH_2$ | —nV |
| —$C_nH_{2n}CH$=$CHC_mH_{2m+1}$ | —nVm |
| —CH=$CF_2$ | —VFF |
| —$COOCH_3$ | —EMe |

5) Examples of expression

Example 1: 2-BEB(F)-C

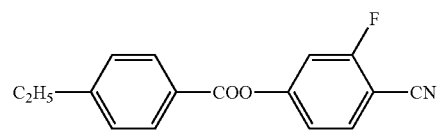

Example 2: 101-HBBH-5

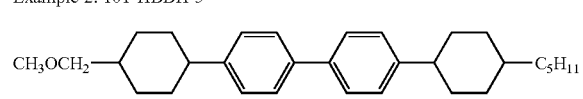

Example 3: 3-HBCro=O

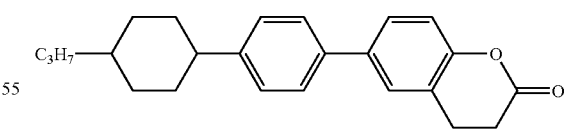

The stereospecific configuration of each of 1,4-cyclohexylene and 1,3-dioxane-2,5-diyl is a trans-configuration. The case where no symbol of the terminal group is given means that the terminal group is hydrogen. Next, physical properties of each of the compositions are shown. The measurement of the physical properties was carried out according to a method as described in EIAJ•ED-2521A of Standard of Electronic Industries Association of Japan or a modified method thereof.

<Upper Limit Temperature (NI; ° C.) of Nematic Phase>

A sample was placed on a hot plate of a melting point analyzer equipped with a polarizing microscope and heated at a rate of 1° C./min. At the time when a part of the sample changed from a nematic phase to an isotropic liquid, the temperature was measured. The upper limit temperature of the nematic phase may be abbreviated as "upper limit temperature".

<Lower Limit Temperature ($T_c$; ° C.) of Nematic Phase>

A sample having a nematic phase was stored in a freezer at 0° C., −10° C., −20° C., −30° C., or −40° C. for 10 days, and its liquid crystal phase was then observed. For example, when the sample keeps a nematic phase at −20° C. but changes to a crystal (or a smectic phase) at −30° C., $T_c$ is expressed as "<−20° C.". The lower limit temperature of the nematic phase may be abbreviated as "lower limit temperature".

<Compatibility of Compound>

Some compounds having an analogous structure were mixed to prepare a matrix liquid crystal having a nematic phase. A compound to be measured was mixed with this matrix liquid crystal to obtain a composition. One example of the mixing proportion is a combination of 15% of the compound and 85% of the matrix liquid crystal. This composition was stored at a low temperature, for example, −20° C. or −30° C. for 30 days. Whether or not a part of this composition changed to a crystal (or a smectic phase) was observed. If necessary, the mixing proportion and storage temperature were varied. From the results obtained by the measurement, a condition under which a crystal (or a smectic phase) was deposited and a condition under which a crystal (or a smectic phase) was not deposited were determined. These conditions are a scale of compatibility.

<Viscosity ($\eta$; Measured at 20° C.; mPa·s)>

In measuring the viscosity, an E type viscometer was used.

<Optical Anisotropy (Refractive Index Anisotropy; $\Delta n$; Measured at 25° C.)>

The measurement was carried out by an Abbe refractometer having a polarizing plate equipped in an eyepiece using light having a wavelength of 589 nm. After rubbing the surface of a major prism in one direction, a sample was added dropwise on the major prism. A refractive index n∥ was measured when the direction of polarization was parallel to the direction of rubbing. A refractive index n⊥ was measured when the direction of polarization was vertical to the direction of rubbing. A value of the optical anisotropy was calculated according to an expression, ($\Delta n$=n∥−n⊥). When a sample was a composition, the optical anisotropy was measured by this method. When a sample was a compound, the optical anisotropy was measured after mixing the compound with an adequate composition. The optical anisotropy of the compound is an extrapolation value.

<Dielectric Anisotropy ($\Delta\epsilon$; Measured at 25° C.)>

When a sample was a compound, the dielectricl anisotropy was measured after mixing the compound with an adequate composition. The dielectric anisotropy of the compound is an extrapolation value.

(1) Composition in which the Dielectric Anisotropy is Positive:

A sample was charged in a liquid crystal cell in which a gap between two glass substrates was about 9 μm and a twisted angle was 80°. 20 V was applied to this cell, thereby measuring a dielectric constant (ε∥) in the major axis direction of the liquid crystal molecule. 0.5 V was applied, thereby measuring a dielectric constant (ε⊥) in the minor axis direction of the liquid crystal molecule. A value of the dielectric anisotropy was calculated according to an expression, ($\Delta\epsilon$=ε∥−ε⊥).

(2) Composition in which the Dielectric Anisotropy is Negative:

A sample was charged in a liquid crystal cell having been subjected to a homeotropic orientation treatment, and 0.5 V was applied thereto, thereby measuring a dielectric constant (ε∥). A sample was charged in a liquid crystal cell having been subjected to a homogenous orientation treatment, and 0.5 V was applied thereto, thereby measuring a dielectric constant (ε⊥). A value of the dielectric anisotropy was calculated according to an expression, ($\Delta\epsilon$=ε∥−ε⊥).

<Threshold Voltage (Vth; Measured at 25° C.; V)>

When a sample was a compound, the threshold voltage was measured after mixing the compound with an adequate composition. The threshold voltage of the compound is an extrapolation value.

(1) Composition in which the Dielectric Anisotropy is Positive:

A sample was charged in a liquid crystal display device of a normally white mode in which a gap between two glass substrates was (0.5/$\Delta n$) μm and a twisted angle was 80°. The $\Delta n$ is a value of optical anisotropy measured by the foregoing method. A rectangular wave having a frequency of 32 Hz was applied to this device. A value of a voltage was measured at the time when the voltage of the rectangular wave was increased and a transmittance of light passing through the device reached 90%.

(2) Composition in which the Dielectric Anisotropy is Negative:

A sample was charged in a liquid crystal display device of a normally black mode having been subjected to a homeotropic orientation treatment, in which a gap between two glass substrates was about 9 μm. Rectangular wave having a frequency of 32 Hz was applied to the device. A value of a voltage was measured at the time when the voltage of the rectangular wave was increased and a transmittance of light passing through the device reached 10%.

Composition Example 2

| | |
|---|---|
| 3-HBCro=O: | 3% |
| 3-HHCro=O: | 3% |
| 2-BEB(F)—C: | 5% |
| 3-BEB(F)—C: | 4% |
| 4-BEB(F)—C: | 12% |
| 1V2-BEB(F,F)—C: | 16% |
| 3-HB—O2: | 10% |
| 3-HH-4: | 3% |
| 3-HHB—F: | 3% |
| 3-HHB-1: | 8% |
| 3-HHB—O1: | 4% |
| 3-HBEB—F: | 4% |
| 3-HHEB—F: | 4% |
| 5-HHEB—F: | 4% |
| 3-H2BTB-2: | 4% |
| 3-H2BTB-3: | 4% |
| 3-H2BTB-4: | 4% |
| 3-HB(F)TB-2: | 5% |

NI=89.6° C., $\Delta n$=0.147, $\Delta\epsilon$=28.4, Vth =1.05 V.

Composition Example 3

| | |
|---|---|
| 3-HHCro(F)=O: | 5% |
| 2-HB—C: | 5% |
| 3-HB—C: | 12% |
| 3-HB—O2: | 15% |
| 2-BTB-1: | 3% |
| 3-HHB—F: | 4% |
| 3-HHB-1: | 8% |
| 3-HHB—O1: | 5% |
| 3-HHB-3: | 9% |
| 3-HHEB—F: | 4% |
| 5-HHEB—F: | 4% |
| 2-HHB(F)—F: | 7% |
| 3-HHB(F)—F: | 7% |
| 5-HHB(F)—F: | 7% |
| 3-HHB(F,F)—F: | 5% |

Composition Example 4

| | |
|---|---|
| 3-BB(F)Cro=O: | 3% |
| 3-B(F)B(F)Cro=O: | 4% |
| 3-BB(F)Cro(F)=O: | 3% |
| 3-BEB(F)—C: | 8% |
| 3-HB—C: | 8% |
| V-HB—C: | 8% |
| 1V-HB—C: | 8% |
| 3-HB—O2: | 3% |
| 3-HH-2V: | 14% |
| 3-HH-2V1: | 7% |
| V2-HHB-1: | 7% |
| 3-HHB-1: | 5% |
| 3-HHEB—F: | 7% |
| 3-H2BTB-2: | 5% |
| 3-H2BTB-3: | 5% |
| 3-H2BTB-4: | 5% |

Composition Example 5

| | |
|---|---|
| 3-HBCro=O: | 3% |
| 3-HB(F)Cro(F)=O: | 4% |
| 5-BEB(F)—C: | 5% |
| V-HB—C: | 11% |
| 5-PyB—C: | 6% |
| 4-BB-3: | 11% |
| 3-HH-2V: | 10% |
| 5-HH-V: | 11% |
| V-HHB-1: | 5% |
| V2-HHB-1: | 10% |
| 3-HHB-1: | 9% |
| 1V2-HBB-2: | 10% |
| 3-HHEBH-3: | 5% |

Composition Example 6

| | |
|---|---|
| 3-H2HCro(F)=O: | 5% |
| 3-BB(F)2Cro=O: | 5% |
| 1V2-BEB(F,F)—C: | 6% |
| 3-HB—C: | 18% |
| 2-BTB-1: | 10% |
| 5-HH-VFF: | 30% |
| 3-HHB-1: | 3% |
| VFF-HHB-1: | 5% |
| VFF2-HHB-1: | 6% |
| 3-H2BTB-2: | 4% |
| 3-H2BTB-3: | 4% |
| 3-H2BTB-4: | 4% |

Composition Example 7

| | |
|---|---|
| 3-HBCro=O: | 3% |
| 2-HHCro=O: | 5% |
| 5-HB—CL: | 16% |
| 3-HH-4: | 12% |
| 3-HH-5: | 4% |
| 3-HHB—F: | 4% |
| 3-HHB—CL: | 3% |
| 4-HHB—CL: | 4% |
| 3-HHB(F)—F: | 7% |
| 4-HHB(F)—F: | 7% |
| 5-HHB(F)—F: | 7% |
| 7-HHB(F)—F: | 7% |
| 5-HBB(F)—F: | 4% |
| 1O1-HBBH-5: | 3% |
| 3-HHBB(F,F)—F: | 2% |
| 4-HHBB(F,F)—F: | 3% |
| 5-HHBB(F,F)—F: | 3% |
| 3-HH2BB(F,F)—F: | 3% |
| 4-HH2BB(F,F)—F: | 3% |

NI=119.5° C., Δn=0.097, Δε=3.9, Vth =2.70 V.

When 0.25 parts of Op05 was added to 100 parts of the foregoing composition, a pitch was 60.5 μm.

Composition Example 8

| | |
|---|---|
| 3-HHCro(F)=O: | 3% |
| 3-H2HCro(F)=O: | 3% |
| 3-HHB(F,F)—F: | 9% |
| 3-H2B(F,F)—F: | 8% |
| 4-H2HB(F,F)—F: | 8% |
| 5-H2HB(F,F)—F: | 8% |
| 3-HBB(F,F)—F: | 18% |
| 5-HBB(F,F)—F: | 18% |
| 3-H2BB(F,F)—F: | 10% |
| 5-HHBB(F,F)—F: | 3% |
| 5-HHEBB—F: | 3% |
| 3-HH2BB(F,F)—F: | 2% |
| 1O1-HBBH-4: | 3% |
| 1O1-HBBH-5: | 4% |

Composition Example 9

| | |
|---|---|
| 3-BB(F)Cro=O: | 3% |
| 3-BB(F)2Cro=O: | 4% |
| 5-HB—F: | 12% |
| 6-HB—F: | 9% |
| 7-HB—F: | 7% |
| 2-HHB—OCF3: | 7% |
| 3-HHB—OCF3: | 7% |
| 4-HHB—OCF3: | 7% |
| 5-HHB—OCF3: | 5% |
| 3-HH2B—OCF3: | 4% |
| 5-HH2B—OCF3: | 4% |
| 3-HHB(F,F)—OCF2H: | 4% |
| 3-HHB(F,F)—OCF3: | 5% |
| 3-HH2B(F)—F: | 3% |
| 3-HBB(F)—F: | 6% |
| 5-HBB(F)—F: | 7% |
| 5-HBBH-3: | 3% |
| 3-HB(F)BH-3: | 3% |

Composition Example 10

| | |
|---|---|
| 3-B(F)B(F)Cro=O: | 3% |
| 3-BB(F)Cro(F)=O: | 4% |
| 3-HB(F)Cro(F)=O: | 3% |
| 5-HB—CL: | 11% |
| 3-HH-4: | 8% |
| 3-HHB-1: | 5% |
| 3-HHB(F,F)—F: | 8% |
| 3-HBB(F,F)—F: | 12% |
| 5-HBB(F,F)—F: | 13% |
| 3-HHEB(F,F)—F: | 10% |
| 4-HHEB(F,F)—F: | 3% |
| 5-HHEB(F,F)—F: | 3% |
| 2-HBEB(F,F)—F: | 3% |
| 3-HBEB(F,F)—F: | 5% |
| 5-HBEB(F,F)—F: | 3% |
| 3-HHBB(F,F)—F: | 6% |

Composition Example 11

| | |
|---|---|
| 3-HHCro=O: | 5% |
| 3-HHCro(F)=O: | 5% |
| 3-HB—CL: | 6% |
| 5-HB—CL: | 4% |
| 3-HHB—OCF3: | 5% |
| 3-H2HB—OCF3: | 5% |
| 5-H4HB—OCF3: | 15% |
| V-HHB(F)—F: | 4% |
| 3-HHB(F)—F: | 3% |
| 5-HHB(F)—F: | 3% |
| 3-H4HB(F,F)—CF3: | 8% |
| 5-H4HB(F,F)—CF3: | 10% |
| 5-H2HB(F,F)—F: | 5% |
| 5-H4HB(F,F)—F: | 7% |
| 2-H2BB(F)—F: | 4% |
| 3-H2BB(F)—F: | 7% |
| 3-HBEB(F,F)—F: | 4% |

Composition Example 12

| | |
|---|---|
| 3-BB(F)Cro=O: | 4% |
| 3-BB(F)Cro(F)=O: | 4% |
| 5-HB—CL: | 17% |
| 7-HB(F,F)—F: | 3% |
| 3-HH-4: | 10% |
| 3-HH-5: | 5% |
| 3-HB—O2: | 12% |
| 3-HHB-1: | 6% |
| 3-HHB—O1: | 4% |
| 2-HHB(F)—F: | 6% |
| 3-HHB(F)—F: | 6% |
| 5-HHB(F)—F: | 6% |
| 3-HHB(F,F)—F: | 7% |
| 3-H2HB(F,F)—F: | 5% |
| 4-H2HB(F,F)—F: | 5% |

Composition Example 13

| | |
|---|---|
| 3-B(F)B(F)Cro=O: | 3% |
| 3-BB(F)2Cro=O: | 5% |
| 5-HB—CL: | 3% |
| 7-HB(F)—F: | 7% |
| 3-HH-4: | 9% |
| 3-HH—EMe: | 15% |
| 3-HHEB—F: | 8% |
| 5-HHEB—F: | 8% |
| 3-HHEB(F,F)—F: | 10% |
| 4-HHEB(F,F)—F: | 5% |
| 4-HGB(F,F)—F: | 5% |
| 5-HGB(F,F)—F: | 6% |

-continued

| | |
|---|---|
| 2-H2GB(F,F)—F: | 4% |
| 3-H2GB(F,F)—F: | 5% |
| 5-GHB(F,F)—F: | 7% |

Composition Example 14

| | |
|---|---|
| 3-HB(F)Cro(F)=O: | 4% |
| 3-H2HCro(F)=O: | 5% |
| 3-HH-4: | 8% |
| 3-HHB-1: | 6% |
| 3-HHB(F,F)—F: | 10% |
| 3-H2HB(F,F)—F: | 9% |
| 3-HBB(F,F)—F: | 10% |
| 3-BB(F,F)XB(F,F)—F: | 32% |
| 1O1-HBBH-5: | 7% |
| 2-HHBB(F,F)—F: | 3% |
| 3-HHBB(F,F)—F: | 3% |
| 3-HH2BB(F,F)—F: | 3% |

INDUSTRIAL APPLICABILITY

The compound of the invention has general physical properties necessary for a compound, stability against heat, light, etc., adequate optical anisotropy, adequate dielectric anisotropy and excellent compatibility with other liquid crystalline compounds. The liquid crystal composition of the invention contains at least one of these compounds and has a high upper limit temperature of a nematic phase, a low lower limit temperature of a nematic phase, a low viscosity, adequate optical anisotropy and a low threshold voltage. The liquid crystal display device of the invention contains this composition and has a wide useful temperature range, a short response time, a large contrast ratio and a low drive voltage.

The invention claimed is:

1. A compound represented by the following formula (1):

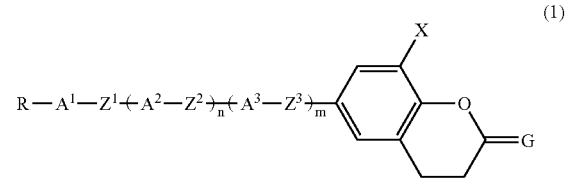

wherein

R represents an alkyl having from 1 to 20 carbon atoms; and in this alkyl, any —CH$_2$— may be replaced by —O—, —S—, —CO—, —CH=CH—, or —C≡C—;

$A^1$, $A^2$, and $A^3$ each independently represents 1,4-cyclohexylene or 1,4-phenylene; in the 1,4-cyclohexylene, any —CH$_2$— may be replaced by —O—, —S—, or —CO—, and any —(CH$_2$)$_2$— may be replaced by —CH=CH—; in the 1,4-phenylene, any —CH— may be replaced by —N=; and in these rings, any hydrogen may be replaced by fluorine, chlorine, —CN, —CF$_3$, —CHF$_2$, —CH$_2$F, —OCF$_3$, —OCHF$_2$, or —OCH$_2$F;

$Z^1$, $Z^2$, and $Z^3$ each independently represents a single bond, —(CH$_2$)$_2$—, —CH$_2$O—, —OCH$_2$—, —CF$_2$O—, —OCF$_2$—, —CH=CH—, —CF=CF—, —C≡C—, —(CH$_2$)$_4$—, —O(CH$_2$)$_2$O—, —(CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—CH$_2$O—, or —OCH$_2$—CH=CH—;

X represents hydrogen, fluorine, chlorine, —CN, —CF$_3$, —CHF$_2$, —CH$_2$F, —OCF$_3$, —OCHF$_2$, or —OCH$_2$F;

G represents oxygen or sulfur;

n and m each independently represents 0, 1, or 2; and in any one of the following (i) to (iii), R may represent hydrogen:

(i) the total sum of n and m is 1 or 2;

(ii) X represents fluorine, chlorine, —CN, —CF$_3$, —CHF$_2$, —CH$_2$F, —OCF$_3$, —OCHF$_2$, or —OCH$_2$F; and (iii) at least one of A$^1$, A$^2$, and A$^3$ represents 1,4-phenylene in which any hydrogen is replaced by fluorine, chlorine, —CN, —CF$_3$, —CHF$_2$, —CH$_2$F, —OCF$_3$, —OCHF$_2$, or —OCH$_2$F.

2. A compound represented by the following formula (1):

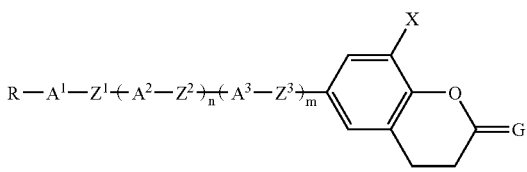

(1)

wherein

R represents an alkyl having from 1 to 15 carbon atoms, an alkoxy having from 1 to 15 carbon atoms, an alkoxyalkyl having from 2 to 15 carbon atoms, or an alkenyl having from 2 to 15 carbon atoms;

A$^1$, A$^2$, and A$^3$ each independently represents 1,4-cyclohexylene, 1,4-phenylene, fluorinated 1,4-phenylene, or 1,3-dioxane-2,5-diyl;

G represents oxygen or sulfur;

Z$^1$, Z$^2$, and Z$^3$ each independently represents a single bond, —(CH$_2$)$_2$—, —CH$_2$O—, or —OCH$_2$—, X represents fluorine or hydrogen;

n and m each independently represents 0 or 1; and in any one of the following (iv) to (vi), R may represents hydrogen:

(iv) the total sum of n and m is 1 or 2;

(v) X represents fluorine; and (vi) at least one of A$^1$, A$^2$, and A$^3$ represents 1,4-phenylene in which any hydrogen is replaced by fluorine.

3. The compound according to claim 2, wherein G represents oxygen; and Z$^1$, Z$^2$, and Z$^3$ each represents a single bond.

4. The compound according to claim 2, wherein G represents oxygen; Z$^1$, Z$^2$, and Z$^3$ each represents a single bond; and A$^1$, A$^2$, and A$^3$ each independently represents 1,4-cyclohexylene, 1,4-phenylene, or fluorinated 1,4-phenylene.

5. The compound according to claim 2, wherein G represents oxygen; Z$^1$, Z$^2$, and Z$^3$ each represents a single bond; A$^1$, A$^2$, and A$^3$ each independently represents 1,4-cyclohexylene, 1,4-phenylene, or fluorinated 1,4-phenylene; and R represents an alkyl having from 1 to 15 carbon atoms.

6. The compound according to claim 5, wherein any one of A$^1$, A$^2$, and A$^3$ represents fluorinated 1,4-phenylene.

7. The compound according to claim 2, wherein G represents oxygen; Z$^1$, Z$^2$, and Z$^3$ each represents a single bond; A$^1$, A$^2$, and A$^3$ each independently represents 1,4-cyclohexylene, 1,4-phenylene, or fluorinated 1,4-phenylene; and R represents an alkenyl having from 2 to 15 carbon atoms.

8. The compound according to claim 7, wherein any one of A$^1$, A$^2$, and A$^3$ represents fluorinated 1,4-phenylene.

9. The compound according to claim 2, wherein G represents oxygen; Z$^1$, Z$^2$, and Z$^3$ each represents a single bond; and any one of A$^1$, A$^2$, and A$^3$ represents 1,4-cyclohexylene.

10. The compound according to claim 2, wherein G represents oxygen; and any one of Z$^1$, Z$^2$, and Z$^3$ represents —CH$_2$O— or —OCH$_2$—.

11. The compound according to claim 2, wherein G represents oxygen; any one of Z$^1$, Z$^2$, and Z$^3$ represents —CH$_2$O— or —OCH$_2$—; and A$^1$, A$^2$, and A$^3$ each independently represents 1,4-cyclohexylene, 1,4-phenylene, or fluorinated 1,4-phenylene.

12. The compound according to claim 2, wherein G represents oxygen; and any one of Z$^1$, Z$^2$, and Z$^3$ represents —(CH$_2$)$_2$—.

13. The compound according to claim 2, wherein G represents oxygen; any one of Z$^1$, Z$^2$, and Z$^3$ represents —(CH$_2$)$_2$—; and A$^1$, A$^2$, and A$^3$ each independently represents 1,4-cyclohexylene, 1,4-phenylene, or fluorinated 1,4-phenylene.

14. The compound according to claim 2, wherein G represents oxygen; any one of Z$^1$, Z$^2$, and Z$^3$ represents —(CH$_2$)$_2$—; A$^1$, A$^2$, and A$^3$ each independently represents 1,4-cyclohexylene, 1,4-phenylene, or fluorinated 1,4-phenylene; and R represents an alkyl having from 1 to 15 carbon atoms.

15. The compound according to claim 14, wherein any one of A$^1$, A$^2$, and A$^3$ represents fluorinated 1,4-phenylene.

16. The compound according to claim 2, wherein G represents oxygen; any one of Z$^1$, Z$^2$, and Z$^3$ represents —(CH$_2$)$_2$—; A$^1$, A$^2$, and A$^3$ each independently represents 1,4-cyclohexylene, 1,4-phenylene, or fluorinated 1,4-phenylene; and R represents an alkenyl having from 2 to 15 carbon atoms.

17. The compound according to claim 16, wherein any one of A$^1$, A$^2$, and A$^3$ represents fluorinated 1,4-phenylene.

18. The compound according to claim 2, wherein G represents sulfur.

19. A compound represented by any one of the following formulae (1a) to (1m):

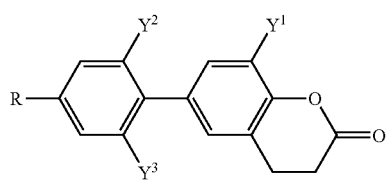

1a

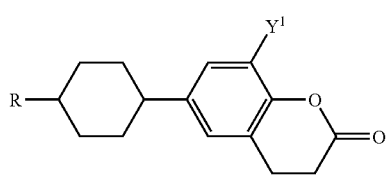

1b

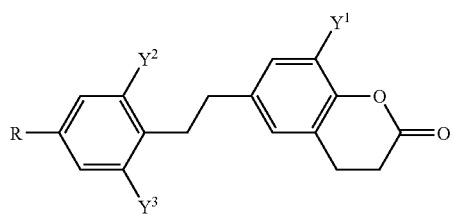

1c

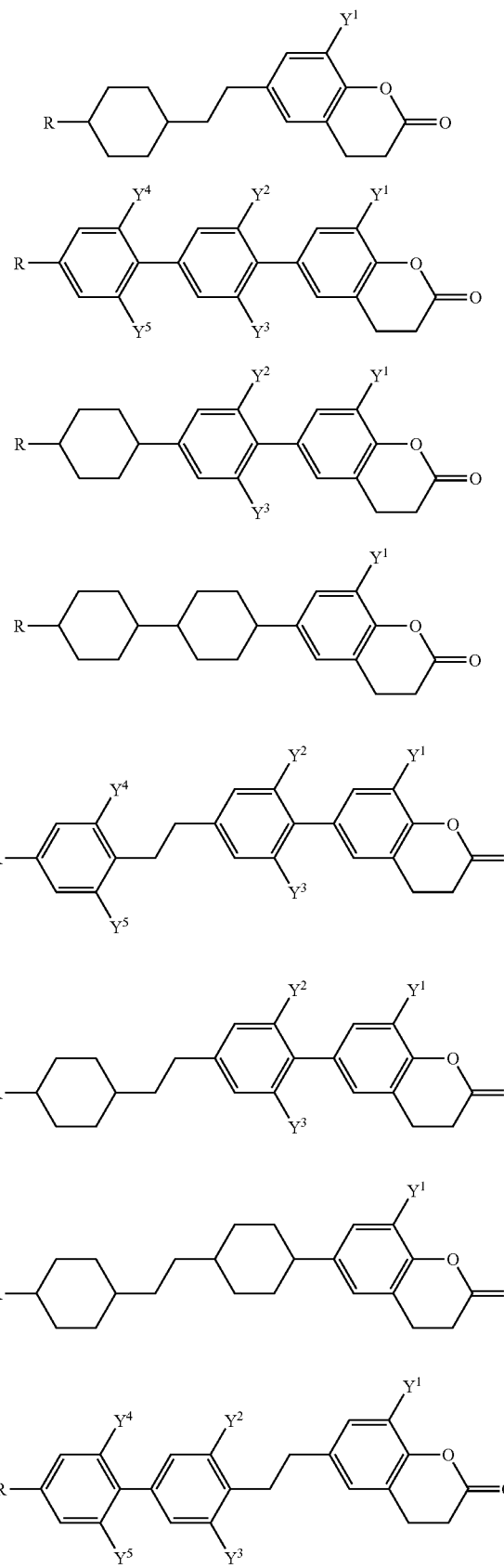

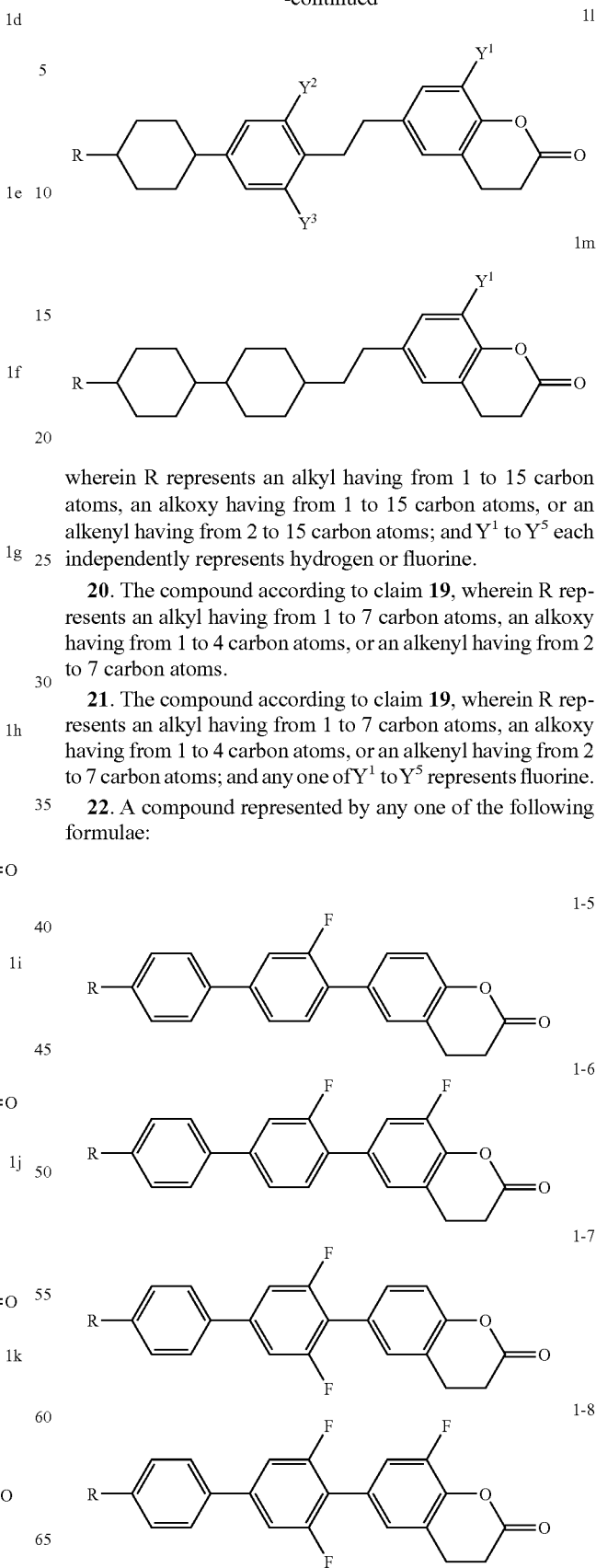

wherein R represents an alkyl having from 1 to 15 carbon atoms, an alkoxy having from 1 to 15 carbon atoms, or an alkenyl having from 2 to 15 carbon atoms; and $Y^1$ to $Y^5$ each independently represents hydrogen or fluorine.

20. The compound according to claim 19, wherein R represents an alkyl having from 1 to 7 carbon atoms, an alkoxy having from 1 to 4 carbon atoms, or an alkenyl having from 2 to 7 carbon atoms.

21. The compound according to claim 19, wherein R represents an alkyl having from 1 to 7 carbon atoms, an alkoxy having from 1 to 4 carbon atoms, or an alkenyl having from 2 to 7 carbon atoms; and any one of $Y^1$ to $Y^5$ represents fluorine.

22. A compound represented by any one of the following formulae:

-continued
1-12
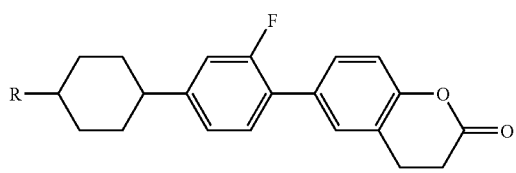
1-13
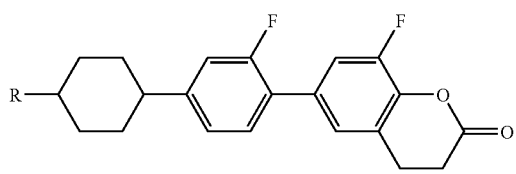
1-14
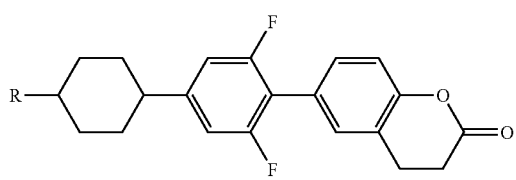
1-15
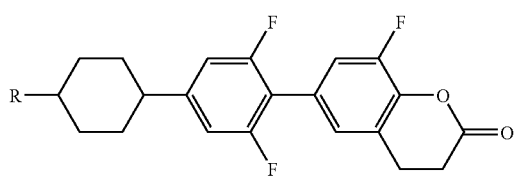
1-16
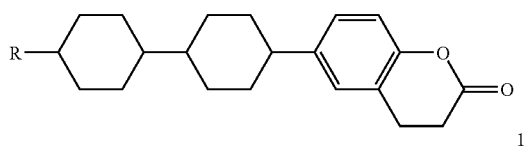
1-17
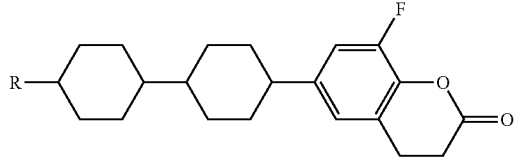
1-22
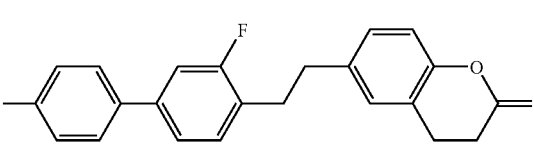
1-23
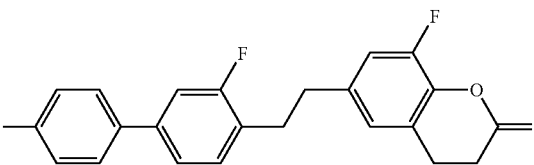
-continued
1-24
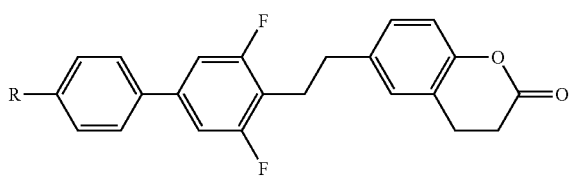
1-25
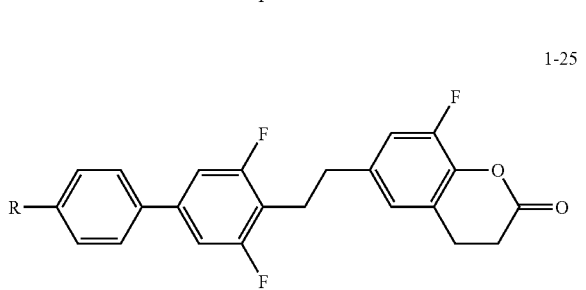
1-29
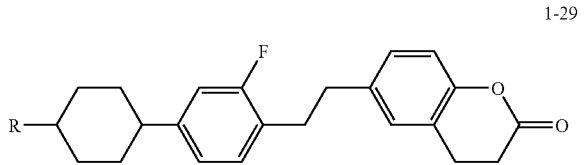
1-30
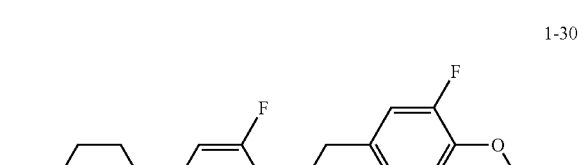
1-31
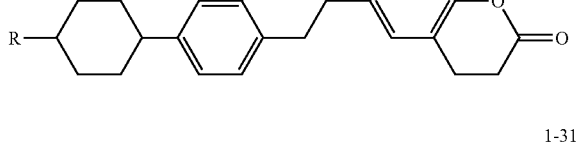
1-32
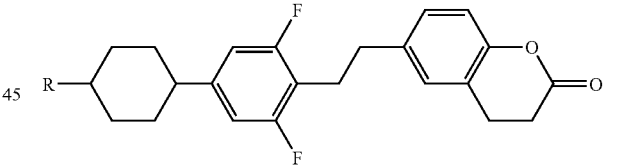
1-33
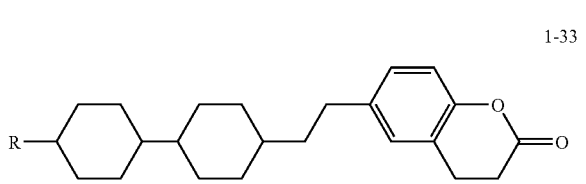

-continued 1-34

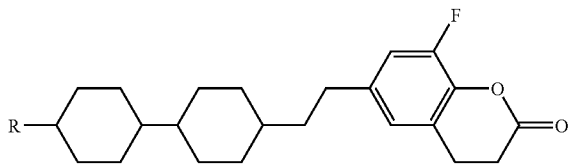

wherein R represents an alkyl having from 1 to 7 carbon atoms, an alkoxy having from 1 to 4 carbon atoms, or an alkenyl having from 2 to 7 carbon atoms.

23. A liquid crystal composition containing at least one compound according to claim 1 and comprising at least two compounds.

24. The liquid crystal composition according to claim 23, containing at least one compound selected from the group consisting of compounds represented by the following formulae (2), (3) and (4):

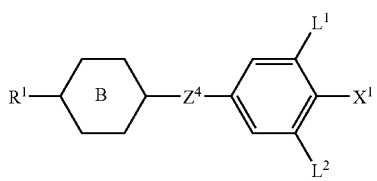
(2)

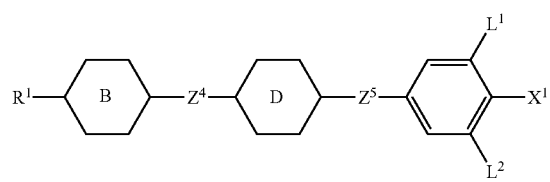
(3)

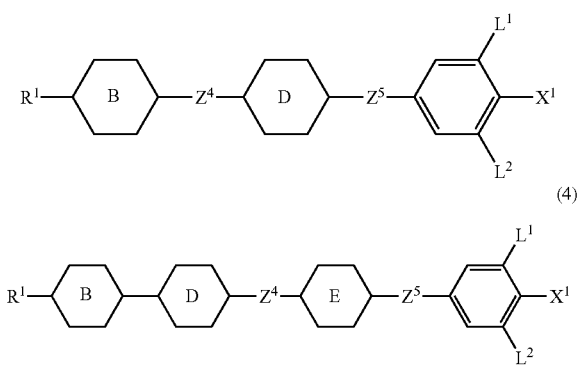
(4)

wherein
   $R^1$ represents an alkyl having from 1 to 10 carbon atoms; and in this alkyl, any —$CH_2$— may be replaced by —O— or —CH=CH—, and any hydrogen may be replaced by fluorine;
   $X^1$ represents fluorine, chlorine, —$OCF_3$, —$OCHF_2$, —$CF_3$, —$CHF_2$, —$CH_2F$, —$OCF_2CHF_2$, or —$OCF_2CHFCF_3$;
   ring B and ring D each independently represents 1,4-cyclohexylene, 1,3-dioxane-2,5-diyl, or 1,4-phenylene in which any hydrogen is replaced by fluorine;
   ring E represents 1,4-cyclohexylene, or 1,4-phenylene in which any hydrogen is replaced by fluorine;
   $Z^4$ and $Z^5$ each independently represents —$(CH_2)_2$—, —$(CH_2)_4$—, —COO—, —$CF_2O$—, —$OCF_2$—, —CH=CH—, or a single bond; and
   $L^1$ and $L^2$ each independently represents hydrogen or fluorine.

25. The liquid crystal composition according to claim 23, containing at least one compound selected from the group consisting of compounds represented by the following formulae (5) and (6):

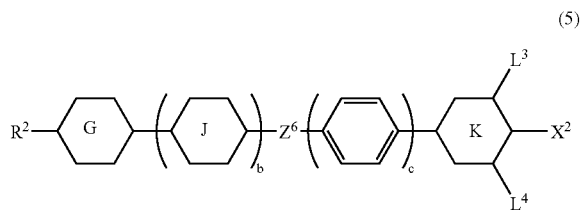
(5)

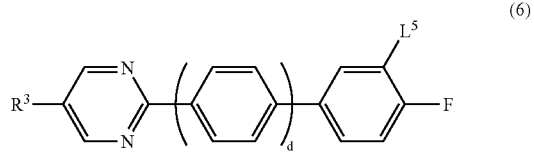
(6)

wherein
   $R^2$ and $R^3$ each independently represents an alkyl having from 1 to 10 carbon atoms; and in this alkyl, any —$CH_2$— may be replaced by —O— or —CH=CH—, and any hydrogen may be replaced by fluorine;
   $X^2$ represents —CN or —C≡C—CN;
   ring G represents 1,4-cyclohexylene, 1,4-phenylene, 1,3-dioxane-2,5-diyl, or pyrimidine-2,5-diyl;
   ring J represents 1,4-cyclohexylene, pyrimidine-2,5-diyl, or 1,4-phenylene in which any hydrogen is replaced by fluorine;
   ring K represents 1,4-cyclohexylene or 1,4-phenylene;
   $Z^6$ represents —$(CH_2)_2$—, —COO—, —$CF_2O$—, —$OCF_2$—, or a single bond;
   $L^3$, $L^4$, and $L^5$ each independently represents hydrogen or fluorine; and
   b, c, and d each independently represents 0 or 1.

26. The liquid crystal composition according to claim 23, containing at least one compound selected from the group consisting of compounds represented by the following formulae (7), (8), (9), (10) and (11):

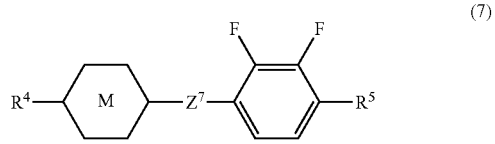
(7)

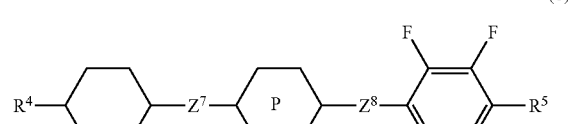
(8)

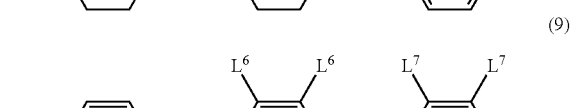
(9)

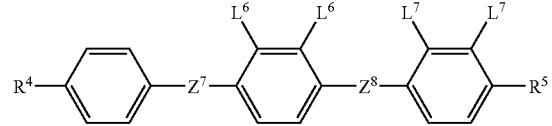

-continued

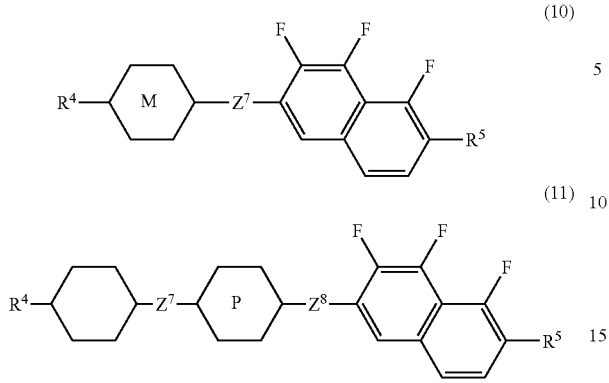

wherein

R[4] represents an alkyl having from 1 to 10 carbon atoms; and in this alkyl, any —CH$_2$— may be replaced by —O— or —CH═CH—, and any hydrogen may be replaced by fluorine;

R[5] represents fluorine or an alkyl having from 1 to 10 carbon atoms; and in this alkyl, any —CH$_2$— may be replaced by —O— or —CH═CH—, and any hydrogen may be replaced by fluorine;

ring M and ring P each independently represents 1,4-cyclohexylene, 1,4-phenylene, or decahydro-2,6-naphthylene;

Z[7] and Z[8] each independently represents —(CH$_2$)$_2$—, —COO—, or a single bond; and L[6] and L[7] each independently represents hydrogen or fluorine, and at least one of L[6] and L[7] represents fluorine.

27. The liquid crystal composition according to claim 23, containing at least one compound selected from the group consisting of compounds represented by the following formulae (12), (13) and (14):

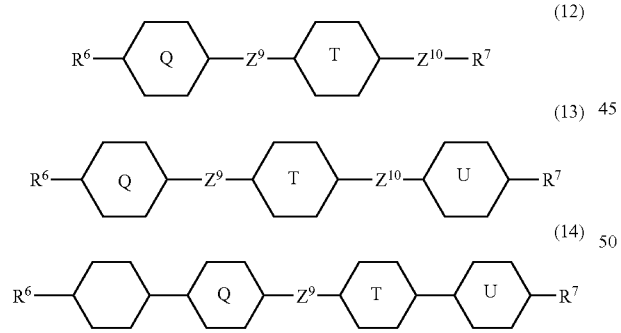

wherein

R[6] and R[7] each independently represents an alkyl having from 1 to 10 carbon atoms; and in this alkyl, any —CH$_2$— may be replaced by —O— or —CH═CH—, and any hydrogen may be replaced by fluorine;

ring Q, ring T, and ring U each independently represents 1,4-cyclohexylene, pyrimidine-2,5-diyl, or fluorinated 1,4-phenylene in which any hydrogen is replaced by fluorine; and Z[9] and Z[10] each independently represents —C≡C—, —COO—, —(CH$_2$)$_2$—, —CH═CH—, or a single bond.

28. The liquid crystal composition according to claim 24, containing at least one compound selected from the group consisting of compounds represented by the formulae (5) and (6):

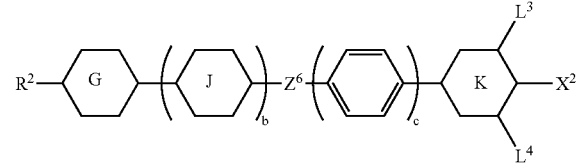

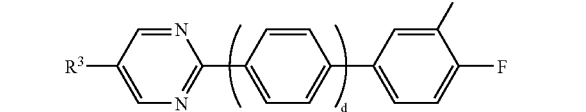

wherein

R[2] and R[3] each independently represents an alkyl having from 1 to 10 carbon atoms; and in this alkyl, any —CH$_2$— may be replaced by —O— or —CH═CH—, and any hydrogen may be replaced by fluorine;

X[2] represents —CN or —C≡C—CN;

ring G represents 1,4-cyclohexylene, 1,4-phenylene, 1,3-dioxane-2,5-diyl, or pyrimidine-2,5-diyl;

ring J represents 1,4-cyclohexylene, pyrimidine-2,5-diyl, or 1,4-phenylene in which any hydrogen is replaced by fluorine;

ring K represents 1,4-cyclohexylene or 1,4-phenylene;

Z[6] represents —(CH$_2$)$_2$—, —COO—, —CF$_2$O—, —OCF$_2$—, or a single bond;

L[3], L[4], and L[5] each independently represents hydrogen or fluorine; and b, c, and d each independently represents 0 or 1.

29. The liquid crystal composition according to claim 24, containing at least one compound selected from the group consisting of compounds represented by the formulae (12), (13) and (14):

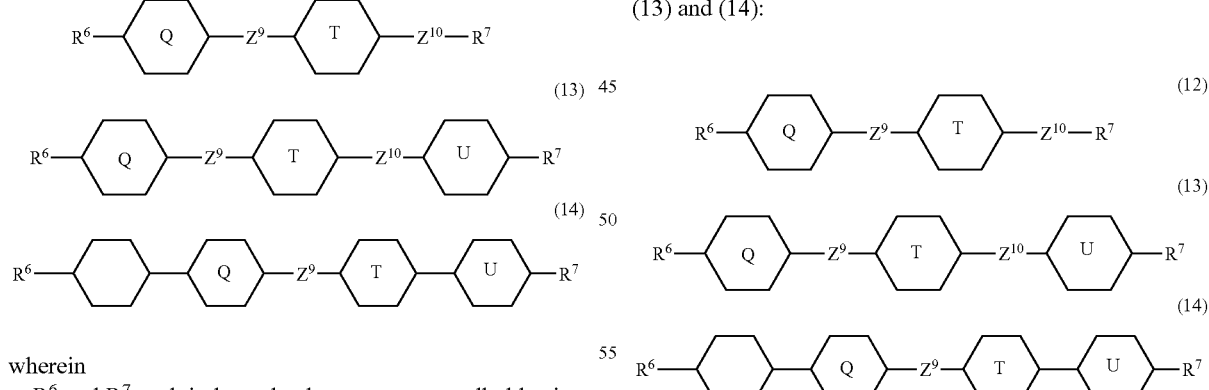

wherein

R[6] and R[7] each independently represents an alkyl having from 1 to 10 carbon atoms; and in this alkyl, any —CH$_2$— may be replaced by —O— or —CH═CH—, and any hydrogen may be replaced by fluorine;

ring Q, ring T, and ring U each independently represents 1,4-cyclohexylene, pyrimidine-2,5-diyl, or fluorinated 1,4-phenylene in which any hydrogen is replaced by fluorine; and $Z^9$ and $Z^{10}$ each independently represents —C≡C—, —COO—, —(CH$_2$)$_2$—, —CH=CH—, or a single bond.

30. The liquid crystal composition according to claim 25, containing at least one compound selected from the group consisting of compounds represented by the formulae (12), (13) and (14):

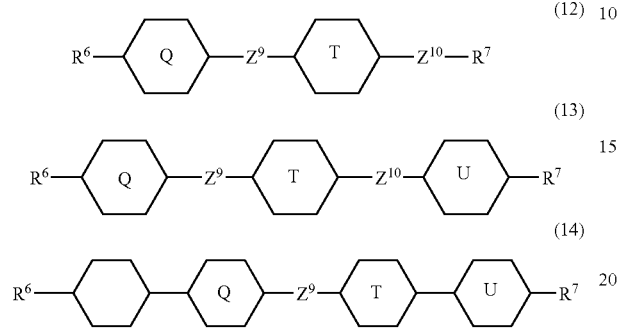

wherein
$R^6$ and $R^7$ each independently represents an alkyl having from 1 to 10 carbon atoms; and in this alkyl, any —CH$_2$— may be replaced by —O— or —CH=CH—, and any hydrogen may be replaced by fluorine;
ring Q, ring T, and ring U each independently represents 1,4-cyclohexylene, pyrimidine-2,5-diyl, or fluorinated 1,4-phenylene in which any hydrogen is replaced by fluorine; and
$Z^9$ and $Z^{10}$ each independently represents —C≡C—, —COO—, —(CH$_2$)$_2$—, —CH=CH—, or a single bond.

31. The liquid crystal composition according to claim 26, containing at least one compound selected from the group consisting of compounds represented by the formulae (12), (13) and (14):

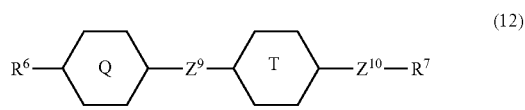

wherein
$R^6$ and $R^7$ each independently represents an alkyl having from 1 to 10 carbon atoms; and in this alkyl any —CH$_2$— may be replaced by —O— or —CH=CH—, and any hydrogen may be replaced by fluorine;
ring Q, ring T, and ring U each independently represents 1,4-cyclohexylene, pyrimidine-2,5-diyl, or fluorinated 1,4-phenylene in which any hydrogen is replaced by fluorine; and
$Z^9$ and $Z^{10}$ each independently represents —C≡C—, —COO—, —(CH$_2$)$_2$—, CH=CH, or a single bond.

32. The liquid crystal composition according to claim 23, further containing at least one optically active compound.

33. The liquid crystal composition according to claim 24, further containing at least one optically active compound.

34. A liquid crystal display device containing the liquid crystal composition according to claim 23.

35. A liquid crystal display device containing the liquid crystal composition according to claim 24.

36. A liquid crystal display device containing the liquid crystal composition according to claim 33.

\* \* \* \* \*